United States Patent [19]

Fröstl et al.

[11] Patent Number: 5,112,855
[45] Date of Patent: May 12, 1992

[54] HYDROGENATED 1-BENZOOXACYCLOALKYL-PYRIDINECARBOXYLIC ACID COMPOUNDS AND COMPOSITIONS

[75] Inventors: Wolfgang Fröstl; Armin Züst, both of Basel, Switzerland

[73] Assignee: Ciba-Geigy Corporation, Ardsley, N.Y.

[21] Appl. No.: 541,227

[22] Filed: Jun. 20, 1990

Related U.S. Application Data

[60] Division of Ser. No. 288,332, Dec. 21, 1988, Pat. No. 4,957,928, which is a continuation-in-part of Ser. No. 63,188, Jun. 16, 1987, abandoned.

[30] Foreign Application Priority Data

Jun. 26, 1986 [CH] Switzerland .................. 2588/86
Dec. 23, 1987 [CH] Switzerland .................. 5008/87

[51] Int. Cl.$^5$ .................. A61K 31/35; C07D 311/58
[52] U.S. Cl. .................. 514/456; 514/337; 546/269; 549/407
[58] Field of Search .............. 549/350, 355, 366, 419, 549/426, 438, 441, 444, 451, 452, 407; 514/450, 452; 456, 457, 465, 469, 337; 546/269

[56] References Cited

U.S. PATENT DOCUMENTS

| | | | |
|---|---|---|---|
| 2,366,102 | 12/1944 | Grün | 544/148 |
| 3,166,561 | 1/1965 | Janssen | 260/294 |
| 4,104,396 | 8/1978 | Huebner | 424/267 |
| 4,235,915 | 11/1980 | Archibald et al. | 424/267 |
| 4,238,488 | 12/1980 | Howe et al. | 424/248.55 |
| 4,321,270 | 3/1982 | Sundeen | 424/267 |
| 4,329,348 | 5/1982 | Huebner | 424/251 |
| 4,383,999 | 5/1983 | Bondinell et al. | 424/266 |
| 4,446,141 | 5/1984 | Nakamizo et al. | 424/267 |
| 4,579,845 | 4/1986 | Cornu et al. | 514/212 |
| 4,738,963 | 4/1988 | Hamilton et al. | 514/254 |

FOREIGN PATENT DOCUMENTS

| | | |
|---|---|---|
| 1971388 | 1/1988 | Australia . |
| 0076530 | 4/1983 | European Pat. Off. . |
| 0176689 | 4/1986 | European Pat. Off. . |
| 0207614 | 1/1987 | European Pat. Off. . |
| 0222996 | 5/1987 | European Pat. Off. . |
| 0932487 | 7/1963 | United Kingdom . |
| 1520801 | 8/1978 | United Kingdom . |

OTHER PUBLICATIONS

Chemical Abstracts 100:174667w (1984).
Chem. Abstract, vol. 61, No. 9491g (1964).

*Primary Examiner*—Mary C. Lee
*Assistant Examiner*—Jacqueline Haley
*Attorney, Agent, or Firm*—Irving M. Fishman; Karen G. Kaiser

[57] ABSTRACT

The invention relates to novel hydrogenated 1-benzooxacycloalkylpyridinecarboxylic acid compounds of formula

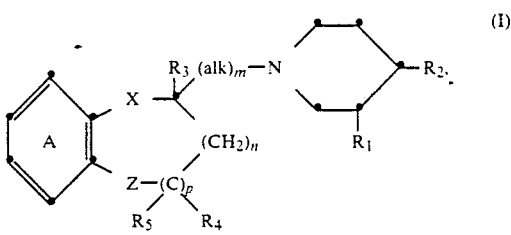

in which the variables $R_1$, $R_2$, $R_3$, $R_4$, $R_5$, alk, X, Z, m, n and p, the dotted line and the substituents of the ring A have the meanings indicated in the specification and in the claims, and to their tautomers and/or salts. These compounds can be used as pharmaceutical active ingredients and can be prepared in a manner known per se.

9 Claims, No Drawings

HYDROGENATED 1-BENZOOXACYCLOALKYLPYRIDINECARBOXYLIC ACID COMPOUNDS AND COMPOSITIONS

This is a divisional of application Ser. No. 288,332, filed on Dec. 21, 1988, now U.S. Pat. No. 4,957,928, which is a continuation-in-part of Ser. No. 063,188, filed Jun. 16, 1987, now abandoned.

The invention relates to novel hydrogenated 1-benzooxacycloalkylpyridinecarboxylic acid compounds of the formula

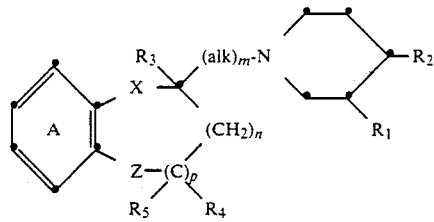

(I)

in which alk is lower alkylene or lower alkylidene, the dotted line is intended to indicate the presence of a single or a double bond between the carbon atoms carrying the substituents $R_1$ and $R_2$, $R_3$ is hydrogen or lower alkyl, $R_4$ is lower alkyl, $R_5$ is lower alkyl, and in which (A) either $R_1$ represents carboxy, lower alkoxycarbonyl, carbamoyl, N-lower alkylcarbamoyl, N,N-di-lower alkylcarbamoyl or optionally acylated hydroxymethyl and $R_2$ represents hydrogen, an optionally etherified or acylated hydroxy group or an optionally acylated amino group, or $R_1$ represents hydrogen and $R_2$ represents carboxy, lower alkoxycarbonyl, carbamoyl, N-lower alkylcarbamoyl, N,N-di-lower alkyl carbamoyl or optionally acylated hydroxymethyl, and in which the ring A is unsubstituted or is mono- or poly-substituted by hydroxy, lower alkoxy, lower alkanoyloxy, halogen, lower alkyl and/or by trifluoromethyl, p is 0, m is 1, and in which either each of X and Z is an oxygen atom and n is 1, or X is a methylene group, Z is an oxygen atom and n is 1, or X is an oxygen atom, Z is a methylene group and n is 1, or X is a direct bond, Z is an oxygen atom and n is 2, with the proviso, that $R_2$ is different from carbamoyl, if $R_1$ is hydrogen, $R_3$ is hydrogen, alk is methylene, ethylene or 1,3-propylene, the ring A is unsubstituted or is monosubstituted in the 6- or 7-position or is disubstituted in the 6- and 7-position, substituents being selected from the group consisting of lower alkoxy, halogen, lower alkyl and trifluoromethyl, the dotted line is intended to indicate the presence of a single bond, each of X and Z is an oxygen atom, and n is 1, or if $R_1$ represents hydrogen, $R_3$ is hydrogen, alk represents ethylidene, the ring A is unsubstituted, the dotted line is intended to indicate the presence of a single bond, each of X and Z is an oxygen atom, and n is 1, or in which (B) either $R_1$ is carboxy, lower alkoxycarbonyl, amidated carboxy or free or acylated hydroxymethyl and $R_2$ is hydrogen, a free, etherified or acylated hydroxy group or a free or acylated amino group, or $R_1$ is hydrogen and $R_2$ is carboxy, lower alkoxycarbonyl, amidated carboxy or free or acylated hydroxymethyl, and in which the ring A is unsubstituted or is mono- or poly-substituted by hydroxy, lower alkoxy, lower alkanoyloxy, cyano, halogen, lower alkyl and/or by trifluoromethyl, p is 1, m is 0 or 1, Z is an oxygenatom, and in which either X is an oxygen atom or a methylene group and n is 0, or X is a direct bond and n is 1, and to their tautomers and/or salts, to the use of these compounds, to a process for the preparation thereof, and to pharmaceutical compositions containing a compound of formula I or a tautomer and/or a pharmaceutically acceptable salt thereof.

The invention relates especially to the groups of compounds of the formula I which is made up by the compounds of the formula

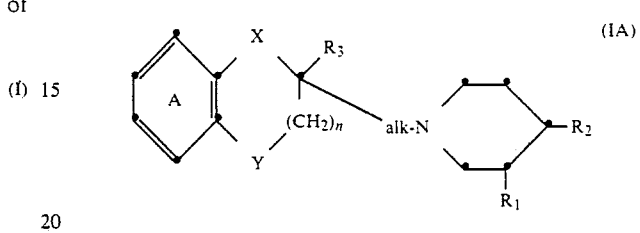

(IA)

in which either $R_1$ represents carboxy, lower alkoxycarbonyl, carbamoyl, N-lower alkylcarbamoyl, N,N-di-lower alkylcarbamoyl or optionally acylated hydroxymethyl and $R_2$ represents hydrogen, an optionally etherified or acylated hydroxy group or an optionally acylated amino group, or $R_1$ represents hydrogen and $R_2$ represents carboxy, lower alkoxycarbonyl, carbamoyl, N-lower alkylcarbamoyl, N,N-di-lower alkyl carbamoyl or optionally acylated hydroxymethyl, $R_3$ represents hydrogen or lower alkyl, alk represents lower alkylene or lower alkylidene, the ring A is unsubstituted or is mono- or poly-substituted by hydroxy, lower alkoxy, lower alkanoyloxy, halogen, lower alkyl and/or by trifluoromethyl, the dotted line is intended to indicate the presence of a single or a double bond, and either each of X and Y represents an oxygen atom and n represents 1, or X represents a methylene group, Y represents an oxygen atom and n represents 1, or X represents an oxygen atom, Y represents a methylene group and n represents 1, or X represents a direct bond, Y represents an oxygen atom and n represents 2, with the proviso that $R_2$ is different from carbamoyl, if $R_1$ represents hydrogen, $R_3$ is hydrogen, alk represents methylene, ethylene or 1,3-propylene, the ring A is unsubstituted or is monosubstituted in the 6- or 7-position or is disubstituted in the 6- and 7-position, substituents being selected from the group consisting of lower alkoxy, halogen, lower alkyl and trifluormethyl, the dotted line is intended to indicate the presence of a single bond, each of X and Y represents an oxygen atom and n represents 1, or if $R_1$ represents hydrogen, $R_3$ is hydrogen, alk represents ethylidene, the ring A is unsubstituted, the dotted line is intended to indicate the presence of a single bond, each of X and Y represents an oxygen atom and n represents 1; and to their tautomers and/or salts, to the use of these compounds, to processes for their manufacture and to pharmaceutical compositions containing a compound of the formula IA or a tautomer and/or a pharmaceutically acceptable salt thereof.

The invention relates also especially to the group of compounds of the formula I which is made up by the compounds of the formula

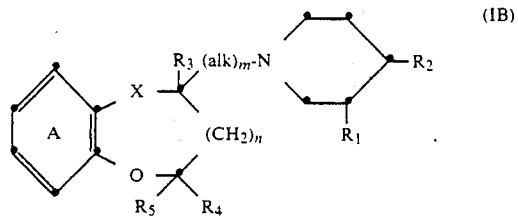

(IB)

in which either $R_1$ is carboxy, lower alkoxycarbonyl, amidated carboxy or free or acylated hydroxymethyl and $R_2$ is hydrogen, a free, etherified or acylated hydroxy group or a free or acylated amino group, or $R_1$ is hydrogen and $R_2$ is carboxy, lower alkoxycarbonyl, amidated carboxy or free or acylated hydroxymethyl, and in which $R_3$ is hydrogen or lower alkyl, $R_4$ is lower alkyl, $R_5$ is lower alkyl, alk is lower alkylene or lower alkylidene, the ring A is unsubstituted or is mono- or poly-substituted by hydroxy, lower alkoxy, lower alkanoyloxy, cyano, halogen, lower alkyl and/or by trifluoromethyl, the dotted line is intended to indicate the presence of a single or a double bond between the carbon atoms carrying the substituents $R_1$ and $R_2$, m is 0 or 1, and in which either X is an oxygen atom or a methylene group and n is 0, or X is a direct bond and n is 1, and to their tautomers and/or salts, to the use of these compounds, to a process for the preparation thereof, and to pharmaceutical compositions containing a compound of formula IB or a tautomer and/or a pharmaceutically acceptable salt thereof.

Amidated carboxy $R_1$ and $R_2$ has as amino group, for example, amino that is unsubstituted or is mono- or di-substituted by lower aliphatic radicals and is, for example, carbamoyl, N-lower alkyl- or N,N-di-lower alkylcarbamoyl or N,N-lower alkylene- or N,N-(aza)-, N,N-(oxa)- or N,N-(thia)-lower alkylenecarbamoyl.

Etherified hydroxy $R_2$ is, for example, lower alkoxy or optionally substituted phenyl-lower alkoxy.

Acyl in acylated hydroxymethyl $R_1$ and $R_2$, respectively, and also in acylated hydroxy $R_2$ and acylated amino $R_2$, respectively, is, for example, acyl derived from an organic carboxylic or sulphonic acid.

Acyl derived from an organic carboxylic acid is, for example, the radical of an aliphatic or monocyclic-aromatic carboxylic acid, such as lower alkanoyl or optionally substituted benzoyl, and also pyridoyl.

Acyl derived from an organic sulphonic acid is, for example, lower alkanesulphonyl.

The invention relates, for example, to compounds of the formula IA in which $R_1$ represents carboxy, lower alkoxycarbonyl, carbamoyl, N-lower alkylcarbamoyl or N,N-di-lower alkylcarbamoyl, $R_2$ represents hydrogen, an optionally etherified or acylated hydroxy group or an optionally acylated amino group, $R_3$ represents hydrogen or lower alkyl, alk represents lower alkylene or lower alkylidene, the ring A is unsubstituted or is mono- or poly-substituted by hydroxy, lower alkoxy, lower alkanoyloxy, halogen, lower alkyl and/or by trifluoromethyl, the dotted line is intended to indicate the presence of a single or a double bond, X represents an oxygen atom or a methylene group, Y represents an oxygen atom and n represents 1, and to their tautomers and/or salts, to the use of these compounds, to processes for their manufacture and to pharmaceutical compositions containing such a compound of the formula IA or a tautomer and/or a pharmaceutically acceptable salt thereof.

Tautomeric forms of compounds of formula I exist, for example, when $R_2$ is hydroxy or amino and the dotted line is intended to indicate the presence of a double bond between the carbon atoms carrying the substituents $R_1$ and $R_2$. The enols or enamines of formula I are then in equilibrium with the corresponding keto or ketimine tautomers, respectively, of the formula

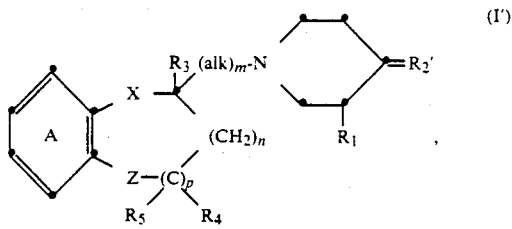

(I')

in which $R_2'$ is oxo or imino, respectively. Representatives of both tautomeric forms can be isolated.

The compounds according to the invention can also be in the form of stereoisomers. Since the compounds of formula I have at least one chiral carbon atom (C-atom) (for example the C-atom carrying the radical $R_3$), they may be, for example, in the form of pure enantiomers or enantiomeric mixtures, such as racemates, and if there is at least one further chiral centre present (for example the $C_4$-atom of a piperidine radical 4-substituted by $R_2$ other than hydrogen and/or the $C_3$-atom of a piperidine radical 3-substituted by $R_1$ other than hydrogen), they may also be in the form of diastereoisomers, diastereoisomeric mixtures or mixtures of racemates. Thus, for example, geometrical isomers with respect to $R_1$ and $R_2$, such as cis- and trans-isomers, may be formed if $R_1$ and $R_2$ are other than hydrogen and the dotted line indicates the presence of a single bond between the carbon atoms carrying the substituents $R_1$ and $R_2$.

Salts of compounds of formula I and their tautomers are especially corresponding acid addition salts, preferably pharmaceutically acceptable acid addition salts. These are formed, for example, with strong inorganic acids, such as mineral acids, for example sulfuric acid, a phosphoric acid or a hydrohalic acid, with strong organic carboxylic acids, such as lower alkanecarboxylic acids, for example acetic acid, saturated or unsaturated dicarboxylic acids, for example malonic, maleic or fumaric acid, or hydroxycarboxylic acids, for example tartaric or citric acid, or with sulfonic acids, such as lower alkanesulfonic acids or unsubstituted or substituted benzenesulfonic acids, for example methane- or p-toluenesulfonic acid. If, for example, $R_1$ or $R_2$ is carboxy, corresponding compounds may form salts with bases. Suitable salts with bases are, for example, corresponding alkali metal or alkaline earth metal salts, for example sodium, potassium or magnesium salts, pharmaceutically acceptable transition metal salts, such as zinc or copper salts, or salts with ammonia or organic amines, such as cyclic amines, mono-, di- or tri-lower alkylamines, hydroxy-lower alkylamines, for example mono-, di- or tri-hydroxy-lower alkylamines, hydroxy-lower alkyl-lower alkylamines or polyhydroxy-lower alkylamines. Cyclic amines are, for example, morpholine, thiomorpholine, piperidine or pyrrolidine. Suitable mono-lower alkylamines are, for example, ethylamine or tert.-butylamine; suitable di-lower alkylamines are, for example, diethylamine or diisopropylamine, and suitable tri-lower alkylamines are, for example, trimethylamine or triethylamine. Corresponding hydroxy-lower alkylamines are, for example, mono-, di- or tri-ethanolamine, and hydroxy-lower alkyl-lower alkylamines are, for example, N,N-dimethylamino- or N,N-diethylamino-ethanol, and a suitable polyhydroxy-lower alkylamine is, for example, glucosamine.

Also included are salts that are unsuitable for pharmaceutical uses, since they can be used, for example, for the isolation and purification of free compounds according to the invention and their pharmaceutically acceptable salts.

Hereinbefore and hereinafter, unless defined otherwise, radicals or compounds designated "lower" are to be understood as being especially those radicals or compounds which contain up to and including 7, especially up to and including 4, carbon atoms.

Lower alkoxy is, for example, $C_1-C_4$alkoxy, such as methoxy, ethoxy, n-propoxy, isopropoxy, n-butoxy, isobutoxy or tert.-butoxy.

Lower alkyl is, for example, $C_1-C_4$alkyl, such as methyl, ethyl, n-propyl, isopropyl, n-butyl, isobutyl, sec.-butyl or tert.-butyl, and also includes $C_5-C_7$alkyl radicals, that is to say pentyl, hexyl or heptyl radicals.

Lower alkylene alk is, for example, $C_1-C_4$alkylene that bridges the two ring systems shown in formula I especially by up to and including 3 carbon atoms and may be, for example, methylene, ethylene or 1,3-propylene, but may also be 1,2-propylene, 1,2-or 1,3-(2-methyl)propylene or 1,2- or 1,3-butylene, but it may also bridge the two ring systems by 4 carbon atoms, that is to say it may be 1,4-butylene.

Lower alkylidene alk is, for example, $C_1-C_4$alkylidene and may be, for example, methylene, ethylidene, 1,1- or 2,2-propylidene or 1,1- or 2,2-butylidene.

Lower alkanoyl is, for example, $C_2-C_5$alkanoyl, such as acetyl, propionyl, butyryl, isobutyryl or pivaloyl.

Lower alkanoyloxy is, for example, $C_2-C_5$alkanoyloxy, such as acetoxy, propionyloxy, butyryloxy, isobutyryloxy or pivaloyloxy.

Lower alkoxycarbonyl is, for example, $C_2-C_5$alkoxycarbonyl, such as methoxy-, ethoxy-, n-propoxy-, isopropoxy, n-butoxy-, isobutoxy- or tert.-butoxy-carbonyl.

N-lower alkylcarbamoyl is, for example, N-$C_1$-$C_4$alkylcarbamoyl, such as N-methyl-, N-ethyl-, N-(n-propyl)-, N-isopropyl-, N-(n-butyl)-, N-isobutyl-or N-tert.-butyl-carbamoyl.

N,N-di-lower alkylcarbamoyl is, for example, N,N-di-$C_1-C_4$alkylcarbamoyl in which the two N-alkyl groups may be the same or different, such as N,N-dimethyl-, N,N-diethyl-, N,N-diisopropyl- or N-butyl-N-methylcarbamoyl.

N,N-lower alkylene- or N,N-(aza)-, N,N-(oxa)- or N,N-(thia)-lower alkylene-carbamoyl has, for example, from 3 up to and including 8, especially 5 or 6, ring members and is, for example, pyrrolidino-, piperidino-, piperazino-, or N'-lower alkyl-, such as N'-methyl-piperazino-, morpholino- or thiomorpholino-carbonyl.

Unsubstituted or substituted phenyl-lower alkoxy is, for example, phenyl-$C_1-C_4$alkoxy that is unsubstituted or substituted in the phenyl moiety, such as benzyloxy, p-chlorobenzyloxy, 1-phenylethoxy or 1-(p-bromophenyl)-n-butoxy.

Unsubstituted or substituted benzoyl is, for example, benzoyl, p-chlorobenzoyl or p-nitrobenzoyl.

Lower alkanesulfonyl is, for example, $C_1-C_4$alkanesulfonyl, such as methane- or ethane-sulfonyl.

Halogen is especially halogen having an atomic number of up to and including 35, such as fluorine, chlorine or bromine, and also includes iodine.

The compounds of formula I, their tautomers and/or their pharmaceutically acceptable salts have, for example, valuable pharmacological, especially nootropic, properties. Thus, for example, in mice, in the Two-Compartment Passive Avoidance Test model according to Mondadori and Classen, Acta Neurol. Scand. 69, Suppl. 99, 125 (1984), at dosages of approximately 0.1 mg/kg and above i.p. and p.o. they bring about a reduction in the amnesic effect of a cerebral electric shock.

The compounds according to the invention also exhibit a considerable memory-improving action which can be detected in mice in the Step-down Passive Avoidance Test according to Mondadori and Waser, Psychopharmacol. 63, 297 (1979) at a dose of approximately 0.1 mg/kg and above i.p. and p.o.

Accordingly, the compounds of formula I and their tautomers and/or their pharmaceutically acceptable salts can be used as pharmaceuticals, for example nootropics, for example for the therapeutic and/or prophylactic treatment of the symptoms of cerebral insufficiency, especially memory disorders. The invention therefore relates also to the use of compounds of formula I, their tautomers and/or their pharmaceutically acceptable salts for the manufacture of medicaments, especially nootropics, for the treatment of the symptoms of cerebral insufficiency, especially memory disorders, which may also include the commercial formulation of the active ingredients.

The invention relates, in appropriate consideration of the afore-mentioned proviso, especially to compounds of the formula IA in which either $R_1$ represents carboxy, lower alkoxycarbonyl, carbamoyl, N-lower alkylcarbamoyl, N,N-di-lower alkylcarbamoyl, hydroxymethyl, lower alkanoyloxymethyl, lower alkanesulphonyloxymethyl, benzoyloxymethyl or pyridoyloxymethyl and $R_2$ represents hydrogen, hydroxy, lower alkoxy, benzyloxy, lower alkanoyloxy, lower alkanesulphonyloxy, benzoyloxy, pyridoyloxy, amino, lower alkanoylamino, lower alkanesulphonylamino, benzoylamino or pyridoylamino, or $R_1$ represents hydrogen and $R_2$ represents carboxy, lower alkoxycarbonyl, carbamoyl, N-lower alkylcarbamoyl, N,N-di-lower alkylcarbamoyl, hydroxymethyl, lower alkanoyloxymethyl, lower alkanesulphonyloxymethyl, benzoyloxymethyl or pyridoyloxymethyl, $R_3$ represents hydrogen or lower alkyl, alk represents lower alkylene that bridges the two ring systems by up to and including 3 carbon atoms, or alk represents lower alkylidene, the ring A is unsubstituted or is mono-, di- or poly-substituted by hydroxy, lower alkoxy, lower alkanoyloxy, halogen, lower alkyl and/or by trifluoromethyl, the dotted line is intended to indicate the presence of a single or a double bond, and either each of X and Y represents an oxygen atom and n represents 1, or X represents a methylene group, Y represents an oxygen atom and n represents 1, or X represents an oxygen atom, Y represents a methylene group and n represents 1, or X represents a direct bond, Y represents an oxygen atom and n represents 2, for example compounds of the formula IA in which $R_1$ represents carboxy, lower alkoxycarbonyl, carbamoyl, N-lower alkylcarbamoyl or N,N-di-lower alkylcarbamoyl, $R_2$ represents hydrogen, hydroxy, lower alkoxy, benzyloxy, lower alkanoyloxy, lower alkanesulphonyloxy, benzoyloxy, pyridoyloxy, amino, lower alkanoylamino, benzoylamino or pyridoylamino, $R_3$ represents hydrogen or lower alkyl, alk represents lower alkylene that bridges the two ring systems by up to and including 3 carbon atoms, or alk represents lower alkylidene, the ring A is unsubstituted or is mono-, di- or poly-substituted by hydroxy, lower alkoxy, lower alkanoyloxy, halogen, lower alkyl and/or by trifluoromethyl, the dotted line is intended to indicate the presence of a single or a double bond, X represents an oxygen atom or a methylene group, Y represents an oxygen atom and n represents 1, and to their tautomers and/or salts.

The invention relates more especially to compounds of the formula IA in which either $R_1$ represents $C_1$–$C_4$-alkoxycarbonyl, such as methoxy- or ethoxycarbonyl, carbamoyl, hydroxymethyl or $C_2$–$C_5$-alkanoyloxymethyl, such as acetoxymethyl, and $R_2$ represents hydrogen or hydroxy, or $R_1$ represents hydrogen and $R_2$ represents $C_1$–$C_4$-alkoxycarbonyl, such as ethoxycarbonyl, $R_3$ represents hydrogen or $C_1$–$C_4$-alkyl, such as methyl, alk represents $C_1$–$C_4$-alkylene that bridges the two ring systems by up to and including 3 carbon atoms, such as methylene or ethylene, the ring A is unsubstituted or is substituted, especially in the 7-position, by $C_1$–$C_4$-alkoxy, such as methoxy, the dotted line is intended to indicate the presence of a single or a double bond, and either each of X and Y represents an oxygen atom and n represents 1, or X represents a methylene group, Y represents an oxygen atom and n represents 1, or X represents an oxygen atom, Y represents a methylene group and n represents 1, or X represents a direct bond, Y represents an oxygen atom and n represents 2, for example compounds of the formula IA in which $R_1$ represents $C_1$–$C_4$-alkoxycarbonyl, such as methoxycarbonyl, $R_2$ represents hydrogen or hydroxy, $R_3$ represents hydrogen or $C_1$–$C_4$-alkyl, such as methyl, alk represents $C_1$–$C_4$-alkylene that bridges the two ring systems by up to and including 3 carbon atoms, such as methylene or ethylene, the ring A is unsubstituted, the dotted line is intended to indicate the presence of a single or a double bond, X represents an oxygen atom or a methylene group, Y represents an oxygen atom and n represents 1, and to their tautomers and/or salts.

The invention relates especially to compounds of the formula IA in which $R_1$ represents $C_1$–$C_4$-alkoxycarbonyl, such as methoxy- or ethoxy-carbonyl, $R_2$ represents hydrogen or hydroxy, $R_3$ represents hydrogen, alk represents methylene or ethylene, the ring A is unsubstituted, the dotted line is intended to indicate the presence of a single or a double bond, X represents an oxygen atom or a methylene group, Y represents an oxygen atom and n represents 1, and to their tautomers and/or salts.

The invention relates most especially to compounds of the formula IA in which $R_1$ represents $C_1$–$C_4$-alkoxycarbonyl, such as methoxycarbonyl, $R_2$ represents hydrogen, $R_3$ represents hydrogen, alk represents methylene or ethylene, the ring A is unsubstituted, the dotted line is intended to indicate the presence of a single or a double bond, X represents an oxygen atom or a methylene group, Y represents an oxygen atom and n represents 1, or in which $R_1$ represents $C_1$–$C_4$-alkoxycarbonyl, such as methoxycarbonyl, $R_2$ represents hydroxy, $R_3$ represents hydrogen, alk represents methylene, the ring A is unsubstituted, the dotted line is intended to indicate the presence of a double bond, X represents an oxygen atom or a methylene group, Y represents an oxygen atom and n represents 1, and in each case to their tautomers and/or salts.

The invention relates especially to compounds of formula IB in which either $R_1$ is carboxy, lower alkoxycarbonyl, carbamoyl, N-lower alkylcarbamoyl, N,N-di-lower alkylcarbamoyl, N,N-lower alkylenecarbamoyl, N,N-(aza)-, N,N-(oxa)- or N,N-(thia)-lower alkylenecarbamoyl, hydroxymethyl, lower alkanoyloxymethyl, lower alkanesulfonyloxymethyl, benzoyloxymethyl or pyridoyloxymethyl and $R_2$ is hydrogen, hydroxy, lower alkoxy, benzyloxy, lower alkanoyloxy, lower alkanesulfonyloxy, benzoyloxy, pyridoyloxy, amino, lower alkanoylamino, lower alkanesulfonylamino, benzoylamino or pyridoylamino, or $R_1$ is hydrogen and $R_2$ is carboxy, lower alkoxycarbonyl, carbamoyl, N-lower alkylcarbamoyl, N,N-di-lower alkylcarbamoyl, N,N-lower alkylenecarbamoyl, N,N-(aza)-, N,N-(oxa)- or N,N-(thia)-lower alkylenecarbamoyl, hydroxymethyl, lower alkanoyloxymethyl, lower alkanesulfonyloxymethyl, benzoyloxymethyl or pyridoyloxymethyl, and in which $R_3$ is hydrogen or lower alkyl, $R_4$ is lower alkyl, $R_5$ is lower alkyl, alk is lower alkylene that bridges the two ring systems shown in formula IB by up to and including 3 carbon atoms or is lower alkylidene, the ring A is unsubstituted or is mono-, di- or poly-substituted by hydroxy, lower alkoxy, lower alkanoyloxy, cyano, halogen, lower alkyl and/or by trifluoromethyl, the dotted line is intended to indicate the presence of a single or a double bond between the carbon atoms carrying the substituents $R_1$ and $R_2$, m is 0 or 1, and in which either X is an oxygen atom or a methylene group and n is 0, or X is a direct bond and n is 1, and their tautomers and/or salts.

The invention relates more especially to compounds of formula IB in which $R_1$ is $C_1$–$C_4$alkoxycarbonyl, such as methoxy- or ethoxy-carbonyl, or carbamoyl, $R_2$ is hydrogen or hydroxy, $R_3$ is hydrogen, $R_4$ is $C_1$–$C_4$alkyl, such as methyl, $R_5$ is $C_1$–$C_4$alkyl, such as methyl, alk is $C_1$–$C_4$alkylene that bridges the two ring systems shown in formula IB by up to and including 3 carbon atoms, such as methylene or ethylene, the ring A is unsubstituted or is substituted, especially in the 6-position, by $C_1$–$C_4$alkoxy, such as methoxy, $C_1$–$C_4$alkyl, such as methyl, halogen having an atomic number of up to and including 35, such as fluorine or chlorine, cyano or by trifluoromethyl, the dotted line is intended to indicate the presence of a single or a double bond between the carbon atoms carrying the substituents $R_1$ and $R_2$, m is 1, X is an oxygen atom or a methylene group and n is 0, and their tautomers and/or salts.

The invention relates especially to compounds of formula IB in which $R_1$ is $C_1$–$C_4$alkoxycarbonyl, such as methoxycarbonyl, $R_2$ is hydrogen, $R_3$ is hydrogen, $R_4$ is $C_1$–$C_4$alkyl, such as methyl, $R_5$ is $C_1$–$C_4$alkyl, such as methyl, alk is ethylene, the ring A is unsubstituted or is mono-substituted, especially in the 6-position, by halogen having an atomic number of up to and including 35, such as fluorine or chlorine, the dotted line is intended to indicate the presence of a double bond between the carbon atoms carrying the substituents $R_1$ and $R_2$, m is 1, X is a methylene group and n is 0, and their salts.

The invention relates more especially to compounds of formula IB in which $R_1$ is $C_1$–$C_4$alkoxycarbonyl, such as methoxycarbonyl, $R_2$ is hydrogen, $R_3$ is hydrogen, $R_4$ is $C_1$–$C_4$alkyl, such as methyl, $R_5$ is $C_1$–$C_4$alkyl, such as methyl, alk is ethylene, the ring A is unsubstituted, the dotted line is intended to indicate the presence of a double bond between the carbon atoms carrying the substituents $R_1$ and $R_2$, m is 1, X is a methylene group and n is 0, and their salts.

The invention relates specifically to the novel compounds of formula I mentioned in the Examples and their salts and to process for their preparation.

The present invention relates also to a process for the preparation of compounds of formula I or their tautomers and/or salts, in which process, for example, a) a compound of formula

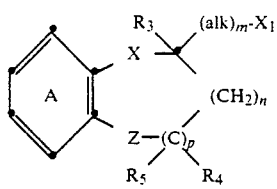
(IIa)

or a salt thereof, in which $X_1$ is hydroxy or reactive esterified hydroxy, is reacted with a compound of formula

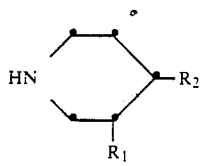
(IIb)

or with a tautomer and/or salt thereof, or b) in a compound of formula

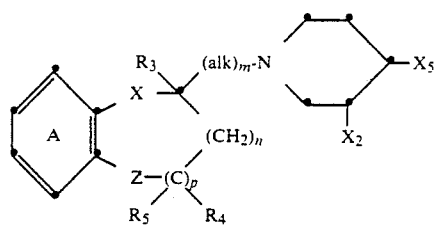
(III)

or in a tautomer and/or salt thereof, in which $X_2$ is a radical that can be converted into $R_1$ other than hydrogen and $X_5$ is a radical $R_a$, and $R_a$ is hydrogen, a free, etherified or acylated hydroxy group or a free or acylated amino group, $X_2$ is converted into $R_1$ other than hydrogen, or in a compound of formula III or in a tautomer and/or salt thereof, in which $X_2$ is hydrogen and $X_5$ is a radical that can be converted into $R_b$, and $R_b$ is a radical $R_2$ other than a radical $R_a$, $X_5$ is converted into $R_b$, or c) for the preparation of a compound of formula I or a tautomer and/or salt thereof, in which $R_2$ is hydroxy or amino and in which $R_1$ is other than hydrogen and other than free or acylated hydroxymethyl, a compound of formula

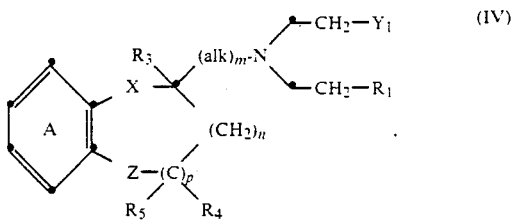
(IV)

in which $Y_1$ is a group of formula $-CH=R_2'$, $-C(Y_2)=R_2'$ or $-CH(Y_2)-R_2$ or cyano, wherein $R_2'$ is oxo or imino and $Y_2$ is a removable radical, or a salt thereof is cyclised, or d) for the preparation of a compound of formula I', in which $R_2'$ is oxo or imino and $R_1$ is other than hydrogen, or a tautomer and/or salt thereof, a compound of formula

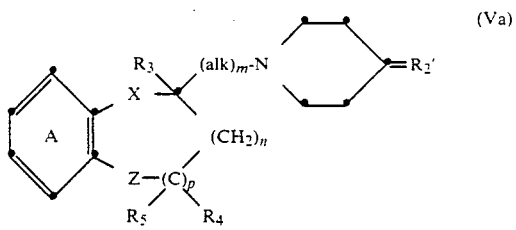
(Va)

or a tautomer and/or a salt thereof is reacted with a compound of formula

$X_3-R_1$ (Vb)

or with a salt thereof, in which $R_1$ is other than hydrogen and $X_3$ is halogen or lower alkoxy, or e) for the preparation of a compound of formula I or a tautomer and/or salt thereof, in which $R_2$ is a free, etherified or acylated hydroxy group or a free or acylated amino group, in a compound of formula

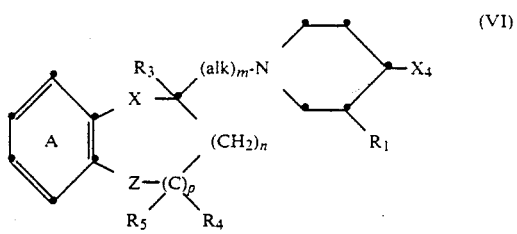
(VI)

or in a salt thereof, in which $X_4$ is a radical that can be converted into $R_2$, $X_4$ is converted into $R_2$, or f) in a salt of formula

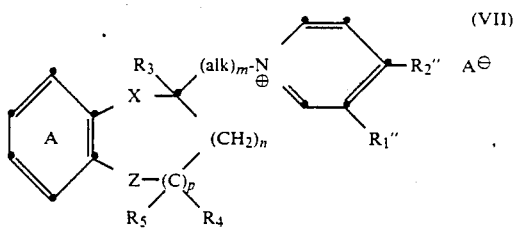
(VII)

in which $A^\ominus$ is the anion of an acid, $R_1''$ is a radical $R_1$ or etherified or protected hydroxymethyl, and $R_2''$ is a radical $R_2$, protected hydroxy, protected amino or etherified or protected hydroxymethyl, the excess double bonds are reduced to single bonds and, if $R_1''$ is other than $R_1$ and/or $R_2''$ is other than $R_2$, $R_1''$ is converted into $R_1$ and/or $R_2''$ is converted into $R_2$, or g) for the preparation of a compound of formula I or a tautomer and/or salt thereof, in which $R_2$ is carboxy, amidated carboxy or lower alkoxycarbonyl and the dotted line is intended to indicate the presence of a single bond between the carbon atoms carrying the substituents $R_1$ and $R_2$, a compound of formula

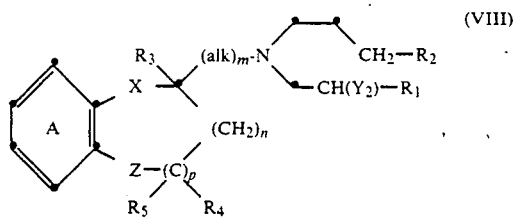

(VIII)

in which $Y_2$ is a removable radical, or a salt thereof is cyclised, and, in the case of each of process variants a) to g), a protecting group which may be present is removed, and, if desired, a compound of formula I obtainable in accordance with the process or by other means is converted into a different compound of formula I, an isomeric mixture obtainable in accordance with the process is separated into the components, an enantiomeric or diastereoisomeric mixture obtainable in accordance with the process is separated into the enantiomers or diastereoisomers, respectively, and/or a free compound of formula I obtainable in accordance with the process is converted into a salt or a salt obtainable in accordance with the process is converted into the free compound of formula I or into a different salt.

The reactions described in the variants hereinbefore and hereinafter are carried out in a manner known per se, for example in the absence or, customarily, in the presence of a suitable solvent or diluent or a mixture thereof, the reactions being carried out, as necessary, with cooling, at room temperature or with heating, for example in a temperature range of from approximately $-10°$ C. to the boiling temperature of the reaction medium, preferably at from approximately 20° C. to approximately 150° C., and, if necessary, in a closed vessel, under pressure, in an inert gas atmosphere and/or under anhydrous conditions.

The starting materials of formulae IIa and IIb, III, IV, Va and Vb, VI, VII and VIII, which are mentioned hereinbefore and hereinafter and which were developed for the preparation of the compounds of formula I, their tautomers and/or salts, are known in some cases or they can likewise be prepared according to methods known per se, for example analogously to the process variants described above.

Starting materials having basic centres may, for example, be in the form of acid addition salts, for example with the acids listed above, whilst starting compounds having acidic groups may form salts with bases, for example of the kind mentioned above. Starting compounds may also be in the form of tautomers, especially in the case of compounds of formula IIb when $R_2$ is hydroxy and the dotted line is intended to indicate the presence of a double bond between the carbon atoms carrying the substituents $R_1$ and $R_2$.

Variant a)

Reactive esterified hydroxy is especially hydroxy esterified by a strong inorganic acid or organic sulfonic acid, for example halogen, such as chlorine, bromine or iodine, sulfonyloxy, such as hydroxysulfonyloxy, halosulfonyloxy, for example fluorosulfonyloxy, lower alkanesulfonyloxy that is unsubstituted or substituted, for example, by halogen, for example methane- or trifluoromethane-sulfonyloxy, cycloalkanesulfonyloxy, for example cyclohexanesulfonyloxy, or benzenesulfonyloxy that is unsubstituted or substituted, for example, by lower alkyl or by halogen, for example p-bromophenyl- or p-toluene-sulfonyloxy.

The N-alkylation is carried out especially in the presence of a condensation agent, such as a suitable base. Suitable bases are, for example, alkali metal hydroxides, hydrides, amides, alkanolates, carbonates, triphenylmethylides, di-lower alkylamides, amino-lower alkylamides or lower alkylsilylamides, or naphthaleneamines, lower alkylamines, basic heterocycles, ammonium hydroxides and carbocyclic amines. There may be mentioned by way of example: sodium hydroxide, hydride, amide or ethanolate, potassium tert.-butanolate or carbonate, lithium triphenylmethylide, lithium diisopropylamide, potassium 3-(aminopropyl)-amide or bis-(trimethylsilyl)-amide, or dimethylaminonaphthalene, di- or triethylamine, pyridine, benzyltrimethylammonium hydroxide, 1,5-diazabicyclo[4.3.0]non-5-ene (DBN) and 1,5-diazabicyclo[5.4.0]undec-5-ene (DBU).

The starting materials of formulae IIa and IIb are either known or they can be prepared analogously to the known starting materials.

Variant b)

A radical $X_2$ that can be converted into $R_1$ other than hydrogen, or a radical $X_5$ that can be converted into a radical $R_b$ is, for example, functionally modified carboxy other than $R_1$ or $R_b$, respectively, such as cyano, anhydridised carboxy, unsubstituted or substituted amidino, free, esterified or anhydridised carboximidoyl, esterified or amidated carboxy other than esterified or amidated carboxy $R_1$ or $R_2$, tri-lower alkoxy- or tri-halo-methyl.

Anhydridised carboxy is, for example, carboxy anhydridised with a mineral acid, such as a hydrohalic acid, or with a carboxylic acid, such as an unsubstituted or substituted lower alkanoic or benzoic acid, or with a carbonic acid halide lower alkyl semiester. Examples that may be mentioned are halocarbonyl, such as chlorocarbonyl, lower alkanoyloxycarbonyl, such as acetoxycarbonyl, or lower alkoxycarbonyloxycarbonyl, such as ethoxycarbonyloxycarbonyl.

Substituted amidino is, for example, amidino substituted by an aliphatic radical, for example lower alkyl, such as lower alkylamidino, for example ethylamidino.

Esterified or anhydridised carboximidoyl is to be understood as being, for example, alkoxy- or halo-carboximidoyl, for example lower alkoxy-, such as ethoxy-, or chlorocarboximidoyl, respectively.

Tri-lower alkoxymethyl or tri-halomethyl is, for example, trimethoxymethyl or trichloromethyl, respectively.

Radicals $R_b$ are, for example, carboxy, lower alkoxycarbonyl, amidated carboxy or free or acylated hydroxymethyl radicals $R_2$.

$X_2$ can be converted into $R_1$ other than hydrogen, for example, by solvolysis, just as $X_5$ can be converted into a radical $R_b$, for example, by solvolysis. Solvolysis agents are, for example, water, lower alkanols corresponding to the desired esterified carboxy $R_1$ and $R_2$, ammonia, or amines corresponding to the desired amidated carboxy group $R_1$ and $R_2$. The treatment with a corresponding solvolysis agent is if appropriate carried out in the presence of an acid or base. Suitable acids are, for example, inorganic or organic protonic acids, such as mineral acids, for example sulfuric acid or a hydrohalic acid, for example hydrochloric acid, sulfonic acids, for example lower alkanesulfonic acids or unsubstituted or substituted benzenesulfonic acids, for example methane- or p-toluenesulfonic acid, or carboxylic acids, for example lower alkanecarboxylic acids, for example acetic acid, whilst bases that may be used are, for example, those mentioned under Variant a), especially sodium or potassium hydroxide.

In the solvolysis, the cyano group, anhydridised carboxy, unsubstituted or substituted amidino, free, esterified or anhydridised carboximidoyl, esterified or amidated carboxy other than esterified or amidated carboxy $R_1$ and $R_2$, tri-lower alkoxymethyl or trihalomethyl is hydrolysed to carboxy. Lower alkanoyloxy radicals which may be present at ring A may also be hydrolysed to hydroxy in the course of the hydrolysis.

Cyano, anhydridised carboxy, and esterified or amidated carboxy other than esterified or amidated carboxy $R_1$ and $R_2$ are alcoholysed, for example with a suitable lower alkanol, to esterified carboxy $R_1$ and $R_2$, and cyano and anhydridised carboxy are ammonolysed or aminolysed, for example, with ammonia or with an amine corresponding to the amidated carboxy $R_1$ and $R_2$, respectively.

The starting material of formula III can be prepared, for example, in a manner analogous to that described under Variant a) by reacting a compound of formula

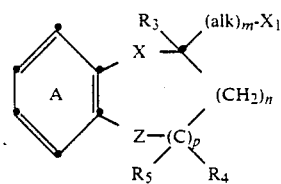
(IIa)

with a compound of formula

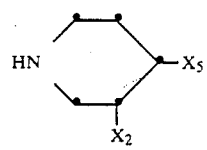
(IIIa)

or with a tautomer and/or salt thereof, in the presence of one of the mentioned bases.

Compounds of formula III in which $X_2$ is a radical that can be converted into $R_1$ other than hydrogen and $X_5$ is hydroxy or amino, can advantageously be prepared also by cyclisation of a compound of formula

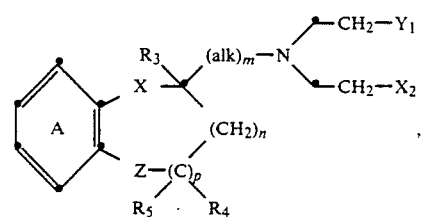
(IVg)

in which $Y_1$ is a group of formula $-CH=R_2'$, $-C(Y_2)=R_2'$, $-CH(Y_2)-R_2$ or cyano, wherein $R_2'$ is oxo or imino, $R_2$ is hydroxy or amino and $Y_2$ is a removable radical, or a salt thereof, the operation being carried out, for example, in a manner analogous to that given under Process Variant c).

Variant c)

Removable radicals $Y_2$ in groups of formula $-C(Y_2)=R_2'$ or $-CH(Y_2)-R_2$ are, for example, reactive esterified hydroxy groups, such as hydroxy esterified by a strong inorganic acid or organic sulfonic acid, for example halogen, such as chlorine, bromine or iodine, sulfonyloxy, such as hydroxysulfonyloxy, halosulfonyloxy, for example fluorosulfonyloxy, lower alkanesulfonyloxy that is unsubstituted or substituted, for example, by halogen, for example methane- or trifluoromethane-sulfonyloxy, cycloalkanesulfonyloxy, for example cyclohexanesulfonyloxy, or benzenesulfonyloxy that is unsubstituted or substituted, for example, by lower alkyl or by halogen, for example p-bromophenyl- or p-toluene-sulfonyloxy, or etherified hydroxy groups, for example lower alkoxy or unsubstituted or substituted phenyl-lower alkoxy.

The cyclisation can be carried out, for example, analogously to the Dieckmann reaction, especially in the presence of one of the bases mentioned under Variant a), and with subsequent working up by means of hydrolysis.

In a preferred form of the process, for example a compound of formula

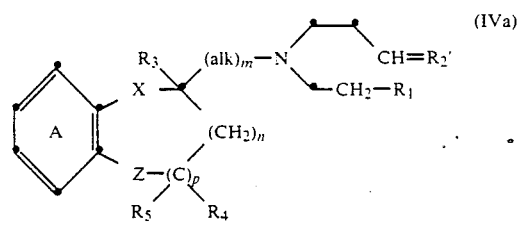
(IVa)

in which $R_2'$ is oxo or imino, can be subjected to treatment with one of the mentioned bases, especially with an alkali metal lower alkanolate, for example with sodium methanolate or sodium ethanolate. During this treatment, the compound IVa cyclises to form a compound of formula I in which the dotted line indicates the presence of a single bond between the carbon atoms carrying the substituents $R_1$ and $R_2$, and $R_2$ is hydroxy or amino. Starting materials of formula IVa are obtained, for example, by reacting a reactive alkyl ester of formula

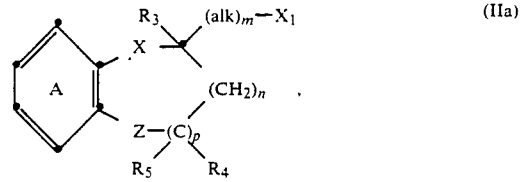
(IIa)

in which $X_1$ is reactive esterified hydroxy, with a compound of formula $H_2N-CH_2-CH_2-R_1$ (IVb) and reacting the resulting intermediate of formula

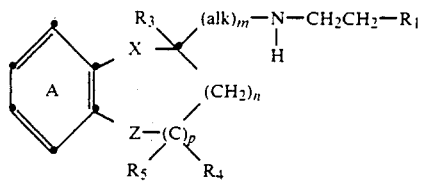
(IVc)

with acrolein or with a free or functionally modified aldehyde of formula $Y_1—CH_2—CH_2—CH=R_2'$ (IVd; $Y_1$ = reactive esterified hydroxy; $R_2'$ = oxo or imino).

In another preferred form of VAriant c), a compound of formula IV in which $Y_1$ and $R_1$ are lower alkoxycarbonyl, that is to say in which $Y_1$ is a group of formula $—C(Y_2)=R_2'$ wherein $R_2'$ is oxo and the removable radical $Y_2$ has a lower alkoxy group as etherified hydroxy, is cyclised to form the corresponding compound of formula I' in which $R_2'$ is oxo and $R_1$ is lower alkoxycarbonyl.

For the preparation of the last-mentioned starting compounds of formula IV it is possible to use as starting materials, for example, compounds of formula

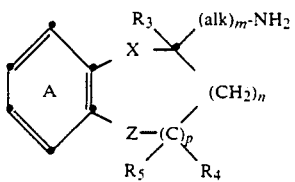
(IVe)

or salts thereof, which are obtainable, for example, by reduction of the corresponding nitriles, and to react them with at least 2 mols of a compound of formula

(IVf)

Variant d)

The C-acylation in accordance with the process can be effected especially in the presence of one of the bases mentioned under Variant a), but especially advantageously by means of a metal base, such as lithium diisopropylamine or n-butyllithium, optionally in the presence of chlorotrimethylsilane.

The reaction of a compound of formula

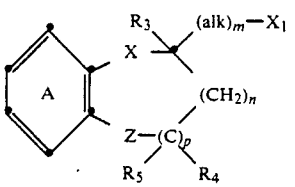
(IIa)

with a compound of formula

(Vc)

or with a salt thereof, analogously to the N-alkylation according to Variant a) in the presence of one of the bases mentioned, results in the starting material of formula Va.

Variant e)

Radicals $X_4$ that can be converted into free, etherified or acylated hydroxy or free or acylated amino $R_2$ are, for example, radicals that can be converted into such a group $R_2$ by solvolysis, that is to say by reaction with a corresponding compound of formula $R_2H$ or with a salt thereof, for example halogen atoms, for example chlorine, bromine or iodine. Radicals $X_4$ that can be converted into hydroxy $R_2$ are also diazonium groups, for example of formula $—N_2^\oplus A^\ominus$ in which $A^\ominus$ is the anion of a strong acid, such as a mineral acid, for example the chloride or sulfate ion.

The solvolysis is effected in customary manner, for example in the presence of a base, such as an alkali metal or alkaline earth metal hydroxide, for example sodium or potassium hydroxide, or a tertiary nitrogen base, for example a tri-lower alkylamine, such as triethylamine, or a heteroaromatic nitrogen base, such as pyridine, or a quaternary ammonium hydroxide, such as benzyltrimethylammonium hydroxide, or by using the compound $R_2H$ in the form of a metal salt, for example of formula $R_2^\ominus M^\oplus$ in which $M^\oplus$ is an alkali metal cation, such as the sodium ion. The operation is advantageously carried out in the presence of a solvent or diluent, for example in an excess of the reactant $R_2H$ and/or in an inert solvent that is miscible with the latter, if necessary with cooling or heating, for example in a temperature range of approximately from 0° to 120° C., and/or under inert gas, such as nitrogen.

The solvolysis of radicals $X_4$ to free, etherified or acylated hydroxy or free or acylated amino $R_2$ can optionally be combined with the solvolytic conversion of solvolysable groups $R_1$ into other groups $R_1$ according to the invention; for example, in the ammonolysis of radicals $X_4$ to amino $R_2$, lower alkoxycarbonyl groups $R_1$ or other groups $R_1$ that can be solvolysed to carbamoyl $R_1$ can, if desired, be ammonolysed to form carbamoyl groups $R_1$ at the same time.

For the manufacture of starting compounds of formula VI and the salts thereof, for example compounds of formula IIa

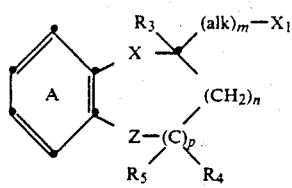
(IIa)

are used as starting materials and are reacted with a corresponding compound of formula

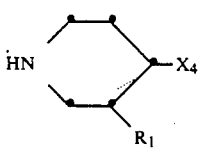
(VIa)

or a salt thereof, in the presence of one of the bases mentioned above, the operation being carried out, for example, in a manner analogous to that described under Process Variant a).

In a preferred form of the process, compounds of formula VI in which $X_4$ is halogen and the dotted line indicates the presence of a single bond between the carbon atoms carrying the substituents $R_1$ and $X_4$ and salts thereof are obtained by reacting a compound of formula I in which $R_2$ is hydroxy and the dotted line indicates the presence of a single bond between the carbon atoms carrying the substituents $R_1$ and $R_2$, or a salt thereof, with a halogenating agent, such as phosphorus trichloride or pentachloride or thionyl chloride, it being possible to obtain the corresponding compounds of formula I and their salts, for example, in a manner analogous to that described under Process Variant a) or c).

Variant f)

The anion $A^\ominus$ is, for example, the anion of a strong protonic acid, for example a halide ion, such as a chloride, bromide or iodide ion, or a sulfonate ion, such as an unsubstituted or substituted lower alkane- or benzene-sulfonate ion, for example the methanesulfonate, ethanesulfonate or p-bromophenylsulfonate or p-toluenesulfonate ion. Protected hydroxy is, for example, silyloxy, such as tri-lower alkylsilyloxy, for example trimethylsilyloxy, but may also be triphenyl-lower alkoxy, for example trityloxy. Protected amino is, for example, silylamino, such as tri-lower alkylsilylamino, for example trimethylsilylamino, but may also be phenyl-, diphenyl- or triphenyl-lower alkylamino, such as benzylamino, diphenylmethylamino or tritylamino. Etherified hydroxymethyl is, for example, lower alkoxymethyl, such as methoxy- or ethoxy-methyl, or unsubstituted or substituted phenyl-lower alkoxymethyl, for example phenyl-$C_1$-$C_4$alkoxymethyl substituted in the phenyl moiety, such as benzyloxy-, p-chlorobenzyloxy-, 1-phenylethoxy- or 1-(p-bromophenyl)-n-butoxymethyl. Protected hydroxymethyl is, for example, silyloxymethyl, such as tri-lower alkylsilyloxy-, for example trimethylsilyloxy-methyl, but may also be triphenyl-lower alkoxy-, for example trityloxy-methyl.

The process variant f) is especially suitable for the preparation of a compound of formula I or a tautomer and/or salt thereof, in which either $R_1$ is carboxy, lower alkoxycarbonyl, amidated carboxy or hydroxymethyl and $R_2$ is hydrogen, hydroxy or amino, or $R_1$ is hydrogen and $R_2$ is carboxy, lower alkoxycarbonyl, amidated carboxy or hydroxymethyl.

The reduction of the excess double bonds is effected by treatment with a suitable reducing agent, for example by hydrogenation in the presence of a hydrogenation catalyst, by reduction with a hydride-transfer reagent or by reduction with a metallic reduction system consisting of metal and a proton-removing agent.

Hydrogenation catalysts that come into consideration are, for example, elements of sub-group VIII of the Periodic Table of Elements or derivatives thereof, such as palladium, platinum, platinum oxide, ruthenium, rhodium, tris(triphenylphosphane)rhodium(I) halide, for example the chloride, or Raney nickel, which are optionally supported on a carrier, such as activated carbon, an alkali metal carbonate or sulfate, or a silica gel. Suitable hydride-transfer reagents are, for example, suitable light metal hydrides, especially alkali metal aluminium hydrides or borohydrides, such as lithium aluminium hydride, lithium triethylborohydride, sodium borohydride, sodium cyanoborohydride, or tin hydrides, such as triethyl- or tributyl-tin hydride, or diborane. The metal component of the metallic reduction system is, for example, a base metal, such as an alkali metal or alkaline earth metal, for example lithium, sodium, potassium, magnesium or calcium, or a transition metal, for example zinc, tin, iron or titanium, whilst suitable proton-removing agents are, for example, protonic acids of the kind mentioned above, such as hydrochloric or acetic acid, lower alkanols, such as ethanol, and/or amines or ammonia. Such systems are, for example, sodium/ammonia, zinc/hydrochloric acid, zinc/acetic acid or zinc/ethanol.

If $R_1''$ is other than $R_1$ and/or $R_2''$ is other than $R_2$, the conversion of $R_1''$ into $R_1$ and/or $R_2''$ into $R_2$, that is to say the removal of the protecting groups, i.e. the freeing of the corresponding radicals $R_1$ and/or $R_2$, is effected in the same or in a subsequent reaction step, the operation being carried out in the usual way, for example in the manner described following process variant g).

The preparation of starting compounds of formula VII is effected, for example, by reacting compounds of formula

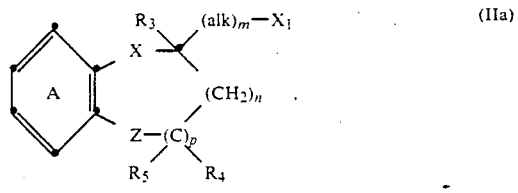
(IIa)

in which $X_1$ is reactive esterified hydroxy corresponding in its single negatively charged form to the anion $A^\ominus$, with compounds of formula

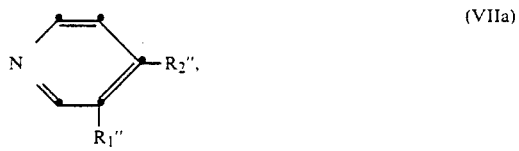
(VIIa)

or with a salt thereof, the operation being carried out, for example, in a manner analogous to that described under Process Variant a).

Variant g)

Removable radicals $Y_2$ in compounds VIII are, for example, reactive esterified hydroxy groups, such as hydroxy esterified by a strong inorganic acid or organic sulfonic acid, for example halogen, such as chlorine, bromine or iodine, sulfonyloxy, such as hydroxysulfonyloxy, halosulfonyloxy, for example fluorosulfonyloxy, lower alkanesulfonyloxy that is unsubstituted or substituted, for example, by halogen, for example methane- or trifluoromethanesulfonyloxy, cycloalkanesulfonyloxy, for example cyclohexanesulfonyloxy, or benzenesulfonyloxy that is unsubstituted or substituted, for example, by lower alkyl or by halogen, for example p-bromophenyl- or p-toluene-sulfonyloxy, or etherified hydroxy groups, for example lower alkoxy or unsubstituted or substituted phenyl-lower alkoxy.

The cyclisation can be carried out, for example, in the presence of one of the bases mentioned under Variant a), especially in the presence of an alkali metal lower alkanolate, for example with sodium methanolate or ethanolate.

The starting materials VIII are obtained, for example, by reacting a compound of formula

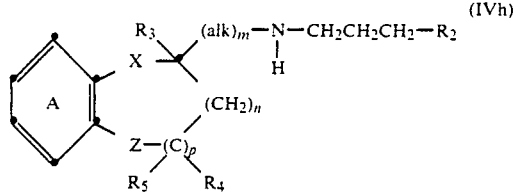

(IVh)

or a salt thereof with a compound of formula Y$_2$—CH$_2$—CH(Y$_2$)—R$_1$ (IVi).

In the starting materials of formulae IIb, III, IIIa, IV, IVg, VII and VIIa, a hydroxy group R$_2$ may be in etherified form and a hydroxy or amino group R$_2$ may also be in intermediately protected form, just as a hydroxymethyl group R$_1$ or R$_2$ in compounds IIb, IVi, Vb, VI, VIa, VII, VIIa and VIII may be in etherified or intermediately protected form. Protected hydroxy is, for example, silyloxy, such as tri-lower alkylsilyloxy, for example trimethylsilyloxy, but may also be triphenyl-lower alkoxy, for example trityloxy. Protected amino is, for example, silylamino, such as tri-lower alkylsilylamino, for example trimethylsilylamino, but may also be phenyl-, diphenyl- or triphenyl-lower alkylamino, such as benzylamino, diphenylmethylamino or tritylamino. Etherified hydroxymethyl is, for example, lower alkoxymethyl, such as methoxy- or ethoxymethyl, or unsubstituted or substituted phenyl-lower alkoxymethyl, for example phenyl-C$_1$–C$_4$alkoxymethyl substituted in the phenyl moiety, such as benzyloxy-, p-chlorobenzyloxy-, 1-phenylethoxy- or 1-(p-bromophenyl)-n-butoxy-methyl. Protected hydroxymethyl is, for example, silyloxymethyl, such as tri-lower alkylsilyloxy-, for example trimethylsilyloxy-methyl, but may also be triphenyl-lower alkoxy-, for example trityloxy-methyl.

The freeing of etherified and intermediately protected, respectively, radicals R$_1$ and R$_2$, that is to say the removal of the intermediate protecting groups, is effected in customary manner, for example by solvolysis, such as mild hydrolysis, for example treatment with water under neutral or weakly acidic conditions, for example by the action of dilute aqueous mineral or carboxylic acids, for example dilute hydrochloric or acetic acid. The freeing of intermediately protected hydroxy and amino groups R$_2''$ and of etherified or protected hydroxymethyl groups R$_1$41 R in starting materials of formulae VII and VIIa is effected in analogous manner.

Compounds of formula I obtainable according to the process or by other means can be converted in customary manner into other compounds of formula I.

For example, esterified or amidated carboxy groups R$_1$ and R$_2$ can be hydrolysed to carboxy R$_1$ and R$_2$ in customary manner, for example in the presence of a basic or acidic hydrolysis agent, such as an alkali metal hydroxide or carbonate, for example sodium hydroxide or potassium carbonate, or a mineral acid, for example hydrochloric acid or sulfuric acid. Esterified carboxy groups R$_1$ and R$_2$ can also be converted into other esterified carboxy groups R$_1$ and R$_2$ by transesterification, that is to say treatment with an alcohol in the presence of an acidic or basic solvolysis agent, such as a mineral acid, for example sulfuric acid, or a corresponding alkali metal alcoholate or an alkali metal hydroxide, or converted into amidated carboxy R$_1$ and R$_2$ by reaction with ammonia or with a corresponding amine having at least one hydrogen atom.

Free carboxy R$_1$ and R$_2$ can be converted into esterified carboxy R$_1$ and R$_2$ in customary manner, for example by treatment with a corresponding alcohol in the presence of a mineral acid, for example sulfuric acid, or by conversion into a halide and subsequent reaction with a corresponding alcohol, for example in the presence of pyridine or triethylamine, or by conversion into an alkali metal salt and subsequent reaction with a reactive ester of the corresponding alcohol, such as a corresponding halide. Likewise, a carboxy compound can be esterified with a corresponding alcohol using a dehydrating agent, such as N,N'-dicyclohexylcarbodiimide. Free or esterified carboxy R$_1$ and R$_2$ can also be converted into amidated carboxy R$_1$ and R$_2$ by reaction with ammonia or an amine having at least one hydrogen atom and dehydration of the intermediately formed ammonium salt, for example by heating or by means of a dehydrating agent, such as N,N'-dicyclohexylcarbodiimide, or by conversion into the halide and subsequent reaction with ammonia or with an amine having at least one hydrogen atom.

Furthermore, hydroxy groups which may be present can be esterified, for example converted by treatment with a lower alkanecarboxylic acid anhydride or halide into lower alkanoyloxy, or converted by reaction with a reactive ester, especially a hydrobromic or hydrochloric acid ester, of a lower alkanol into corresponding etherified hydroxy. Conversely, the hydroxy group may be freed from esterified or etherified hydroxy, such as lower alkanoyloxy or lower alkoxy, by solvolysis, preferably under acidic conditions. In an analogous manner, it is also possible to hydrolyse etherified or acylated hydroxy R$_2$ to hydroxy.

In corresponding manner, furthermore hydroxymethyl R$_1$ and R$_2$ can be esterified, for example converted by treatment with a lower alkanecarboxylic acid anhydride or halide into lower alkanoyloxymethyl R$_1$ and R$_2$. Conversely, the hydroxy group may be freed from acylated hydroxymethyl R$_1$ and R$_2$, for example lower alkanoyloxymethyl, by solvolysis, preferably under acidic conditions.

Furthermore, hydroxymethyl R$_1$ and R$_2$ can be converted in customary manner into lower alkoxycarbonyl or amidated carboxy R$_1$ and R$_2$, the operation being carried out, for example, by first oxidising hydroxymethyl R$_1$ and R$_2$ to carboxy in customary manner, for example in the presence of an oxidising agent, such as potassium permanganate or potassium dichromate, and then converting the carboxy group into lower alkoxycarbonyl R$_1$ and R$_2$ in customary manner, for example by treatment with a corresponding alcohol in the presence of a mineral acid, for example sulfuric acid, or by conversion into a halide and subsequent reaction with a corresponding alcohol, for example in the presence of pyridine or triethylamine, or by conversion into an alkali metal salt and subsequent reaction with a reactive ester of the corresponding alcohol, such as a corresponding halide, or by using a dehydrating agent, such as N,N'-dicyclohexylcarbodiimide, with a corresponding alcohol, or converting the carboxy group into amidated carboxy R$_1$ and R$_2$ by reaction with ammonia or an amine having at least one hydrogen atom and dehydration of the intermediately formed ammonium salt, for example by heating or by means of a dehydrating agent, such as N,N'-dicyclohexylcarbodiimide, or by conversion into the halide and subsequent reaction with ammonia or with an amine having at least one hydrogen atom. It is also possible to convert acylated hydroxymethyl $R_1$ and $R_2$ into esterified or amidated carboxy $R_1$ and $R_2$ by first freeing the acylated hydroxymethyl group by solvolysis, for example in the manner described above, and then converting the resulting free hydroxymethyl group, in the manner described above, into a carboxy group and converting the latter further into an esterified or amidated carboxy group. Conversely, esterified or amidated carboxy groups $R_1$ and $R_2$ can be converted into free or acylated hydroxymethyl $R_1$ and $R_2$ by first hydrolysing the esterified or amidated carboxy group $R_1$ and $R_2$ to carboxy in customary manner, for example in the presence of a basic or acidic hydrolysis agent, such as an alkali metal hydroxide or carbonate, for example sodium hydroxide or potassium carbonate, or a mineral acid, for example hydrochloric acid or sulfuric acid, and then reducing the resulting carboxy group in customary manner, for example in the presence of a reducing agent, for example of the kind mentioned above, to hydroxymethyl $R_1$ and $R_2$ and then, if desired, converting the latter into acylated hydroxymethyl $R_1$ and $R_2$, for example in the manner described above.

In compounds of formula I in which the dotted line indicates the presence of a double bond between the carbon atoms carrying the substituents $R_1$ and $R_2$, that bond can be hydrogenated to a single bond, for example in a manner known per se using a reducing agent, for example of the kind mentioned under Variant f).

Furthermore, a compound of formula I in which the dotted line indicates the presence of a double bond between the carbon atoms carrying the substituents $R_1$ and $R_2$ and $R_2$ is hydrogen, can be converted into a corresponding piperidine compound, for example in a manner known per se by the addition of a compound $R_2$—H in which $R_2$ is a free, etherified or acylated hydroxy group or a free or acylated amino group. The addition is carried out especially in the presence of a suitable base, for example of the kind mentioned under Variant a).

Conversely, compounds of formula I in which the dotted line indicates the presence of a single bond between the carbon atoms carrying the substituents $R_1$ and $R_2$ can be converted in a manner known per se into corresponding tetrahydropyridine compounds in which $R_2$ is hydrogen, for example by elimination of a compound $R_2$—H in which $R_2$ is a free, etherified or acylated hydroxy group or a free or acylated amino group. Leaving groups $R_2$ that are less suitable for elimination, for example hydroxy, can first be converted, for example in situ, into more suitable leaving groups $R_2$, for example lower alkanesulfonyloxy, such as methanesulfonyloxy, or halogen, such as chlorine, bromine or iodine. The elimination is effected especially in the presence of a suitable base, for example of the kind mentioned under Variant a).

Salts of compounds of formula I and of their tautomers can be produced in a manner known per se. Thus, for example, acid addition salts of compounds of formula I are obtained by treatment with an acid or a suitable ion exchange reagent. Salts can be converted into the free compounds of formula I in customary manner; for example acid addition salts can be converted by treatment with a suitable basic agent.

Depending upon the procedure and reaction conditions, the compounds of formula I having salt-forming, especially basic, properties may be obtained in free form or in the form of salts.

As a result of the close relationship between the novel compound of formula I in free form and in the form of its salts, hereinbefore and hereinafter the free compound of formula I or its salts should be understood as meaning also the corresponding salts or the free compound of formula I, respectively, where appropriate and expedient.

The novel compounds of formula I, including salts of salt-forming compounds, can also be obtained in the form of their hydrates or may include other solvents, for example those used for the crystallisation of compounds in solid form.

Depending upon the starting materials and procedures chosen, the novel compounds of formula I may be in the form of one of the possible isomers or in the form of a mixture thereof. Depending upon the molecular symmetry, for example depending upon the number and the absolute and relative configuration of the chiral centres, such as asymmetric carbon atoms, as pure isomers there may be obtained, for example, pure enantiomers and/or pure diastereoisomers, such as pure cis-/trans isomers or meso-compounds. Accordingly, as isomeric mixtures there may be obtained, for example, enantiomeric mixtures, such as racemates, diastereoisomeric mixtures or mixtures of racemates.

Resulting diastereoisomeric mixtures and mixtures of racemates can be separated into the pure diastereoisomers or racemates in known manner on the basis of the physico-chemical differences between the constituents, for example by fractional crystallisation.

Resulting enantiomeric mixtures, such as racemates, can be separated into the enantiomers by known methods, for example by recrystallisation from an optically active solvent, by chromatography on chiral adsorbents, with the aid of suitable microorganisms, by cleaving with specific, immobilised enzymes, by means of the formation of inclusion compounds, for example using chiral Crown ethers, in which case only one enantiomer is complexed, or by conversion into diastereoisomeric salts, for example by reaction of a basic end product racemate with an optically active acid, such as a carboxylic acid, for example tartaric or malic acid, or a sulfonic acid, for example camphorsulfonic acid, and separation of the mixture of diastereoisomers obtained in this manner, for example on the basis of their different solubilities, into the diastereoisomers from which the desired enantiomer can be freed by the action of suitable agents. Advantageously, the more active enantiomer is isolated.

The invention also relates to those forms of the process according to which a compound obtainable as intermediate at any stage of the process is used as starting material and the remaining steps are carried out, or a starting material is used in the form of a derivative or salt and/or its racemates or enantiomers or, especially, is formed under the reaction conditions.

In the process of the present invention it is preferable to use those starting materials which result in the compounds of formula I described at the beginning as being especially valuable. The invention relates also to novel starting materials which were developed specifically for the preparation of the compounds of formula I, to their use and to process for their preparation, the variables $R_1$, $R_2$, $R_3$, $R_4$, $R_5$, X, Z, m, n, p and alk and the substituents of the ring A and the dotted line having the meanings indicated for the groups of compounds of formulae I, IA and IB that are preferred in each case.

In this connection, special mention should be made of compounds of formula

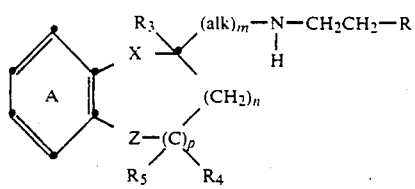
(IVc)

and their salts. These likewise have nootropic properties with a degree of action comparable to that of the corresponding compounds of formulae I and I' and can likewise be used as nootropic active ingredients in medicaments.

Accordingly, the invention relates also to pharmaceutical, especially nootropic, preparations containing as active ingredient a compound of the formula IVc in which $R_1$ represents carboxy, lower alkoxycarbonyl, carbamoyl, N-lower alkylcarbamoyl, N,N-di-lower alkylcarbamoyl or optionally acylated hydroxymethyl, $R_3$ represents hydrogen or lower alkyl, $R_4$ is lower alkyl, $R_5$ is lower alkyl, p is 0, m is 1, alk represents lower alkylene or lower alkylidene, the ring A is unsubstituted or is mono- or poly-substituted by hydroxy, lower alkoxy, lower alkanoyloxy, halogen, lower alkyl and/or by trifluoromethyl, and either each of X and Z represents an oxygen atom and n represents 1, or X represents a methylene group, Z represents an oxygen atom and n represents 1, or X represents an oxygen atom, Z represents a methylene group and n represents 1, or X represents a direct bond, Z represents an oxygen atom and n represents 2, or a pharmaceutically acceptable salt thereof, to the use of the mentioned compounds of the formula IVc or their pharmaceutically acceptable salts for the manufacture of nootropic pharmaceutical preparations, to a method for the treatment of the symptoms of cerebral insufficiency, characterised in that one of the mentioned compounds of the formula IVc, or a pharmaceutically acceptable salt thereof, is administered, and to compounds of the formula IVc in which $R_1$ represents carboxy, lower alkoxycarbonyl, carbamoyl, N-lower alkylcarbamoyl, N,N-di-lower alkylcarbamoyl or optionally acylated hydroxymethyl, $R_3$ represents hydrogen or lower alkyl, $R_4$ is lower alkyl, $R_5$ is lower alkyl, p is 0, m is 1, alk represents lower alkylene or lower alkylidene, the ring A is unsubstituted or is mono- or poly-substituted by hydroxy, lower alkoxy, lower alkanoyloxy, halogen, lower alkyl and/or by trifluoromethyl, and either each of X and Z represents an oxygen atom and n represents 1, or X represents a methylene group, Z represents an oxygen atom and n represents 1, or X represents an oxygen atom, Z represents a methylene group and n represents 1, or X represents a direct bond, Z represents an oxygen atom and n represents 2, with the proviso that in compounds of the formula IVc in which the ring A is unsubstituted, each of X and Z represents oxygen, n represents 1 and $R_3$ represents hydrogen, alk is other than methylene if $R_1$ represents carbamoyl or N-methyl-, N-ethyl-, N,N-dimethyl- or N,N-diethylcarbamoyl, and to their salts, and to a process for the manufacture of the latter, novel compounds of the formula IVc and their salts, and to compounds of formula IVc in which $R_1$ is carboxy, lower alkoxycarbonyl, amidated carboxy or free or acylated hydroxymethyl, $R_3$ is hydrogen or lower alkyl, $R_4$ is lower alkyl, $R_5$ is lower alkyl, alk is lower alkylene or lower alkylidene, the ring A is unsubstituted or is mono- or poly-substituted by hydroxy, lower alkoxy, lower alkanoyloxy, cyano, halogen, lower alkyl and/or by trifluoromethyl, m is 0 or 1, p is 1, Z is an oxygen atom, and in which either X is an oxygen atom or a methylene group and n is 0, or X is a direct bond and n is 1, and salts thereof, to the use of the said compounds of formula IVc, to a process for the preparation thereof, and to pharmaceutical preparations containing a compound of formula IVc or a pharmaceutically acceptable salt thereof.

Accordingly, the invention relates also especially to the groups of compounds of the formula IVc which are made up by the compounds of the formulae

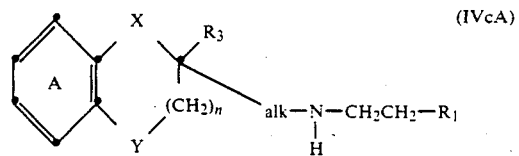
(IVcA)

and

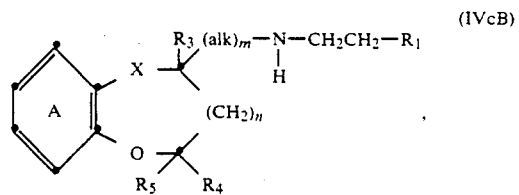
(IVcB)

that is to say, the invention relates also to pharmaceutical, especially nootropic, preparations containing as active ingredient a compound of the formula IVcA in which $R_1$ represents carboxy, lower alkoxycarbonyl, carbamoyl, N-lower alkylcarbamoyl, N,N-di-lower alkylcarbamoyl or optionally acylated hydroxymethyl, $R_3$ represents hydrogen or lower alkyl, alk represents lower alkylene or lower alkylidene, the ring A is unsubstituted or is mono- or poly-substituted by hydroxy, lower alkoxy, lower alkanoyloxy, halogen, lower alkyl and/or by trifluoromethyl, and either each of X and Y represents an oxygen atoms and n represents 1, or X represents a methylene group, Y represents an oxygen atom and n represents 1, or X represents an oxygen atom, Y represents a methylene group and n represents 1, or X represents a direct bond, Y represents an oxygen atom and n represents 2, or a pharmaceutically acceptable salt thereof, to the use of the mentioned compounds of the formula IVcA or their pharmaceutically acceptable salts for the manufacture of nootropic pharmaceutical preparations, to a method for the treatment of the symptoms of cerebral insufficiency, characterised in that one of the mentioned compounds of the formula IVcA, or a pharmaceutically acceptable salt thereof, is administered, and to compounds of the formula IVca in which $R_1$ represents carboxy, lower alkoxycarbonyl, carbamoyl, N-lower alkylcarbamoyl, N-N-di-lower alkylcarbamoyl or optionally acylated hydroxymethyl, $R_3$ represents hydrogen or lower alkyl, alk represents lower alkylene or lower alkylidene, the ring A is unsubstituted or is mono- or poly-substituted by hydroxy, lower alkoxy, lower alkanoyloxy, halogen, lower alkyl and/or by trifluoromethyl, and either each of X and Y represents an oxygen atom and n represents 1, or X represents a methylene group, Y represents an oxygen atom and n represents 1, or X represents an oxygen atom, Y represents a methylene group and n represents 1. or X represents a direct bond, Y represents an oxygen atom and n represents 2, with the proviso that in compounds of the formula IVcA in which the ring A is unsubstituted, each of X and Y represents oxygen, n represents 1 and $R_3$ represents hydrogen, alk is other than methylene if $R_1$ represents carbamoyl or N-methyl-, N-ethyl-, N,N-dimethyl- or N,N-diethylcarbamoyl, and to their salts, and to a process for the manufacture of the latter, novel compounds of the formula IVcA and their salts, and to compounds of the formula IVcB in which $R_1$ is carboxy, lower alkoxycarbonyl, amidated carboxy or free or acylated hydroxymethyl, $R_3$ is hydrogen or lower alkyl, $R_4$ is lower alkyl, $R_5$ is lower alkyl, alk is lower alkylene or lower alkylidene, the ring A is unsubstituted or is mono- or poly-substituted by hydroxy, lower alkoxy, lower alkanoyloxy, cyano, halogen, lower alkyl and/or by trifluoromethyl, m is 0 or 1. and in which either X is an oxygen atom or a methylene group and n is 0, or X is a direct bond and n is 1, and salts thereof, to the use of the said compounds of formula IVcB, to a process for the preparation thereof, and to pharmaceutical preparations containing a compound of formula IVcB or a pharmaceutically acceptable salt thereof.

Accordingly, the invention relates, for example, also to pharmaceutical, especially nootropic, preparations containing as active ingredient a compound of the formula IVcA in which $R_1$ represents carboxy, lower alkoxycarbonyl, carbamoyl, N-lower alkylcarbamoyl or N,N-di-lower alkylcarbamoyl, $R_3$ represents hydrogen or lower alkyl, alk represents lower alkylene or lower alkylidene, the ring A is unsubstituted or is mono- or poly-substituted by hydroxy, lower alkoxy, lower alkanoyloxy, halogen, lower alkyl and/or by trifluoromethyl, X represents an oxygen atom or a methylene group, Y represents an oxygen atom and n represents 1, or a pharmaceutically acceptable salt thereof, to the use of the mentioned compounds of the formula IVcA or their pharmaceutically acceptable salts for the manufacture of nootropic pharmaceutical preparations, to a method for the treatment of the symptoms of cerebral insufficiency, characterised in that one of the mentioned compounds of the formula IVcA or a pharmaceutically acceptable salt thereof, is administered, and to compounds of the formula IVcA in which $R_1$ represents carboxy, lower alkoxycarbonyl, carbamoyl, N-lower alkylcarbamoyl or N,N-di-lower alkylcarbamoyl, $R_3$ represents hydrogen or lower alkyl, alk represents lower alkylene or lower alkylidene, the ring A is unsubstituted or is mono- or poly-substituted by hydroxy, lower alkoxy, lower alkanoyloxy, halogen, lower alkyl and/or by trifluoromethyl, X represents an oxygen atom or a methylene group, Y represents an oxygen atom and n represents 1, with the proviso that in compounds of the formula IVcA in which the ring A is unsubstituted, each of X and Y represents oxygen, n represents 1 and $R_3$ represents hydrogen, alk is other than methylene if $R_1$ represents carbamoyl or N-methyl-, N-ethyl-, N,N-di-methyl-, or N,N-diethyl-carbamoyl, and to their salts, and to a process for the manufacture of the latter, novel compounds of the formula IVcA and their salts.

The variables in the formula IVc have, for example, the preferred meanings given under formula I.

The invention relates in this respect especially to pharmaceutical, especially nootropic, preparations and to the manufacture thereof and to methods of treatment, characterised in that there is selected a compound of the formula IVcA in which $R_1$ represents carboxy, lower alkoxycarbonyl, carbamoyl, N-lower alkylcarbamoyl, N,N-di-lower alkylcarbamoyl, hydroxymethyl, lower alkanoyloxymethyl, lower alkanesulphonyloxymethyl, benzoyloxymethyl or pyridoyloxymethyl, $R_3$ represents hydrogen or lower alkyl, alk represents lower alkylene that links the ring system with the NH group shown in formula IVcA by up to and including 3 carbon atoms, or alk represents lower alkylidene, the ring A is unsubstituted or is mono-, di- or poly-substituted by hydroxy, lower alkoxy, lower alkanoyloxy, halogen, lower alkyl and/or by trifluoromethyl, and either each of X and Y represents an oxygen atom and n represents 1, or X represents a methylene group, Y represents an oxygen atom and n represents 1, or X represents an oxygen atom, Y represents a methylene group and n represents 1, or X represents a direct bond, Y represents an oxygen atom and n represents 2, or one of the pharmaceutically acceptable salts thereof, and to compounds of the formula IVcA in which $R_1$ represents carboxy, lower alkoxycarbonyl, carbamoyl, N-lower alkylcarbamoyl, N,N-di-lower alkylcarbamoyl, hydroxymethyl, lower alkanoyloxymethyl, lower alkanesulphonyloxymethyl, benzoyloxymethyl or pyridoyloxymethyl, $R_3$ represents hydrogen or lower alkyl, alk represents lower alkylene that links the ring system with the NH group shown in formula IVcA by up to and including 3 carbon atoms, or alk represents lower alkylidene, the ring A is unsubstituted or is mono-, di- or poly-substituted by hydroxy, lower alkoxy, lower alkanoyloxy, halogen, lower alkyl and/or by trifluoromethyl, and either each of X and Y represents an oxygen atom and n represents 1, or X represents a methylene group, Y represents an oxygen atom and n represents 1, or X represents an oxygen atom, Y represents a methylene group and n represents 1, or X represents a direct bond, Y represents an oxygen atom and n represents 2, with the proviso that in compounds of the formula IVcA in which the ring A is unsubstituted, each of X and Y represents oxygen, n represents 1 and $R_3$ represents hydrogen, alk is other than methylene if $R_1$ represents carbamoyl or N-methyl-, N-ethyl-, N,N-dimethyl-or N,N-diethyl-carbamoyl, and to their salts, and to a process for the manufacture of the latter, novel compounds of the formula IVcA and their salts, for example to pharmaceutical, especially nootropic, preparations and to the manufacture thereof and to methods of treatment, characterised in that there is selected a compound of the formula IVcA in which $R_1$ represents carboxy, lower alkoxycarbonyl, carbamoyl, N-lower alkylcarbamoyl or N,N-di-lower alkylcarbamoyl, $R_3$ represents hydrogen or lower alkyl, alk represents lower alkylene that links the ring system with the NH group shown in formula IVcA by up to and including 3 carbon atoms, or alk represents lower alkylidene, the ring A is unsubstituted or is mono-, di- or poly-substituted by hydroxy, lower alkoxy, lower alkanoyloxy, halogen, lower alkyl and/or by trifluoromethyl, X represents an oxygen atom or a methylene group, Y represents an oxygen atom and n represents 1, or one of the pharmaceutically acceptable salts thereof, and to compounds of the formula IVcA in which $R_1$ represents carboxy, lower alkoxycarbonyl, carbamoyl, N-lower alkylcarbamoyl or N,N-di-lower alkylcarbamoyl, $R_3$ represents hydrogen or lower alkyl, alk represents lower alkylene that links the ring system with the NH group shown in formula IVcA by up to and including 3 carbon atoms, or alk represents lower alkylidene, the ring A is unsubstituted or is mono-, di- or poly-substituted by hydroxy, lower alkoxy, lower alkanoyloxy, halogen, lower alkyl and/or by trifluoromethyl, X represents an oxygen atom or a methylene group, Y represents an oxygen atom and n represents 1, with the proviso that in compounds of the formula IVcA in which the ring A is unsubstituted, each of X and Y represents oxygen, n represents 1 and $R_3$ represents hydrogen, alk is other than methylene if $R_1$ represents carbamoyl or N-methyl-, N-ethyl-, N,N-dimethyl-or N,N-diethylcarbamoyl, and to their salts, and to a process for the manufacture of the latter, novel compounds of the formula IVcA and their salts.

In this respect the invention relates more especially to pharmaceutical, especially nootropic, preparations and to the manufacture thereof and to methods of treatment, characterised in that there is selected a compound of the formula IVcA in which $R_1$ represents carboxy, hydroxymethyl, $C_2$–$C_5$-alkanoyloxymethyl, such as acetoxymethyl, $C_1$–$C_4$-alkoxycarbonyl, such as methoxycarbonyl, or carbamoyl, $R_3$ represents hydrogen or $C_1$–$C_4$-alkyl, such as methyl, alk represents $C_1$–$C_4$-alkylene that links the ring system with the NH group shown in formula IVcA by up to and including 3 carbon atoms, such as methylene or ethylene, the ring A is unsubstituted or is substituted, especially in the 7-position, by $C_1$–$C_4$-alkoxy, such as methoxy, and either each of X and Y represents an oxygen atom and n represents 1, or X represents a methylene group, Y represents an oxygen atom and n represents 1, or X represents an oxygen atom, Y represents a methylene group and n represents 1, or X represents a direct bond, Y represents an oxygen atom and n represents 2, on one of the pharmaceutically acceptable salts thereof, and to compounds of the formula IVcA in which $R_1$ represents carboxy, hydroxymethyl, $C_2$–$C_5$-alkanoyloxymethyl, such as acetoxymethyl, $C_1$–$C_4$-alkoxycarbonyl, such as methoxycarbonyl, or carbamoyl, $R_3$ represents hydrogen or $C_1$–$C_4$-alkyl, such as methyl, alk represents $C_1$–$C_4$-alkylene that links the ring system with the NH group shown in formula IVcA by up to and including 3 carbon atoms, such as methylene or ethylene, the ring A is unsubstituted or is substituted, especially in the 7-position, by $C_1$–$C_4$-alkoxy, such as methoxy, and either each of X and Y represents an oxygen atom and n represents 1, or X represents a methylene group, Y represents an oxygen atom and n represents 1, or X represents an oxygen atom, Y represents a methylene group and n represents 1, or X represents a direct bond, Y represents an oxygen atom and n represents 2, with the proviso that in compounds of the formula IVcA in which the ring A is unsubstituted, each of X and Y represents oxygen, n represents 1 and $R_3$ represents hydrogen, alk is other than methylene if $R_1$ represents carbamoyl, and to their salts, and to a process for the manufacture of the latter, novel compounds of the formula IVcA and their salts, for example pharmaceutical, especially to nootropic, preparations and to the manufacture thereof, and to methods of treatment, characterised in that there is selected a compound of the formula IVcA in which $R_1$ represents $C_1$–$C_4$-alkoxycarbonyl, such as methoxycarbonyl, $R_3$ represents hydrogen or $C_1$–$C_4$-alkyl, such as methyl, alk represents $C_1$–$C_4$-alkylene that links the ring system with the NH group shown in formula IVcA by up to and including 3 carbon atoms, such as methylene or ethylene, the ring A is unsubstituted, X represents an oxygen atom or a methylene group, Y represents an oxygen atom and n represents 1, or one of the pharmaceutically acceptable salts thereof, and to compounds of the formula IVcA in which $R_1$ represents $C_1$–$C_4$-alkoxycarbonyl, such as methoxycarbonyl, $R_3$ represents hydrogen or $C_1$–$C_4$-alkyl, such as methyl, alk represents $C_1$–$C_4$-alkylene that links the ring system with the NH group shown in formula IVcA by up to and including 3 carbon atoms, such as methylene or ethylene, the ring A is unsubstituted, X represents an oxygen atom or a methylene group, Y represents an oxygen atom and n represents 1, and to their salts, and to a process for the manufacture of the latter, novel compounds of the formula IVcA and their salts.

In this respect the invention relates most especially to pharmaceutical, especially nootropic, preparations and to the manufacture thereof, and to methods of treatment, characterised in that there is selected a compound of the formula IVcA in which $R_1$ represents $C_1$–$C_4$-alkoxycarbonyl, such as methoxycarbonyl, $R_3$ represents hydrogen, alk represents methylene or ethylene, the ring A is unsubstituted, X represents an oxygen atom or a methylene group, Y represents an oxygen atom and n represents 1, or one of the pharmaceutically acceptable salts thereof, and to compounds of the formula IVcA in which $R_1$ represents $C_1$–$C_4$-alkoxycarbonyl, such as methoxycarbonyl, $R_3$ represents hydrogen, alk represents methylene or ethylene, the ring A is unsubstituted, X represents an oxygen atom or a methylene group, Y represents an oxygen atom and n represents 1, and to their salts, and to a process for the manufacture of the latter, novel compounds of the formula IVcA and their salts.

In this respect the invention relates especially to compounds of formula IVcB in which $R_1$ is carboxy, lower alkoxycarbonyl, carbamoyl, N-lower alkylcarbamoyl, N,N-di-lower alkylcarbamoyl, N,N-lower alkylenecarbamoyl, N,N-(aza)-, N,N-(oxa)- or N,N-(thia)-lower alkylenecarbamoyl, hydroxymethyl, lower alkanoyloxymethyl, lower alkanesulfonyloxymethyl, benzoyloxymethyl or pyridoyloxymethyl, $R_3$ is hydrogen or lower alkyl, $R_4$ is lower alkyl, $R_5$ is lower alkyl, alk is lower alkylene that links the ring system with the NH group shown in formula IVcB by up to and including 3 carbon atoms or is lower alkylidene, the ring A is unsubstituted or is mono-, di- or poly-substituted by hydroxy, lower alkoxy, lower alkanoyloxy, cyano, halogen, lower alkyl and/or by trifluoromethyl, m is 0 or 1, and in which either X is an oxygen atom or a methylene group and n is 0, or X is a direct bond and n is 1, and salts thereof.

In this respect the invention relates more especially to compounds of formula IVcB in which $R_1$ is $C_1$–$C_4$alkoxycarbonyl, such as methoxycarbonyl or ethoxycarbonyl, carbamoyl, N,N-lower alkylenecarbamoyl, such as piperidinocarbonyl, N,N-(aza)-lower alkylenecarbamoyl, such as piperazinocarbonyl, N,N-(oxa)-lower alkylenecarbamoyl, such as morpholinocarbonyl, or N,N-(thia)-lower alkylenecarbamoyl, such as thiomorpholinocarbonyl, $R_3$ is hydrogen, $R_4$ is $C_1$–$C_4$alkyl, such as methyl, $R_5$ is $C_1$–$C_4$alkyl, such as methyl, alk is $C_1$–$C_4$alkylene that links the ring system with the NH group shown in formula IVcB by up to and including 3 carbon atoms, such as methylene or ethylene, the ring A is unsubstituted or is substituted, especially in the 6-position, by $C_1$–$C_4$alkoxy, such as methoxy, $C_1$–$C_4$alkyl, such as methyl, halogen having an atomic number of up to and including 35, such as fluorine or chlorine, cyano or by trifluoromethyl, m is 0 or 1, X is an oxygen atom or a methylene group and n is 0, and salts thereof.

In this respect the invention relates especially to compounds of formula IVcB in which $R_1$ is $C_1$-$C_4$alkoxycarbonyl, such as methoxycarbonyl or ethoxycarbonyl, or carbamoyl, $R_3$ is hydrogen, $R_4$ is $C_1$-$C_4$alkyl, such as methyl, $R_5$ is $C_1$-$C_4$alkyl, such as methyl, alk is $C_1$-$C_4$alkylene that links the ring system with the NH group shown in formula IVcB by up to and including 3 carbon atoms, such as methylene or ethylene, the ring A is unsubstituted or is monosubstituted, especially in the 6-position, by halogen having an atomic number of up to and including 35, such as fluorine or chlorine, m is 1, X is a methylene group and n is 0, and salts thereof.

In this respect the invention relates more especially to compounds of formula IVcB in which $R_1$ is $C_1$-$C_4$alkoxycarbonyl, such as methoxycarbonyl, or carbamoyl, $R_3$ is hydrogen, $R_4$ is $C_1$-$C_4$alkyl, such as methyl, $R_5$ is $C_1$-$C_4$alkyl, such as methyl, alk is ethylene, the ring A is unsubstituted, m is 1, X is a methylene group and n is 0, and salts thereof.

In this respect the invention relates specifically to pharmaceutical, especially nootropic, preparations and to the manufacture thereof and to methods of treatment, characterised in that there is selected one of the novel compounds of the formula IVc mentioned in the Examples, or one of the pharmaceutically acceptable salts thereof, and to the novel compounds of the formula IVc mentioned in the Examples and to their salts, and to processes for the manufacture of the latter, novel compounds of the formula IVc and their salts.

The present invention relates also to a process for the preparation of compounds of formula IVc or their salts, in which process, for example, h) compounds of the formulae

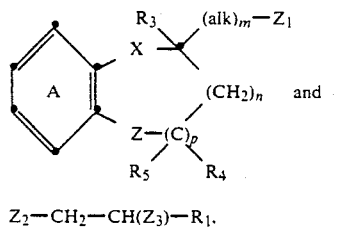

(VIIIa)

$Z_2-CH_2-CH(Z_3)-R_1$.  (VIIIb)

in which one of the radicals $Z_1$ and $Z_2$ is reactive esterified hydroxy, the other is amino and $Z_3$ is hydrogen, or $Z_1$ is amino and $Z_2$ and $Z_3$ together are an additional bond, or optionally salts of these compounds, are reacted with one another, or i) in a compound of formula

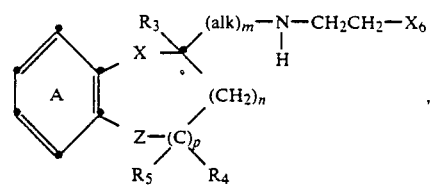

(IX)

in which $X_6$ is a radical that can be converted into $R_1$, or in a salt thereof, $X_6$ is converted into $R_1$, and, in the case of each of process variants h) and i), a protecting group which may be present is removed, and, if desired, a compound of formula IVc obtainable in accordance with the process or by other means is converted into a different compound of formula IVc, an isomeric mixture obtainable in accordance with the process is separated into the components, an enantiomeric or diastereoisomeric mixture obtainable in accordance with the process is separated into the enantiomers or diastereoisomers, respectively, and/or a free compound of formula IVc obtainable in accordance with the process is converted into a salt or a salt obtainable in accordance with the process is converted into the free compound of formula IVc or into a different salt.

Variant h)

Reactive esterified hydroxy $Z_1$ and $Z_2$ is especially hydroxy esterified by a strong inorganic acid or organic sulfonic acid, for example halogen, such as chlorine, bromine or iodine, sulfonyloxy, such as hydroxysulfonyloxy, halosulfonyloxy, for example fluorosulfonyloxy, lower alkanesulfonyloxy that is unsubstituted or substituted, for example by halogen, for example methane- or trifluoromethane-sulfonyloxy, cycloalkanesulfonyloxy, for example cyclohexanesulfonyloxy, or benzenesulfonyloxy that is unsubstituted or substituted, for example, by lower alkyl or by halogen, for example p-bromophenyl- or p-toluene-sulfonyloxy.

The reaction is in this case carried out especially in the presence of a condensation agent, such as a suitable base. Suitable bases are, for example, alkali metal hydroxides, hydrides, amides, alkanolates, carbonates, triphenylmethylides, di-lower alkylamides, amino-lower alkylamides or lower alkylsilylamides, or naphthaleneamines, lower alkylamines, basic heterocycles, ammonium hydroxides and carbocyclic amines. There may be mentioned by way of example: sodium hydroxide, hydride, amide or ethanolate, potassium tert.-butanolate or carbonate, lithium triphenylmethylide, lithium diisopropylamide, potassium 3-(aminopropyl)-amide or bis-(trimethylsilyl)-amide, or dimethylaminonaphthalene, di- or triethylamine, pyridine, benzyltrimethylammonium hydroxide, 1,5-diazabicyclo[4.3.0]non-5-ene (DBN) and 1,5-diazabicyclo[5.4.0]undec-5-ene (DBU). The reaction of amines VIIIa ($Z_1$=amino) with acrylic acid compounds VIIIb ($Z_2+Z_3$=bond) is effected, for example, with heating, for example at approximately 60°-120° C.

The starting materials of formulae VIIIa and VIIIb are known or can be prepared analogously to known processes.

Variant i)

A radical $X_6$ that can be converted into $R_1$ is, for example, functionally modified carboxy other than $R_1$, such as cyano, anhydridised carboxy, unsubstituted or substituted amidino, free, esterified or anhydridised carboximidoyl, esterified or amidated carboxy other than esterified or amidated carboxy $R_1$, tri-lower alkoxymethyl or trihalomethyl.

Anhydridised carboxy is, for example, carboxy anhydridised with a mineral acid, such as a hydrohalic acid, or with a carboxylic acid, such as an unsubstituted or substituted lower alkanoic or benzoic acid, or with a carbonic acid halide lower alkyl semiester. Examples that may be mentioned are halocarbonyl, such as chlorocarbonyl, lower alkanoyloxycarbonyl, such as acetoxycarbonyl, or lower alkoxycarbonyloxycarbonyl, such as ethoxycarbonyloxycarbonyl.

Substituted amidino is, for example, amidino substituted by an aliphatic radical, for example lower alkyl, such as lower alkylamidino, for example ethylamidino.

Esterified or anhydridised carboximidoyl is to be understood as being, for example, alkoxy- or halo-carboximidoyl, for example lower alkoxy-, such as ethoxy-, or chloro-carboximidoyl.

Tri-lower alkoxy- or tri-halo-methyl is, for example, trimethoxymethyl or trichloromethyl, respectively.

$X_6$ can be converted into $R_1$, for example, by solvolysis. Solvolysis agents are, for example, water, lower alkanols corresponding to the desired esterified carboxy $R_1$, ammonia, or amines corresponding to the desired amidated carboxy group $R_1$. The treatment with a corresponding solvolysis agent is optionally carried out in the presence of an acid or base. Suitable acids are, for example, inorganic or organic protonic acids, such as mineral acids, for example sulfuric acid or a hydrohalic acid, for example hydrochloric acid, sulfonic acids, for example lower alkanesulfonic acid or unsubstituted or substituted benzenesulfonic acid, for example methane- or p-toluene-sulfonic acid, or carboxylic acids, for example lower alkanecarboxylic acids, for example acetic acid, whilst bases that may be used are, for example, those mentioned under Variant h), especially sodium or potassium hydroxide.

In the solvolysis, the cyano group, anhydridised carboxy, unsubstituted or substituted amidino, free, esterified or anhydridised carboximidoyl, esterified or amidated carboxy other than esterified or amidated carboxy $R_1$, tri-lower alkoxymethyl or trihalomethyl is hydrolysed to carboxy. Lower alkanoyloxy radicals which may be present at the ring A may also be hydrolysed to hydroxy in the course of the hydrolysis.

Cyano, anhydridised carboxy, and esterified or amidated carboxy other than esterified or amidated carboxy $R_1$ are alcoholysed, for example with a suitable lower alkanol, to esterified carboxy $R_1$, and cyano and anhydridised carboxy are ammonolysed or aminolysed, for example with ammonia or with an amine corresponding to the amidated carboxy $R_1$.

The starting material of formula IX can be obtained, for example, by reaction of compounds of the formulae

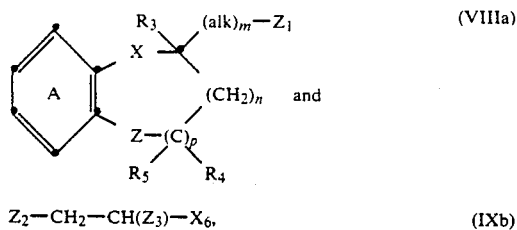

$$Z_2-CH_2-CH(Z_3)-X_6, \quad \text{(IXb)}$$

in which one of the radicals $Z_1$ and $Z_2$ is reactive esterified hydroxy, the other is amino and $Z_3$ is hydrogen, or $Z_1$ is amino and $Z_2$ and $Z_3$ together are an additional bond, or optionally salts of these compounds, the operation being carried out in a manner analogous to that described under Process Variant h), for example in the presence of a basic agent. Reactive esterified hydroxy $Z_1$ and $Z_2$ has, for example, one of the meanings given under Process Variant h).

In the starting materials of formula VIIIb, a hydroxymethyl group $R_1$ may be in etherified or intermediately protected form. Etherified hydroxymethyl is, for example, lower alkoxymethyl, such as methoxy- or ethoxymethyl, or unsubstituted or substituted phenyl-lower alkoxymethyl, for example phenyl-$C_1$-$C_4$alkoxymethyl substituted in the phenyl moiety, such as benzyloxy-, p-chlorobenzyloxy-, 1-phenylethoxy- or 1-(p-bromophenyl)-n-butoxy-methyl. Protected hydroxymethyl is, for example, silyloxymethyl, such as tri-lower alkylsilyloxy-, for example trimethylsilyloxy-methyl, but may also be triphenyl-lower alkoxy-, for example trityloxy-methyl.

The freeing of intermediately protected radicals $R_1$, that is to say the removal of the intermediate protecting groups, is effected in customary manner, for example by solvolysis, such as mild hydrolysis, for example treatment with water under neutral or weakly acidic conditions, for example by the action of dilute aqueous mineral or carboxylic acids, for example dilute hydrochloric or acetic acid.

Subsequent operations which may, if desired, be carried out on compounds of formula IVc obtained in accordance with the process or by other means are especially conversions of $R_1$ and of substituents of the ring A, separations of enantiomers and diastereoisomers and conversions into one another of salts and free compounds of formula IVc, analogous to those indicated for the compounds of formula I and are carried out in analogous manner.

The invention relates also to the use of compounds of formula I and IVc and, where appropriate, their tautomers and/or pharmaceutically acceptable salts of such compounds having salt-forming properties, especially as pharmacological, more especially nootropically active, active ingredients. They can be used, preferably in the form of pharmaceutically acceptable preparations, in a method for the prophylactic and/or therapeutic treatment of the animal or human body, especially as nootropics, for example for the treatment of the symptoms of cerebral insufficiency, especially memory disorders.

The invention relates also to pharmaceutical preparations that contain as active ingredient a compound of formula I or IVc, or, where appropriate, a tautomer and/or pharmaceutically acceptable salt thereof, and to processes for their preparation.

The pharmaceutical preparations according to the invention, which contain a compound of formula I or IVc or, where appropriate, a tautomer and/or pharmaceutically acceptable salt thereof, are for enteral, such as oral, and also rectal, and parenteral administration to warm-blooded animals, the preparations containing the pharmacological active ingredient alone or together with customary pharmaceutical adjuncts.

The novel pharmaceutical preparations contain, for example, from approximately 10% to approximately 80%, preferably from approximately 20% to approximately 60%, active ingredient. Pharmaceutical preparations according to the invention for enteral or parenteral administration are, for example, those in dosage unit forms, such as dragées, tablets, capsules or suppositories, and also ampoules. They are manufactured in a manner known per se, for example by means of conventional mixing, granulating, confectioning, dissolving or lyophilising processes. Thus, pharmaceutical preparations for oral use can be obtained by combining the active ingredient with solid carriers, optionally granulating the resulting mixture, and processing the mixture or granulate, if desired or necessary after the addition of suitable adjuncts, to form tablets or dragée cores.

Suitable carriers are especially fillers, such as sugars, for example lactose, saccharose, mannitol or sorbitol, cellulose preparations and/or calcium phosphate, for example tricalcium phosphate or calcium hydrogen phosphate, also binders such as starch pastes using, for example, corn, wheat, rice or potato starch, gelatine, tragacanth, methylcellulose and/or polyvinylpyrrolidone, if desired, disintegrators, such as the above-mentioned starches, also carboxymethyl starch, cross-linked polyvinylpyrrolidone, agar, alginic acid or a salt thereof, such as sodium alginate. Adjuncts are especially flow-regulating agents and lubricants, for example silica, talc, stearic acid or salts thereof, such as magnesium or calcium stearate, and/or polyethylene glycol. Dragée cores are provided with suitable coatings which may be resistant to gastric juices, there being used, inter alia, concentrated sugar solutions which may contain gum arabic, talc, polyvinylpyrrolidone, polyethylene glycol and/or titanium dioxide, or lacquer solutions in suitable organic solvents or solvent mixtures, or, for the production of coatings resistant to gastric juices, solutions of suitable cellulose preparations, such as acetylcellulose phthalate or hydroxypropylmethylcellulose phthalate. Colourings or pigments may be added to the tablets or dragée coatings, for example for identification purposes or to indicate different doses of active ingredient.

Further orally administrable pharmaceutical preparations are dry-filled capsules consisting of gelatine, and also soft, sealed capsules consisting of gelatine and a plasticiser, such as glycerol or sorbitol. The dry-filled capsules may contain the active ingredient in the form of a granulate, for example in admixture with fillers, such as lactose, binders, such as starches, and/or glidants, such as talc or magnesium stearate, and optionally stabilisers. In soft capsules, the active ingredient is preferably dissolved or suspended in suitable liquids, such as fatty oils, paraffin oil or liquid polyethylene glycols, to which stabilisers may likewise be added.

There come into consideration as rectally administrable pharmaceutical preparations, for example, suppositories that consist of a combination of the active ingredient and a suppository base. Suitable suppository bases are, for example, natural or synthetic triglycerides, paraffin hydrocarbons, polyethylene glycols or higher alkanols. It is also possible to use gelatine rectal capsules that contain a combination of the active ingredient and a base material. Suitable base materials are, for example, liquid triglycerides, polyethylene glycols or paraffin hydrocarbons.

Suitable for parenteral administration are especially aqueous solutions of an active ingredient in water-soluble form, for example a water-soluble salt, and also suspensions of the active ingredient, such as corresponding oily injection suspensions, there being used suitable lipophilic solvents or vehicles, such as fatty oils, for example sesame oil, or synthetic fatty acid esters, for example ethyl oleate or triglycerides, or aqueous injection suspensions that contain viscosity-increasing substances, for example sodium carboxymethylcellulose, sorbitol and/or dextran and, optionally, also stabilisers.

The dosage of the active ingredient can depend upon various factors, such as the method of administration, the species of warm-blooded animal, age and/or individual condition. In normal cases, the approximate daily dose for a warm-blooded animal weighing about 75 kg is estimated to be, in the case of oral administration, from approximately 20 mg to approximately 500 mg, especially from approximately 25 mg to approximately 250 mg, advantageously in several equal partial doses.

The following Examples illustrate the invention described above but are not intended to limit the scope thereof in any way. Temperatures are given in degrees Celsius.

As a result of the close relationship between a compound of formula I and the corresponding tautomeric compound of formula I', in the Examples a compound of formula I should be understood as meaning also the tautomeric compound of formula I' where appropriate and expedient. The same applies to a compound of formula I' and to salts of compounds of formulae I and I'.

EXAMPLE 1

First 5.55 g (25 mmol) of 1,2,5,6-tetrahydropyridine-3-carboxylic acid methyl ester hydrobromide (guvacoline hydrobromide) and then 11.31 g (87.5 mmol) of N-ethyl-N,N-diisopropylamine are added to a solution of 7.96 g (25 mmol) of 3-(p-toluenesulphonyloxymethyl)chroman in 100 ml of dimethylformamide. The mixture is stirred for 15 hours at 50° and then concentrated by evaporation under a high vacuum. Water is added to the residue and extraction is carried out with diethyl ether. The organic phases are washed with water and extracted with 2N hydrochloric acid. The hydrochloric acid extracts are combined, rendered alkaline, while cold, with sodium hydroxide solution (30% strength) and extracted with dichloromethane. The combined organic phases are dried over sodium sulphate and concentrated by evaporation in vacuo. 5.92 g (83%) of 1-(chroman-3-ylmethyl)-1,2,5,6-tetrahydropyridine-3-carboxylic acid methyl ester are obtained in the form of a pale yellow oil. The 1-(chroman-3-ylmethyl)-1,2,5,6-tetrahydropyridine-3-carboxylic acid methyl ester hydrochloride produced therefrom using hydrochloric acid in diethyl ether melts at 158°–159° after crystallisation from methanol/diethyl ether.

3-(p-toluenesulphonyloxymethyl)chroman can be manufactured, for example, as follows:

At room temperature and while stirring, a solution of 50.0 g (260 mmol) of 3-methoxycarbonylchroman (U.S. Pat. No. 4,178,380) in 200 ml of absolute tetrahydrofuran is added dropwise within a period of 40 minutes to a suspension of 9.86 g (260 mmol) of lithium aluminium hydride in 300 ml of absolute diethyl ether. After stirring for 16 hours at room temperature, the reaction mixture is decomposed with 9.9 ml of water, 9.9 ml of sodium hydroxide solution (15% strength) and 30 ml of water. The precipitate formed is filtered off with suction and the filtrate is concentrated to dryness by evaporation in vacuo. The oily residue is dissolved in diethyl ether and the solution is washed with water, dried over sodium sulphate and concentrated to dryness by evaporation. 36.71 g (86%) of oily 3-hydroxymethylchroman, which crystallises from diethyl ether/pentane and melts at 60°–61°, are obtained.

46.14 g (242 mmol) of p-toluenesulphonyl chloride are added while stirring at room temperature to a solution of 36.12 g (220 mmol) of 3-hydroxymethylchroman in 100 ml of absolute pyridine, the slightly exothermic reaction being maintained at room temperature by means of an ice bath. The reaction mixture is stirred for a further 3 hours at room temperature and then poured onto ice-water. The crystals formed are filtered off with suction, washed with water and dried in vacuo. 65.84 g (94%) of 3-(p-toluenesulphonyloxymethyl)chroman having a melting point of 86°–87° are obtained.

EXAMPLE 2

At room temperature and while stirring, 0.75 g (15.6 mmol) of sodium hydride dispersion in mineral oil (50%) is added within a period of 30 minutes to a solution of 4.36 g (13 mmol) of N,N-bis-(2-methoxycarbonylethyl)-N-(chroman-3-ylmethyl)-amine in 50 ml of absolute dimethylformamide. The reaction mixture is stirred for a further 1 hour at room temperature and then concentrated by evaporation under a high vacuum. Diethyl ether is added to the resulting residue and extraction is carried out with cold 2N hydrochloric acid. The combined hydrochloric acid extracts are extracted by shaking with dichloromethane and the combined dichloromethane extracts are dried over sodium sulphate and concentrated by evaporation. There are obtained 3.8 g (85.8%) of crystalline 4-hydroxy-1-(chroman-3-ylmethyl)-1,2,5,6-tetrahydropyridine-3-carboxylic acid methyl ester hydrochloride or 1-(chroman-3-ylmethyl)-4-oxo-piperidine-3-carboxylic acid methyl ester hydrochloride, respectively, which, after recrystallisation from methanol/diethyl ether has a decomposition point of 167°–168°.

N,N-bis(2-methoxycarbonylethyl)-N-(chroman-3-ylmethyl)-amine can be manufactured, for example, in the following manner:

First 1.77 g (13.32 mmol) of aluminium chloride in 50 ml of absolute diethyl ether are added dropwise while stirring at room temperature to a suspension of 3.04 g (80 mmol) of lithium aluminium hydride in 100 ml of absolute diethyl ether. Then 6.29 g (40 mmol) of 3-cyanochromene [R. C. Gupta et al., Ind. J. Chem. 21B, 344 (1982)] in 50 ml of absolute tetrahydrofuran are added dropwise within a period of 20 minutes. The reaction mixture is boiled under reflux for 16 hours. After it has cooled, it is carefully decomposed with 3.1 ml of water, 3.1 ml of sodium hydroxide solution (15% strength) and 9.3 ml of water. The precipitate formed is filtered off with suction, the filtrate is concentrated by evaporation in vacuo and the oily residue is dissolved in diethyl ether. The organic phase is washed with water and extracted with 2N hydrochloric acid. The combined hydrochloric acid extracts are rendered alkaline, while cold, with sodium hydroxide solution (30% strength) and extracted by shaking with dichloromethane. After drying the combined organic phases over sodium sulphate and concentrating in vacuo, 3.5 g (53.6%) of 3-aminomethylchroman are obtained in the form of a yellow oil. The 3-aminomethylchroman hydrochloride produced therefrom using hydrochloric acid in diethyl ether is recrystallised from methanol/diethyl ether and melts at 218°–219°.

3.03 g (35.2 mmol) of acrylic acid methyl ester are added to a solution of 2.61 g (16 mmol) of 3-aminomethylchroman in 20 ml of methanol. The reaction solution is stirred for 16 hours at 50° and, after cooling, is concentrated by evaporation in vacuo. 5.1 g (95%) of N,N-bis(2-methoxycarbonylethyl)-N-(chroman-3-ylmethyl)-amine are obtained in the form of a reddish oil.

EXAMPLE 3

A solution of 10.48 g (30 mmol) of N-[2-(chroman-3-yl)ethyl]-N,N-bis(2-methoxycarbonylethyl)-amine in 35 ml of absolute dimethylformamide is added dropwise at room temperature and while stirring to a suspension of 2.16 g (40 mmol) of sodium methoxide in 25 ml of dimethylformamide within a period of 15 minutes. The reaction mixture is stirred for 16 hours at room temperature and then concentrated to dryness by evaporation under a high vacuum. Diethyl ether is added to the residue and extraction is carried out with cold 2N hydrochloric acid. The combined hydrochloric acid extracts are extracted by shaking with dichloromethane and the dichloromethane phases are dried over sodium sulphate and concentrated by evaporation in vacuo. There are obtained 4.25 g (40%) of 1-[2-(chroman-3-yl)ethyl]-4-hydroxy-1,2,5,6-tetrahydropyridine-3-carboxylic acid methyl ester hydrochloride or 1-[2-(chroman-3-yl)ethyl]-4-oxopiperidine-3-carboxylic acid methyl ester hydrochloride, respectively, which after recrystallisation from methanol/diethyl ether, has a decomposition point of 175°–177°.

N-[2-(chroman-3-yl)ethyl]-N,N-bis(2-methoxycarbonylethyl)-amine can be manufactured, for example, in the following manner:

12.53 g (192.5 mmol) of potassium cyanide are added at room temperature to a solution of 55.72 g (175 mmol) of 3-(p-toluenesulphonyloxymethyl)chroman (for manufacture see Example 1) in 300 ml of dimethyl sulphoxide and the whole is heated to 60° while stirring. After 3 hours, ice-water is added to the reaction mixture, the whole is extracted with diethyl ether and washed thoroughly with water. The combined organic phases are dried over sodium sulphate and concentrated by evaporation in vacuo. 26.75 g (88.3%) of 3-cyanomethylchroman are obtained in the form of a pale yellow oil which crystallises from diethyl ether/pentane. The crystals melt at 63°.

First 4.44 g (33.3 mmol) of aluminium chloride in 150 ml of absolute diethyl ether are added dropwise while stirring at room temperature to a suspension of 7.59 g (200 mmol) of lithium aluminium hydride in 300 ml of absolute diethyl ether. Then 17.32 g (100 mmol) of 3-cyanomethylchroman, dissolved in 200 ml of tetrahydrofuran, are added dropwise within a period of 15 minutes. The reaction mixture is stirred for 16 hours at room temperature and then decomposed with 7.6 ml of water, 7.6 ml of sodium hydroxide solution (15% strength) and 22.8 ml of water. The precipitate formed is filtered off with suction and the filtrate is concentrated by evaporation in vacuo. The oily residue is dissolved in diethyl ether and washed with water. The organic phase is then extracted by shaking with 2N hydrochloric acid. The combined hydrochloric acid extracts are rendered alkaline, while cold, with sodium hydroxide solution (30% strength) and extracted with dichloromethane. The combined organic phases are dried over sodium sulphate and concentrated by evaporation in vacuo. 15.95 g (90%) of 3-(2-aminoethyl)chroman are obtained in the form of a colourless oil. The 3-(2-aminoethyl)chroman hydrochloride produced therefrom using hydrochloric acid in diethyl ether crystallises from methanol/diethyl ether and has a melting point of 244°–245°.

6.63 g (77 mmol) of acrylic acid methyl ester are added at room temperature to a solution of 6.2 g (35 mmol) of 3-(2-aminoethyl)chroman in 50 ml of methanol and the whole is stirred for 16 hours at room temperature. The reaction mixture is then concentrated by evaporation in vacuo and yields 12.23 g (100%) of N-[2-(chroman-3-yl)ethyl]-N,N-bis(2-methoxycarbonylethyl)-amine in the form of a reddish oil.

EXAMPLE 4

In a manner analogous to that described in Example 3, by reacting 3-(2-aminoethyl)chroman with 1 equivalent of acrylic acid methyl ester, it is possible to manufacture the corresponding N-[2-(chroman-3-yl)ethyl]-N-(2-methoxycarbonylethyl)-amine whose hydrochloride melts at 190°-192°.

EXAMPLE 5

In a manner analogous to that described in Examples 3 and 4, by reacting 3-aminomethylchroman with 1 equivalent of acrylic acid methyl ester, it is possible to manufacture N-(2-methoxycarbonylethyl)-N-(chroman-3-ylmethyl)-amine or its hydrochloride.

EXAMPLE 6

First 3.3 g (14.8 mmol) of 1,2,5,6-tetrahydropyridine-3-carboxylic acid methyl ester hydrobromide (guvacoline hydrobromide) and then 6.1 g (47.3 mmol) of N-ethyl-N,N-diisopropylamine are added to a solution of 4.5 g (13.5 mmol) of 3-[2-(p-toluenesulphonyloxy)ethyl]chroman in 70 ml of absolute dimethylformamide. The mixture is stirred for 16 hours at 60° and, after cooling, is concentrated by evaporation under a high vacuum. Water is added to the oily residue and extraction is carried out with diethyl ether. The combined organic phases are extracted with 2N hydrochloric acid. The combined hydrochloric acid extracts are rendered alkaline, while cold, with sodium hydroxide solution (30% strength) and extracted with dichloromethane. The combined dichloromethane phases are dried over sodium sulphate and concentrated by evaporation in vacuo. 3.97 g (97.7%) of 1-[2-(chroman-3-yl)ethyl]-1,2,5,6-tetrahydropyridine-3-carboxylic acid methyl ester are obtained in the form of a yellow oil. The 1-[2-(chroman-3-yl)ethyl]-1,2,5,6-tetrahydropyridine-3-carboxylic acid methyl ester hydrochloride produced therefrom using hydrochloric acid in diethyl ether crystallises from methanol/diethyl ether and melts at 175°-177°.

3-[2-(p-toluenesulphonyloxy)ethyl]chroman can be manufactured, for example, as follows:

50 ml of 2N sodium hydroxide solution are added to a solution of 7.8 g (45 mmol) of 3-cyanomethylchroman in 150 ml of ethanol and the whole is boiled under reflux for 16 hours. After cooling, the reaction mixture is concentrated by evaporation in vacuo. The residue is dissolved in water and extracted with diethyl ether. The aqueous phase is acidified with hydrochloric acid (36% strength) and extracted by shaking with dichloromethane. The combined dichloromethane extracts are dried over sodium sulphate and concentrated by evaporation in vacuo. 8.3 g (96%) of 3-carboxymethylchroman are obtained in the form of colourless crystals which melt at 106°-107°.

1.5 ml of sulphuric acid (100% strength) are added to a solution of 7.69 g (40 mmol) of 3-carboxymethylchroman in 150 ml of methanol and the whole is boiled under reflux for 3 hours. After cooling, the reaction mixture is concentrated by evaporation in vacuo. The residue is dissolved in diethyl ether and washed, while cold, with water, sodium hydrogen carbonate and again with water. The combined organic phases are dried over sodium sulphate and concentrated by evaporation in vacuo. 8.08 g (98%) of 3-methoxycarbonylmethylchroman are obtained in the form of a pale yellow oil.

At room temperature and while stirring, a solution of 7.22 g (35 mmol) of 3-methoxycarbonylmethylchroman in 50 ml of absolute tetrahydrofuran is added dropwise within a period of 30 minutes to a suspension of 1.33 g (35 mmol) of lithium aluminium hydride in 50 ml of absolute diethyl ether. Stirring is continued at room temperature for a further 16 hours and then the whole is carefully decomposed with 1.33 ml of water, 1.33 ml of sodium hydroxide solution (15% strength) and 4.0 ml of water. The precipitate formed is filtered off with suction and the filtrate is concentrated by evaporation in vacuo. The oily residue is dissolved in diethyl ether. The solution is washed with water, dried over sodium sulphate and concentrated by evaporation in vacuo. 6.23 g (100%) of 3-(2-hydroxyethyl)chroman are obtained in the form of a yellow oil.

6.29 g (33 mmol) of p-toluenesulphonyl chloride are added while stirring at room temperature to a solution of 5.35 g (30 mmol) of 3-(2-hydroxyethyl)chroman in 30 ml of absolute pyridine, the slightly exothermic reaction being maintained at room temperature by means of an ice bath. After stirring for a further three hours at room temperature, the reaction mixture is poured onto ice-water. The crystals formed are filtered off with suction, washed with water and dried in vacuo. 5.9 g (59.2%) of 3-[2-(p-toluenesulphonyloxy)ethyl]chroman, which melts at 91°-93°, are obtained.

EXAMPLE 7

First 11.1 g (50 mmol) of 1,2,5,6-tetrahydropyridine-3-carboxylic acid methyl ester hydrobromide (guvacoline hydrobromide) and then 22.6 g (175 mmol) of N-ethyl-N,N-diisopropylamine are added to a solution of 11.45 g (50 mmol) of 2-bromomethylbenzo-1,4-dioxan (U.S. Pat. No. 2,366,102) in 100 ml of absolute dimethylformamide. The mixture is stirred for 16 hours at 50° and then concentrated by evaporation under a high vacuum. Water is added to the residue and extraction is carried out with diethyl ether. The organic phases are washed with water and extracted by shaking with 2N hydrochloric acid. The combined hydrochloric acid extracts are rendered alkaline, while cold, with sodium hydroxide solution (30% strength) and extracted with dichloromethane. The combined dichloromethane phases are dried over sodium sulphate and concentrated by evaporation in vacuo. 10.75 g (74.4%) of 1-(benzo-1,4-dioxan-2-ylmethyl)-1,2,5,6-tetrahydropyridine-3-carboxylic acid methyl ester are obtained in the form of a yellow oil. The 1-(benzo-1,4-dioxan-2-ylmethyl)-1,2,5,6-tetrahydropyridine-3-carboxylic acid methyl ester hydrochloride produced therefrom using hydrochloric acid in diethyl ether crystallises from methanol/diethyl ether and decomposes at 215°-217°.

EXAMPLE 8

0.5 g of palladium-on-carbon (5%) is added to a solution of 4.88 g (15 mmol) of 1-(benzo-1,4-dioxan-2-ylmethyl)-1,2,5,6-tetrahydropyridine-3-carboxylic acid methyl ester hydrochloride in 100 ml of methanol and the whole is hydrogenated for 6 hours at room temperature and at normal pressure. The catalyst is then filtered off with suction and the filtrate is concentrated by evaporation in vacuo. The oily residue is dissolved in hot acetone and diethyl ether is added until the solution becomes turbid. 4.08 g (83%) of 1-(benzo-1,4-dioxan-2-ylmethyl)-piperidine-3-carboxylic acid methyl ester hydrochloride having a melting point of 186°-188° crystallise out.

EXAMPLE 9

At room temperature and while stirring, a solution of 10.12 g (30 mmol) of N,N-bis(2-methoxycarbonylethyl)-N-(benzo-1,4-dioxan-2-ylmethyl)-amine in 25 ml of absolute dimethylformamide is added dropwise within a period of 15 minutes to a suspension of 2.16 g (40 mmol) of sodium methoxide in 25 ml of dimethylformamide. The reaction mixture is stirred for a further 3 hours at room temperature and then concentrated to dryness by evaporation under a high vacuum. Diethyl ether is added to the residue and extraction by shaking is carried out with cold 2N hydrochloric acid. The combined hydrochloric acid extracts are extracted with dichloromethane and the dichloromethane phases are dried over sodium sulphate and concentrated by evaporation in vacuo. There are obtained 4.5 g (44.4%) of 4-hydroxy-1-(benzo-1,4-dioxan-2-ylmethyl)-1,2,5,6-tetrahydropyridine-3-carboxylic acid methyl ester hydrochloride or 1-(benzo-1,4-dioxan-2-yl-methyl)-4-oxopiperidine-3-carboxylic acid methyl ester hydrochloride, respectively, which is recrystallised from methanol/diethyl ether and has a decomposition point of 185°–187°.

N,N-bis(2-methoxycarbonylethyl)-N-(benzo-1,4-dioxan-2-ylmethyl)-amine can be manufactured, for example, as follows:

7.57 g (88 mmol) of acrylic acid methyl ester are added to a solution of 6.61 g (40 mmol) of 2-aminomethylbenzo-1,4-dioxan [J. Augustin et al., J. Med. Chem. 8, 446 (1965)] in 80 ml of methanol and the whole is stirred for 16 hours at 50°. After cooling, the reaction mixture is concentrated by evaporation in vacuo. 12.82 g (95%) of N,N-bis(2-methoxycarbonylethyl)-N-(benzo-1,4-dioxan-2-ylmethyl)-amine are obtained in the form of a reddish oil.

EXAMPLE 10

In a manner analogous to that described in Example 9, by reacting 2-aminomethylbenzo-1,4-dioxan with 1 equivalent of acrylic acid methyl ester, it is possible to manufacture the corresponding N-(2-methoxycarbonylethyl)-N-(benzo-1,4-dioxan-2-ylmethyl)amine whose hydrochloride melts at 153°–155°.

EXAMPLE 11

In a manner analogous to that described in Example 9, it is also possible to manufacture 4-hydroxy-1-(2-methylbenzo-1,4-dioxan-2-ylmethyl)-1,2,5,6-tetrahydropyridine-3-carboxylic acid methyl ester hydrochloride or 1-(2-methylbenzo-1,4-dioxan-2-ylmethyl)-4-oxopiperidine-3-carboxylic acid methyl ester hydrochloride, respectively.

EXAMPLE 12

In a manner analogous to that described in Examples 9 and 10, by reacting 2-(2-aminoethyl)benzo-1,4-dioxan with 1 equivalent of acrylic acid methyl ester, it is possible to manufacture N-[2-(benzo-1,4-dioxan-2-yl)ethyl]-N-(2-methoxycarbonylethyl)-amine and its hydrochloride, and by reacting 2-aminomethyl-2-methylbenzo-1,4-dioxan with 1 equivalent of acrylic acid methyl ester, it is possible to manufacture N-(2-methoxycarbonylethyl)-N-(2-methylbenzo-1,4-dioxan-2-ylmethyl)-amine and its hydrochloride.

EXAMPLE 13

A solution of 52.7 g (0.15 mol) of N,N-bis(2-methoxycarbonylethyl)-N-[2-(benzo-1,4-dioxan-2-yl)ethyl]-amine in 150 ml of absolute dimethylformamide is added dropwise at room temperature while stirring to a suspension of 10.8 g (0.20 mol) of sodium methoxide in 100 ml of absolute dimethylformamide within a period of 10 minutes. The reaction mixture is stirred for a further 15 hours at room temperature and then concentrated to dryness by evaporation under a high vacuum. Diethyl ether is added to the resulting residue and extraction is carried out with cold 2N hydrochloric acid. The combined hydrochloric acid extracts are extracted by shaking with dichloromethane. The dichloromethane phases are dried over sodium sulphate and concentrated by evaporation in vacuo. There are obtained 34.0 g (63.7%) of 1-[2-(benzo-1,4-dioxan-2-yl)ethyl]-4-hydroxy-1,2,5,6-tetrahydropyridine-3-carboxylic acid methyl ester hydrochloride or 1-[2-(benzo-1,4-dioxan-2-yl)ethyl]-4-oxopiperidine-3-carboxylic acid methyl ester hydrochloride, respectively, which is recrystallised from methanol/diethyl ether and has a decomposition point of 165°–166°.

N,N-bis(2-methoxycarbonylethyl)-N-[2-(benzo-1,4-dioxan-2-yl)ethyl]-amine can be manufactured, for example, in the following manner:

34.1 g (0.396 mol) of acrylic acid methyl ester are added at room temperature to a solution of 32.25 g (0.18 mol) of 2-(2-aminoethyl)-benzo-1,4-dioxan [J. Augustin et al., J. Med. Chem. 8, 446 (1965)] in 250 ml of methanol. The reaction mixture is stirred for 6 hours at 50° and, after cooling, is concentrated by evaporation in vacuo. 57.9 g (91.5%) of N,N-bis(2-methoxycarbonylethyl)-N-[2-(benzo-1,4-dioxan-2-yl)ethyl]-amine are obtained in the form of a red oil.

EXAMPLE 14

1.25 g of platinum oxide are added to a solution of 12.45 g (35 mmol) of 1-[2-(benzo-1,4-dioxan-2-yl)ethyl]-4-hydroxy-1,2,5,6-tetrahydropyridine-3-carboxylic acid methyl ester hydrochloride or 1-[2-(benzo-1,4-dioxan-2-yl)ethyl]-4-oxopiperidine-3-carboxylic acid methyl ester hydrochloride, respectively, in 250 ml of methanol and the whole is hydrogenated at room temperature and at normal pressure. After the theoretically necessary amount of hydrogen has been taken up, the catalyst is separated off, the filtrate is concentrated by evaporation in vacuo and the oily residue is dissolved in hot acetone. After cooling, 4.87 g (38.9%) of cis-1-[2-(benzo-1,4-dioxan-2-yl)ethyl]-4-hydroxypiperidine-3-carboxylic acid methyl ester hydrochloride having a melting point of 182°–185° crystallise out.

EXAMPLE 15

At −15° and while stirring, 2.65 g (70 mmol) of sodium borohydride are added in portions over a period of one hour to a suspension of 12.45 g (35 mmol) of 1-[2-(benzo-1,4-dioxan-2-yl)ethyl]-4-hydroxy-1,2,5,6-tetrahydropyridine-3-carboxylic acid methyl ester hydrochloride or 1-[2-(benzo-1,4-dioxan-2-yl)ethyl]-4-oxopiperidine-3-carboxylic acid methyl ester hydrochloride, respectively, in 250 ml of methanol. Stirring is continued for a further 4 hours at −10° and then the reaction mixture is concentrated by evaporation in vacuo and taken up in water/ethyl acetate. The ethyl acetate extracts are washed with water, dried over sodium sulphate and concentrated by evaporation. 11.2 g (100%) of crude product are obtained which are chromatographed on 560 g of silica gel (0.040–0.063 mm) using ethyl acetate as the eluant. 5.41 g (48.2%) of trans-1-[2-(benzo-1,4-dioxan-2-yl)ethyl]-4-hydroxypiperidine-3-carboxylic acid methyl ester are obtained in the form of a pale yellow oil. The trans-1-[2-(benzo-1,4-dioxan-2-yl)ethyl]-4-hydroxypiperidine-3-carboxylic acid methyl ester fumarate produced therefrom using fumaric acid crystallises from methanol/diethyl ether in the form of the hemihydrate having a melting point of 150°–152°.

EXAMPLE 16

First 19.03 g (125 mmol) of 1,5diazabicyclo[5.4.0]undec-5-ene and then, dropwise and while stirring at 0°–5°, a solution of 3.44 g (30 mmol) of methanesulphonyl chloride in 20 ml of toluene are added to a solution of 8.03 g (25 mmol) of a mixture of cis- and trans-1-[2-(benzo-1,4-dioxan-2-yl)ethyl]-4-hydroxypiperidine-3-carboxylic acid methyl ester in 100 ml of toluene. The whole is then allowed to warm up to room temperature and is stirred for a further 16 hours. Ice-water is then added to the reaction mixture and the organic phase is extracted with 2N hydrochloric acid. The combined hydrochloric acid extracts are rendered alkaline, while cold, with sodium hydroxide solution (30% strength) and extracted by shaking with dichloromethane. The combined organic phases are washed with water, dried over sodium sulphate and concentrated by evaporation in vacuo. 5.8 g (76.5%) of crude product are obtained and are chromatographed on 300 g of silica gel (0.040–0.063 mm) using toluene/ethyl acetate (1:1) as the eluant. 4.13 g (54.5%) of 1-[2-(benzo-1,4-dioxan-2-yl)ethyl]-1,2,5,6-tetrahydropyridine-3-carboxylic acid methyl ester are obtained in the form of a yellow oil. The 1-[2-(benzo-1,4-dioxan-2-yl)ethyl]-1,2,5,6-tetrahydropyridine-3-carboxylic acid methyl ester hydrochloride produced therefrom using hydrochloric acid in diethyl ether crystallises from methanol/diethyl ether and decomposes at 205°–206°.

EXAMPLE 17

First 2.1 g (11 mmol) of 1,2,5,6-tetrahydropyridine-3-carboxylic acid ethyl ester hydrochloride and then 4.53 g (35 mmol) of N-ethyl-N,N-diisopropylamine are added to a solution of 3.32 g (10 mmol) of 3-[2-(p-toluenesulphonyloxy)ethyl]-chroman in 50 ml of absolute dimethylformamide. The mixture is stirred for 16 hours at 60° and, after cooling, is concentrated by evaporation under a high vacuum. Water is added to the oily residue and extraction is carried out with diethyl ether. The combined organic phases are extracted with 2N hydrochloric acid. The combined hydrochloric acid extracts are rendered alkaline, while cold, with sodium hydroxide solution (30% strength) and extracted with dichloromethane. The combined dichloromethane phases are dried over sodium sulphate and concentrated by evaporation in vacuo. 1.65 g (52.3%) of 1-[2-(chroman-3-yl)ethyl]-1,2,5,6-tetrahydropyridine-3-carboxylic acid ethyl ester are obtained in the form of a yellow oil. The 1-[2-(chroman-3-yl)ethyl]-1,2,5,6-tetrahydropyridine-3-carboxylic acid ethyl ester hydrochloride produced therefrom using hydrochloric acid in diethyl ether crystallises from acetone/diethyl ether and melts at 177°–178°.

EXAMPLE 18

3.4 ml of sulphuric acid (100% strength) are added to a solution of 2.54 g (7.5 mmol) of 1-[2-(chroman-3-yl)ethyl]-1,2,5,6-tetrahydropyridine-3-carboxylic acid methyl ester hydrochloride in 170 ml of absolute ethanol and the whole is boiled under reflux for 35 hours. After cooling, the reaction mixture is concentrated by evaporation in vacuo. The residue is dissolved in water while cold and is extracted with diethyl ether. The aqueous phase is rendered alkaline, while cold, with sodium hydroxide solution (30% strength) and extracted with dichloromethane. The combined dichloromethane extracts are dried over sodium sulphate and concentrated by evaporation in vacuo. 2.30 g (97.4%) of 1-[2-(chroman-3-yl)ethyl]-1,2,5,6-tetrahydropyridine-3-carboxylic acid ethyl ester are obtained in the form of a yellow oil. The 1-[2-(chroman-3-yl)ethyl]-1,2,5,6-tetrahydropyridine-3-carboxylic acid ethyl ester hydrochloride produced therefrom using hydrochloric acid in diethyl ether crystallises from acetone/diethyl ether and melts at 177°–178°.

EXAMPLE 19

First 3.76 g (24 mmol) of piperidine-3-carboxylic acid ethyl ester and then 3.1 g (24 mmol) of N-ethyl-N,N-diisopropylamine are added to a solution of 3.98 g (12 mmol) of 3-[2-(p-toluenesulphonyloxy)ethyl]chroman in 50 ml of absolute dimethylformamide. The mixture is stirred for 16 hours at 60° and, after cooling, is concentrated by evaporation under a high vacuum. Water is added to the oily residue and extraction is carried out with diethyl ether. The combined organic phases are extracted with 2N hydrochloric acid. The combined hydrochloric acid extracts are rendered alkaline, while cold, with sodium hydroxide solution (30% strength) and extracted with dichloromethane. The combined dichloromethane phases are dried over sodium sulphate and concentrated by evaporation in vacuo. 3.7 g (97.3%) of 1-[2-(chroman-3-yl)ethyl]-piperidine-3-carboxylic acid ethyl ester are obtained in the form of a yellow oil. The 1-[2-(chroman-3-yl)ethyl]-piperidine-3-carboxylic acid ethyl ester hydrochloride produced therefrom using hydrochloric acid in diethyl ether crystallises from acetone/diethyl ether using 0.18 equivalent of water of crystallisation and melts at 140°–143°.

EXAMPLE 20

First 3.76 g (24 mmol) of piperidine-4-carboxylic acid ethyl ester and then 3.1 g (24 mmol) of N-ethyl-N,N-diisopropylamine are added to a solution of 3.98 g (12 mmol) of 3-[2-(p-toluenesulphonyloxy)ethyl]chroman in 50 ml of absolute dimethylformamide. The mixture is stirred for 16 hours at 60° and, after cooling, is concentrated by evaporation under a high vacuum. Water is added to the oily residue and extraction by shaking is carried out with diethyl ether. The combined organic phases are extracted with 2N hydrochloric acid. The combined hydrochloric acid extracts are rendered alkaline, while cold, with sodium hydroxide solution (30% strength) and extracted with dichloromethane. The combined dichloromethane phases are dried over sodium sulphate and concentrated by evaporation in vacuo. 3.8 g (100%) of crude product are obtained which are chromatographed on 200 g of silica gel (0.040–0.063 mm) using ethyl acetate as the eluant. 3.7 g (97.3%) of 1-[2-(chroman-3-yl)ethyl]-piperidine-4-carboxylic acid ethyl ester are then obtained in the form of a colourless oil. The 1-[2-chroman-3-yl)ethyl]-piperidine-4-carboxylic acid ethyl ester hydrochloride produced therefrom using hydrochloric. acid in diethyl ether crystallises from ethanol/diethyl ether and melts at 182°–186°.

EXAMPLE 21

First 1.96 g (12.5 mmol) of piperidine-3-carboxylic acid ethyl ester and then 2.58 g (20 mmol) of N-ethyl-N,N-diisopropylamine are added to a solution of 3.34 g (10 mmol) of 2-[2-(p-toluenesulphonyloxy)ethyl]-benzo-1,4-dioxan in 50 ml of absolute dimethylformamide. The mixture is stirred for 16 hours at 60° and, after cooling, is concentrated by evaporation under a high vacuum. Water is added to the oily residue and extraction is carried out with diethyl ether. The combined organic phases are washed with water and extracted with 2N hydrochloric acid. The combined hydrochloric acid extracts are rendered alkaline, while cold, with sodium hydroxide solution (30% strength) and extracted with dichloromethane. The combined dichloromethane phases are dried over sodium sulphate and concentrated by evaporation in vacuo. 3.82 g (100%) of crude product are obtained which are filtered over 190 g of silica gel (0.040-0.063 mm) using ethyl acetate as the eluant. 3.70 g (96.6%) of 1-[2-(benzo-1,4-dioxan-2-yl)ethyl]-piperidine-3-carboxylic acid ethyl ester are then obtained in the form of a pale yellow oil. The 1-[2-(benzo-1,4-dioxan-2-yl)ethyl]-piperidine-3-carboxylic acid ethyl ester hydrochloride produced therefrom using hydrochloric acid in diethyl ether crystallises from ethanol/diethyl ether and melts at 162°-165°.

The 2-[2-(p-toluenesulphonyloxy)ethyl]-benzo-1,4-dioxan can be obtained, for example, in the following manner:

Hydrogen chloride is introduced at 5°-10°, while stirring, into a solution of 15.76 g (90 mmol) of 2-cyanomethylbenzo-1,4-dioxan (BE 613,211) in 200 ml of absolute methanol until saturation is reached. The reaction mixture is then thawed to room temperature and is stirred for a further 16 hours at that temperature. The reaction mixture is then boiled under reflux for 2 hours. After cooling, the mixture is concentrated by evaporation in vacuo. Ice-water is added to the oily residue and extraction is carried out with diethyl ether. The combined organic phases are washed, while cold, with water, saturated sodium hydrogen carbonate solution and again with water, and then dried over sodium sulphate and concentrated by evaporation in vacuo. 18.2 g (97.3%) of 2-methoxycarbonylmethylbenzo-1,4-dioxan are obtained in the form of a pale yellow oil.

At room temperature and while stirring, a solution of 15.61 g (75 mmol) of 2-methoxycarbonylmethylbenzo-1,4-dioxan in 120 ml of absolute tetrahydrofuran is added dropwise within a period of 30 minutes to a suspension of 2.85 g (75 mmol) of lithium aluminium hydride in 120 ml of absolute diethyl ether. The reaction mixture is stirred for a further 2 hours at room temperature. It is then carefully decomposed with 2.85 ml of water, 2.85 ml of sodium hydroxide solution (15% strength) and 8.55 ml of water. The precipitate formed is filtered off with suction and the filtrate is concentrated by evaporation in vacuo. The oily residue is dissolved in diethyl ether. The solution is washed thoroughly with water, dried over sodium sulphate and concentrated by evaporation in vacuo. 12.37 g (91.6%) of 2-(2-hydroxyethyl)-benzo-1,4-dioxan are obtained in the form of a colourless oil.

12.20 g (64 mmol) of p-toluenesulphonyl chloride are added at room temperature and while stirring to a solution of 10.81 g (60 mmol) of 2-(2-hydroxyethyl)benzo-1,4-dioxan in 35 ml of absolute pyridine, the slightly exothermic reaction being maintained at room temperature by means of an ice bath. The reaction mixture is stirred for a further 3 hours at room temperature and then poured onto ice-water. The crystals formed are filtered off with suction, washed with water and dried in vacuo. 15.50 g (77.2%) of 2-[2-(p-toluenesulphonyloxy)ethyl]-benzo-1,4-dioxan, which melts at 82°-84°, are obtained.

EXAMPLE 22

First 1.96 g (12.5 mmol) of piperidine-4-carboxylic acid ethyl ester and then 2.58 g (20 mmol) of N-ethyl-N,N-diisopropylamine are added to a solution of 3.34 g (10 mmol) of 2-[2-(p-toluenesulphonyloxy)ethyl]-benzo-1,4-dioxan in 50 ml of absolute dimethylformamide. The mixture is stirred for 16 hours at 60° and, after cooling, is concentrated by evaporation under a high vacuum. Water is added to the oily residue and extraction is carried out with diethyl ether. The combined organic phases are washed with water and extracted with 2N hydrochloric acid. The combined hydrochloric acid extracts are rendered alkaline, while cold, with sodium hydroxide solution (30% strength) and extracted with dichloromethane. The combined dichloromethane phases are dried over sodium sulphate and concentrated by evaporation in vacuo. 3.80 g (99.2%) of crude product are obtained which are filtered over 190 g of silica gel (0.040-0.063 mm) using ethyl acetate as the eluant. 3.7 g (96.6%) of 1-[2-(benzo-1,4-dioxan-2-yl)ethyl]-piperidine-4-carboxylic acid ethyl ester are then obtained in the form of a yellow oil. The 1-[2-(benzo-1,4-dioxan-2-yl)ethyl]-piperidine-4-carboxylic acid ethyl ester hydrochloride produced therefrom using hydrochloric acid in diethyl ether crystallises from ethanol/diethyl ether and melts at 165°-168°.

EXAMPLE 23

21 ml (42 mmol) of 2N sodium hydroxide solution are added at room temperature while stirring to a solution of 2.99 g (10 mmol) of N-[2-(chroman-3-yl)ethyl]-N-(2-methoxycarbonylethyl)-amine hydrochloride in 60 ml of methanol. After 5 minutes, 40 ml of water are added to the reaction mixture which is then stirred for 30 minutes at 50°-60°. After cooling, the mixture is concentrated by evaporation in vacuo. The residue is dissolved in 30 ml of water, and then 10 ml of hydrochloric acid (36% strength) are added and the whole is cooled in an ice bath. The crystals formed are filtered off with suction. 2.5 g (87.5%) of N-[2-(chroman-3-yl)ethyl]-N-(2-carboxyethyl)-amine hydrochloride are obtained (m.p. 186°-188°).

The N-[2-(chroman-3-yl)ethyl]-N-(2-methoxycarbonylethyl)-amine hydrochloride can be manufactured, for example, as described in Example 4.

EXAMPLE 24

First 1.57 g (10 mmol) of piperidine-3-carboxylic acid ethyl ester and then 2.07 g (16 mmol) of N-ethyl-N,N-diisopropylamine are added to a solution of 2.66 g (8 mmol) of 2-[2-(p-toluenesulphonyloxy)ethyl]chroman in 35 ml of absolute dimethylformamide. The mixture is stirred for 16 hours at 60° and, after cooling, is concentrated by evaporation under a high vacuum. Water is added to the oily residue and extraction is carried out with diethyl ether. The combined organic phases are washed with water and extracted with 2N hydrochloric acid. The combined hydrochloric acid extracts are rendered alkaline, while cold, with sodium hydroxide solution (30% strength) and extracted with dichloromethane. The combined dichloromethane phases are dried over sodium sulphate and concentrated by evaporation in vacuo. 2.28 g (90.1%) of crude product are obtained and are chromatographed on 120 g of silica gel (0.040-0.063 mm) using ethyl acetate as the eluant. 1.82 g (72.2%) of 1-[2-(chroman-2-yl)ethyl]-piperidine-3-carboxylic acid ethyl ester are then obtained in the form of a yellow oil. The 1-[2-(chroman-2-yl)ethyl]-piperidine-3-carboxylic acid ethyl ester hydrochloride produced therefrom using hydrochloric acid in diethyl ether crystallises from ethanol/diethyl ether and melts at 148°–151°.

2-[2-(p-toluenesulphonyloxy)ethyl]chroman can be manufactured, for example, in the following manner:

14.2 ml of sulphuric acid (100% strength) are added to a solution of 70.34 g (0.39 mol) of 2-carboxychroman in 1400 ml of methanol and the whole is boiled under reflux for 4 hours. After cooling, the reaction mixture is concentrated by evaporation in vacuo and the residue is dissolved in diethyl ether and washed with water, cold saturated sodium hydrogen carbonate solution and again with water. The ethereal phase is dried over sodium sulphate and concentrated by evaporation in vacuo. 72.8 g (96%) of 2-methoxycarbonylchroman are obtained in the form of a pale yellow oil.

At room temperature and while stirring, a solution of 36.4 g (0.19 mol) of 2-methoxycarbonylchroman in 400 ml of absolute tetrahydrofuran is added dropwise within a period of 1 hour to a suspension of 7.2 g (0.19 mol) of lithium aluminium hydride in 400 ml of absolute diethyl ether. After continuing to stir for a further 16 hours at room temperature, the reaction mixture is carefully decomposed with 7.2 ml of water, 7.2 ml of sodium hydroxide solution (15% strength) and 21.6 ml of water. The precipitate formed is filtered off with suction and the filtrate is concentrated by evaporation in vacuo. The oily residue is dissolved in diethyl ether. The ethereal solution is washed with water, dried over sodium sulphate and concentrated by evaporation in vacuo. 31 g (99.3%) of 2-hydroxymethylchroman are thus obtained in the form of a colourless oil.

38.16 g (0.2 mol) of p-toluenesulphonyl chloride are added at room temperature while stirring to a solution of 31 g (0.189 mol) of 2-hydroxymethylchroman in 110 ml of absolute pyridine, the slightly exothermic reaction being maintained at room temperature by means of an ice bath. The reaction mixture is stirred for a further 3 hours at room temperature and then poured onto ice-water. The oil which separates out is removed by decanting the aqueous phase, dissolved in diethyl ether and washed with ice-cold 2N hydrochloric acid and ice-water. The ethereal phases are dried over sodium sulphate and concentrated by evaporation in vacuo. 58.15 g (96.6%) of 2-(p-toluenesulphonyloxymethyl)-chroman are obtained in the form of a colourless oil.

10.6 g (0.216 mol) of sodium cyanide are added to a solution of 57.31 g (0.18 mol) of 2-(p-toluenesulphonyloxymethyl)chroman in 800 ml of absolute dimethylformamide and the whole is heated, while stirring, to 60°. After 10 hours, ice-water is added to the reaction mixture and extraction is carried out with diethyl ether. The combined ethereal phases are washed thoroughly with water, dried over sodium sulphate and concentrated by evaporation in vacuo. 30.0 g (96.2%) of crude product are obtained and are chromatographed on 1000 g of silica gel (0.040–0.063 mm) using toluene as the eluant. 18.16 g (58.2%) of 2-cyanomethylchroman are thus obtained in the form of a yellow oil.

Hydrogen chloride gas is introduced at 5°–10° into a solution of 17.32 g (0.1 mol) of 2-cyanomethylchroman in 200 ml of absolute methanol until saturation is reached. The reaction mixture is then thawed to room temperature and is stirred for a further 16 hours at that temperature. The reaction mixture is then boiled under reflux for 2 hours. It is then cooled and the mixture is concentrated by evaporation in vacuo. Ice-water is added to the residue and extraction is carried out with diethyl ether. The combined organic phases are washed, while cold, with water, sodium hydrogen carbonate solution and again with water, and then dried over sodium sulphate and concentrated by evaporation in vacuo. 18.58 g (90.1%) of crude product are obtained and are filtered over 460 g of silica gel (0.040–0.063 mm) using toluene as the eluant. 17.80 g (86.3%) of 2-methoxycarbonylmethylchroman are obtained in the form of a pale yellow oil.

At room temperature and while stirring, a solution of 16.91 g (82 mmol) of 2-methoxycarbonylmethylchroman in 150 ml of absolute tetrahydrofuran is added dropwise within a period of 30 minutes to a suspension of 3.11 g (82 mmol) of lithium aluminium hydride in 150 ml of absolute diethyl ether. Stirring is continued for a further 16 hours at room temperature and then the whole is carefully decomposed with 3.1 ml of water, 3.1 ml of sodium hydroxide solution (15% strength) and 9.3 ml of water. The precipitate formed is filtered off with suction and the filtrate is concentrated by evaporation in vacuo. The oily residue is dissolved in diethyl ether. The ethereal solution is washed with water, dried over sodium sulphate and concentrated by evaporation in vacuo. 14.36 g (98.3%) of 2-(2-hydroxyethyl)chroman are obtained in the form of a colourless oil.

15.73 g (82.5 mmol) of p-toluenesulphonyl chloride are added at room temperature while stirring to a solution of 13.36 g (75 mmol) of 2-(2-hydroxyethyl)chroman in 90 ml of absolute pyridine, the slightly exothermic reaction being maintained at room temperature by means of an ice bath. After stirring for a further 3 hours at room temperature, the reaction mixture is poured onto ice-water. The crystals formed are filtered off with suction, washed with water and dried in vacuo. There are obtained 8.68 g (34.7%) of 2-[2-(p-toluenesulphonyloxy)ethyl]chroman which melts at 57°–59°.

EXAMPLE 25

First 1.57 g (10 mmol) of piperidine-4-carboxylic acid ethyl ester and then 2.07 g (16 mmol) of N-ethyl-N,N-diisopropylamine are added to a solution of 2.66 g (8 mmol) of 2-[2-(p-toluenesulphonyloxy)ethyl]chroman in 35 ml of absolute dimethylformamide. The mixture is stirred for 16 hours at 60° and then, after cooling, is concentrated by evaporation under a high vacuum. Water is added to the oily residue and extraction is carried out with diethyl ether. The combined organic phases are washed with water and extracted with 2N hydrochloric acid. The combined hydrochloric acid extracts are rendered alkaline, while cold, with sodium hydroxide solution (30% strength) and extracted with dichloromethane. The combined dichloromethane phases are dried over sodium sulphate and concentrated by evaporation in vacuo. 2.17 g (85.7%) of crude product are obtained and are chromatographed on 110 g of silica gel (0.040–0.063 mm) using ethyl acetate as the eluant. 1.90 g (75.1%) of 1-[2-(chroman-2-yl)ethyl]-piperidine-4-carboxylic acid ethyl ester are thus obtained in the form of a yellow oil. The 1-[2-(chroman-2-yl)ethyl]-piperidine-4-carboxylic acid ethyl ester hydrochloride produced therefrom using hydrochloric acid in diethyl ether crystallises from ethanol/diethyl ether and melts at 190°–192°.

EXAMPLE 26

3.01 g (35 mmol) of acrylic acid methyl ester are added at 0°–5°, while stirring, to a solution of 6.2 g (35 mmol) of 2-(2-aminoethyl)chroman in 200 ml of methanol. Stirring is continued for a further 16 hours at 0°–5° and the mixture is then concentrated by evaporation in vacuo. 8.76 g (95.2%) of crude product are obtained and are chromatographed on 250 g of silica gel (0.040–0.063 mm) using ethyl acetate as the eluant. 5.10 g (55.4%) of N-[2-(chroman-2-yl)ethyl]-N-(2-methoxycarbonylethyl)-amine are thus obtained in the form of a yellow oil. The N-[2-(chroman-2-yl)ethyl]-N-(2-methoxycarbonylethyl)-amine hydrochloride produced therefrom using hydrochloric acid in diethyl ether crystallises from methanol/diethyl ether and melts at 152°–153°.

2-(2-aminoethyl)chroman can be manufactured, for example, in the following manner:

First, at room temperature and while stirring, 2.2 g (16.5 mmol) of aluminium chloride in 70 ml of absolute diethyl ether are added dropwise to a suspension of 3.8 g (100 mmol) of lithium aluminium hydride in 150 ml of absolute diethyl ether. Then 8.66 g (50 mmol) of 2-cyanomethylchroman in 70 ml of absolute tetrahydrofuran are added dropwise within a period of 20 minutes. The reaction mixture is stirred for a further 16 hours at room temperature and then carefully decomposed with 3.8 ml of water, 3.8 ml of sodium hydroxide solution (15% strength) and 11.4 ml of water. The precipitate formed is filtered off with suction and the filtrate is concentrated by evaporation in vacuo. The oily residue is dissolved in diethyl ether. The ethereal phase is washed with water, dried over sodium sulphate and concentrated by evaporation. 8.75 g (98.8%) of 2-(2-aminoethyl)chroman are obtained in the form of a colourless oil.

EXAMPLE 27

1.5 ml of concentrated hydrochloric acid are added to a solution of 4.81 g (0.015 mol) of 1-[2-(chroman-3-yl)ethyl]-3-cyano-4-hydroxy-1,2,5,6-tetrahydropyridine hydrochloride or 1-[2-(chroman-3-yl)ethyl]-3-cyano-4-oxopiperidine hydrochloride, respectively, in 100 ml of methanol (95% strength) and the whole is boiled under reflux for 15 hours. After cooling, the reaction mixture is concentrated to a volume of approximately 30 ml under reduced pressure and the solution is poured into a mixture of 80 ml of 5N hydrochloric acid and 20 ml of toluene, whereupon, while stirring and cooling, 1-[2-(chroman-3-yl)ethyl]-4-hydroxy-1,2,5,6-tetrahydropyridine-3-carboxylic acid methyl ester hydrochloride or 1-[2-(chroman-3-yl)ethyl]-4-oxopiperidine-3-carboxylic acid methyl ester hydrochloride, respectively, having a melting point of 175°–177° (decomposition) crystallises out.

The 1-[2-(chroman-3-yl)ethyl]-3-cyano-4-hydroxy-1,2,5,6-tetrahydropyridine hydrochloride or 1-[2-(chroman-3-yl)ethyl]-3-cyano-4-oxopiperidine hydrochloride, respectively, can be manufactured, for example, in the following manner:

30 g (0.1 mol) of N-[2-(chroman-3-yl)ethyl]-N-(2-methoxycarbonylethyl)-amine hydrochloride are dissolved in 100 ml of methanol, and then 10.5 g (0.1 mol) of triethylamine and 5.84 g (0.11 mol) of acrylonitrile are added to the solution and the whole is stirred for 15 hours at room temperature. The reaction mixture is then concentrated under a water-jet vacuum, the residue is taken up in diethyl ether and the ethereal solution is washed neutral with ice-water. The ethereal phase is dried over potassium carbonate and concentrated by evaporation. N-[2-(chroman-3-yl)ethyl]-N-(2-cyanoethyl)-N-(2-methoxycarbonylethyl)-amine is thus obtained in the form of a yellow oil.

A solution of 13.07 g (41.3 mmol) of N-[2-(chroman-3-yl)ethyl]-N-(2-cyanoethyl)-N-(2-methoxycarbonylethyl)-amine in 200 ml of tetrahydrofuran is added dropwise under a nitrogen atmosphere to a suspension of 5.73 g of sodium hydride (55% suspension in mineral oil) in 100 ml of tetrahydrofuran and the whole is stirred for 16 hours at room temperature. After adding 70 ml of 2N sulphuric acid, a yellow solution is obtained. 300 ml of diethyl ether and 100 ml of water are added thereto to form two phases. The aqueous phase is extracted three times with 100 ml of diethyl ether each time. The combined organic phases are dried over sodium sulphate, concentrated to approximately 100 ml under reduced pressure and then poured into a mixture of 80 ml of 5N hydrochloric acid and 20 ml of toluene, whereupon, while stirring and cooling, 1-[2-(chroman-3-yl)ethyl]-3-cyano-4-hydroxy-1,2,5,6-tetrahydropyridine hydrochloride or 1-[2-(chroman-3-yl)ethyl]-3-cyano-4-oxopiperidine hydrochloride, respectively, crystallises out.

EXAMPLE 28

17.4 ml of n-butyllithium in hexane are added at 0°–5° to a solution of 2.81 g of diisopropylamine in 30 ml of dry tetrahydrofuran. The whole is stirred for 30 minutes at room temperature, then cooled to −15° and a solution of 6.24 g (25 mmol) of 1-[2-(chroman-3-yl)ethyl]-4-oxopiperidine in 30 ml of tetrahydrofuran is added. After 15 minutes, a solution of 3.05 g (28 mmol) of chlorotrimethylsilane in 15 ml of tetrahydrofuran is added dropwise. The whole is stirred overnight at room temperature, the solution is filtered and the filtrate is concentrated to dryness by evaporation under reduced pressure. 1-[2-(chroman-3-yl)ethyl]-4-trimethylsilyloxy-1,2,5,6-tetrahydropyridine is thus obtained in the form of a pale yellow oil. 6.63 g (20 mmol) of the 1-[2-(chroman-3-yl)ethyl]-4-trimethylsilyloxy-1,2,5,6-tetrahydropyridine obtained are dissolved in 50 ml of dichloromethane and the solution is added dropwise to a solution, cooled to 0°, of 2.3 g (24 mmol) of chloroformic acid methyl ester and 60 mg (2.4 mmol) of anhydrous zinc bromide in 50 ml of absolute dichloromethane. After warming up to room temperature, the reaction solution is stirred for one hour and then poured onto 150 ml of saturated sodium hydrogen carbonate solution. Extraction is carried out with dichloromethane, and the combined organic phases are dried over sodium sulphate and then concentrated by evaporation. The residue is dissolved in 70 ml of ethanol and the solution is acidified with ethanolic hydrochloric acid. After adding diethyl ether and after cooling, 1-[2-(chroman-3-yl)ethyl]-4-hydroxy-1,2,5,6-tetrahydropyridine-3-carboxylic acid methyl ester hydrochloride or 1-[2-(chroman-3-yl)ethyl]-4-oxopiperidine-3-carboxylic acid methyl ester hydrochloride, respectively, having a melting point of 175°–177° crystallises out.

The 1-[2-(chroman-3-yl)ethyl]-4-oxopiperidine can be manufactured, for example, in the following manner:

First 8.45 g (55 mmol) of piperidone hydrochloride monohydrate and then 22.62 g (175 mmol) of N-ethyl-N,N-diisopropylamine are added to a solution of 16.62 g (50 mmol) of 3-[2-(p-toluenesulphonyloxy)ethyl]chroman in 100 ml of dimethylformamide. The mixture is stirred for 18 hours at 80° and, after cooling, is concentrated to dryness by evaporation under reduced pressure. The residue is dissolved in diethyl ether and washed with water. The organic phase is separated off and extracted with 2N hydrochloric acid. The hydrochloric acid extracts are combined, rendered alkaline, while cold, with concentrated sodium hydroxide solution and extracted with dichloromethane. The dichloromethane phases are combined, dried over sodium sulphate and concentrated to dryness by evaporation under reduced pressure. A dark brown resin is obtained which is purified by chromatography on 350 g of silica gel (0.040-0.063 mm) using toluene/ethyl acetate (1:1) as the eluant. 1-[2-(chroman-3-yl)ethyl]-4-oxopiperidine is obtained in the form of a pale yellow oil.

EXAMPLE 29

A solution of 2.7 g (25 mmol) of benzyl alcohol in 25 ml of tetrahydrofuran is added to a suspension of 1.2 g of sodium hydride (50% suspension in mineral oil) in 25 ml of dry tetrahydrofuran and, when the evolution of gas has subsided, the whole is heated under reflux for 30 minutes. After cooling, a solution of 8.5 g (25 mmol) of 1-[2-(benzo-1,4-dioxan-2-yl)ethyl]-1,2,5,6-tetrahydropyridine-3-carboxylic acid methyl ester in 50 ml of tetrahydrofuran is added dropwise and the whole is heated under reflux again for 5 hours. After cooling, the solvent is removed. A mixture of cis- and trans-1-[2-(benzo-1,4-dioxan-2-yl)ethyl]-4-benzyloxypiperidine-3-carboxylic acid methyl ester is obtained in the form of an oil.

EXAMPLE 30

At −10° and while stirring, 1.41 g of sodium borohydride are introduced within a period of 90 minutes into a suspension of 8.45 g (18 mmol) of 1-[2-(chroman-3-yl)ethyl]-3-methoxycarbonylpyridinium p-toluenesulphonate in 43 ml of methanol. Stirring is continued for 1 hour at 0° and for 2 hours at room temperature and then 50 ml of water are added to the reaction mixture and extraction by shaking is carried out twice with 100 ml of dichloromethane each time. The dichloromethane phases are combined, dried over magnesium sulphate and concentrated to dryness by evaporation. The crude product is purified by chromatography on 150 g of silica gel (0.063-0.2 mm) using ethyl acetate as the eluant. The main eluate, which is concentrated by evaporation, is treated with ethereal hydrochloric acid to yield 1-[2-(chroman-3-yl)ethyl]-1,2,5,6-tetrahydropyridine-3-carboxylic acid methyl ester hydrochloride having a melting point of 175°-177°.

The 1-[2-(chroman-3-yl)ethyl]-3-methoxycarbonylpyridinium p-toluenesulphonate can be manufactured, for example, in the following manner:

16.6 g (50 mmol) of 3-[2-(p-toluenesulphonyloxy)ethyl]chroman and 9.3 g (67.5 mmol) of pyridine-3-carboxylic acid methyl ester are suspended in 50 ml of butan-2-one and the suspension is boiled for 72 hours while stirring. It is cooled, the reaction mixture is concentrated under reduced pressure, and 1-[2-(chroman-3-yl)ethyl]-3-methoxycarbonylpyridinium p-toluenesulphonate is thus obtained in the form of a white foam.

EXAMPLE 31

33.2 g (0.1 mol) of 3-[2-(p-toluenesulphonyloxy)ethyl]chroman, 14.0 g of N-(2-methoxycarbonylethyl)-amine hydrochloride and 39 g of N-ethyl-N,N-diisopropylamine are dissolved under nitrogen in 750 ml of dimethylformamide and the solution is stirred for 16 hours at room temperature. The reaction mixture is subsequently concentrated to approximately 200 ml under reduced pressure, 500 ml of water are then added and the whole is extracted by shaking three times with 150 ml of dichloromethane each time. The combined organic phases are dried over sodium sulphate and concentrated to dryness by evaporation. By adding ethanolic hydrochloric acid and cooling, N-[2-(chroman-3-yl)ethyl]-N-(2-methoxycarbonylethyl)-amine hydrochloride having a melting point of 190°-192° is obtained.

EXAMPLE 32

6 ml of concentrated hydrochloric acid are added to a solution of 11.5 g (0.05 mmol) of N-[2-(chroman-3-yl)ethyl]-N-(2-cyanoethyl)-amine in 100 ml of methanol. The reaction mixture is boiled under reflux for 15 hours. After cooling, the solvent is removed under reduced pressure and the residue is crystallised from methanol/acetone. After recrystallisation from methanol/acetone, N-[2-(chroman-3-yl)ethyl]-N-(2-methoxycarbonylethyl)-amine hydrochloride having a melting point of 190°-192° is obtained (yield: 82%).

The N-[2-(chroman-3-yl)ethyl]-N-(2-cyanoethyl)-amine can be manufactured, for example, in the following manner:

17.7 g (0.1 mol) of 3-(2-aminoethyl)chroman are dissolved in 100 ml of methanol, and then 10.5 g (0.1 mol) of triethylamine and 5.84 g (0.11 mol) of acrylonitrile are added to the solution. The reaction mixture is stirred for 15 hours at room temperature and then concentrated under a water-jet vacuum. The residue is taken up in diethyl ether and washed neutral with ice-water. The ethereal phase is dried over potassium carbonate and concentrated by evaporation. N-[2-(chroman-3-yl)ethyl]-N-(2-cyanoethyl)-amine is thus obtained in the form of a pale yellow oil.

EXAMPLE 33

5.2 g of a mixture of cis- and trans-1-[2-(benzo-1,4-dioxan-2-yl)ethyl]-4-benzyloxypiperidine-3-carboxylic acid methyl ester are dissolved in 100 ml of methanol, and then 2 g of palladium-on-carbon (10%) are added and the whole is hydrogenated in a Parr apparatus for 12 hours at room temperature. The reaction mixture is then filtered over diatomaceous earth and the filtrate is concentrated to dryness by evaporation. The crude oily residue is chromatographed on silica gel using toluene/ethyl acetate (9:1) as the eluant. First the trans-1-[2-(benzo-1,4-dioxan-2-yl)ethyl]-4-hydroxypiperidine-3-carboxylic acid methyl ester and then the cis-1-[2-(benzo-1,4-dioxan-2-yl)ethyl]-4-hydroxypiperidine-3-carboxylic acid methyl ester is eluted. In each case the purified fractions are combined and concentrated by evaporation. The residue that contains the trans product is treated with fumaric acid in methanol/diethyl ether and thus yields trans-1-[2-(benzo-1,4-dioxan-2-yl)ethyl]-4-hydroxypiperidine-3-carboxylic acid methyl ester fumarate which crystallises out in the form of the hemihydrate and melts at 150°-152°. The residue that contains the cis product is treated with ethereal hydrochloric acid and thus yields cis-1-[2-(benzo-1,4-dioxan-2-yl)ethyl]-4-hydroxypiperidine-3-carboxylic acid methyl ester hydrochloride which has a melting point of 182°-185°.

EXAMPLE 34

6.8 g (20 mmol) of a mixture of cis-and trans-1-[2-(benzo-1,4-dioxan-2-yl)ethyl]-4-chloropiperidine-3-carboxylic acid methyl ester are dissolved in 20 ml of methanol. 40 ml (140 mmol) of a 3.5N solution of ammonia in methanol are added dropwise at room temperature. The mixture is left to stand at room temperature for 24 hours. The solvent is then removed under reduced pressure. The resulting residue is dissolved in dichloromethane, the solution is extracted by shaking with 2N hydrochloric acid and the acidic aqueous phase is separated off, rendered alkaline with sodium hydrogen carbonate and extracted with diethyl ether/dichloromethane (2:1). The organic extracts are washed with saturated sodium chloride solution, dried over magnesium sulphate and freed of the solvent under reduced pressure. The resulting residue is chromatographed on basic silica gel using dichloromethane/methanol (99:1) as the eluant. The eluates are combined and concentrated to dryness by evaporation. The oily residue consists of pure 4-amino-1-[2-(benzo-1,4-dioxan-2-yl)ethyl]-piperidine-3-carboxylic acid amide (cis/trans mixture).

A mixture of cis- and trans-1-[2-(benzo-1,4-dioxan-2-yl)ethyl]-4-chloropiperidine-3-carboxylic acid methyl ester can be obtained, for example, as follows:

9.7 g (30 mmol) of a mixture of cis- and trans-1-[2-(benzo-1,4-dioxan-2-yl)ethyl]-4-hydroxypiperidine-3-carboxylic acid methyl ester (for manufacture see Example 33) and 3.6 g (36 mmol) of triethylamine are dissolved in 100 ml of dichloromethane. 3.92 g (33 mmol) of thionyl chloride are added dropwise while stirring at room temperature. The mixture is stirred for 4 hours at room temperature. The triethylamine hydrochloride formed is then filtered off and the filtrate, while cold, is extracted by shaking with saturated sodium hydrogen carbonate solution. The organic phase is washed with saturated sodium chloride solution, dried over magnesium sulphate and freed of the solvent under reduced pressure. The resulting mixture of cis- and trans-1-[2-(benzo-1,4-dioxan-2-yl)ethyl]-4-chloropiperidine-3-carboxylic acid methyl ester is used further in the crude state.

EXAMPLE 35

At room temperature and while stirring, a solution of 11.94 g (30 mmol) of N-(3-ethoxycarbonylpropyl)-N-(2-bromoethyl)-N-[2-(chroman-3-yl)ethyl]-amine in 40 ml of absolute dimethylformamide is added dropwise within a period of 20 minutes to a suspension of 2.72 g (40 mmol) of sodium ethoxide in 30 ml of dimethylformamide. The reaction mixture is stirred for 16 hours at room temperature and then concentrated to dryness by evaporation under a high vacuum. Diethyl ether is added to the residue and extraction is carried out with cold 2N hydrochloric acid. The combined hydrochloric acid extracts are extracted by shaking with dichloromethane and the dichloromethane phases are dried over sodium sulphate and concentrated by evaporation in vacuo. The crude product is obtained as the residue and is chromatographed on 500 g of silica gel (0.040-0.063 mm) using ethyl acetate as the eluant. The eluate is concentrated by evaporation to yield 1-[2-(chroman-3-yl)ethyl]-piperidine-4-carboxylic acid ethyl ester in the form of a colourless oil. The 1-[2-(chroman-3-yl)ethyl]-piperidine-4-carboxylic acid ethyl ester hydrochloride produced therefrom using hydrochloric acid in diethyl ether crystallises from ethanol/diethyl ether and melts at 182°-186°.

The N-(3-ethoxycarbonylpropyl)-N-(2-bromoethyl)-N-[2-(chroman-3-yl)ethyl]-amine can be manufactured, for example, in the following manner:

17.7 g (0.1 mol) of 3-(2-aminoethyl)chroman are dissolved in 100 ml of methanol, and then 10.5 g (0.1 mol) of triethylamine and 19.5 g (0.1 mol) of 4-bromobutyric acid ethyl ester are added to the solution. The reaction mixture is stirred for 15 hours at room temperature and is then concentrated under a water-jet vacuum. The residue is taken up in diethyl ether and washed neutral with ice-water. The ethereal phase is dried over potassium carbonate and concentrated by evaporation. Oily N-(3-ethoxycarbonylpropyl)-N-[2-(chroman-3-yl)ethyl]-amine is thus obtained and can be used further in crude form.

29.1 g (0.1 mol) of N-(3-ethoxycarbonylpropyl)-N-[2-(chroman-3-yl)ethyl]-amine are dissolved in 200 ml of methanol, and then 10.5 g (0.1 mol) of triethylamine and 18.8 g (0.1 mol) of 1,2-dibromoethane are added to the solution. The reaction mixture is stirred for 16 hours at room temperature and then concentrated under a water-jet vacuum. The residue is taken up in diethyl ether and washed neutral with ice-water. The ethereal phase is dried over potassium carbonate and concentrated by evaporation. N-(3-ethoxycarbonylpropyl)-N-(2-bromoethyl)-N-[2-(chroman-3-yl)ethyl]-amine is thus obtained in the form of an oil which can be used further in the crude state.

EXAMPLE 36

In a manner analogous to that described in Examples 4, 5, 10, 12, 23, 26, 31 and 32, it is also possible to obtain N-[2-(chroman-4-yl)ethyl]-N-(2-methoxycarbonylethyl)-amine and its hydrochloride.

EXAMPLE 37

In a manner analogous to that described in Examples 1 to 3, 6 to 9, 11, 13 to 22, 24, 25, 27 to 30 and 33 to 35 it is also possible to obtain 1-[2-(chroman-4-yl)ethyl]-1,2,5,6-tetrahydropyridine-3-carboxylic acid methyl ester and its hydrochloride and 1-[2-(chroman-4-yl)ethyl]-piperidine-3-carboxylic acid ethyl ester and its hydrochloride.

EXAMPLE 38

First 5.55 g (25 mmol) of 1,2,5,6-tetrahydropyridine-3-carboxylic acid methyl ester hydrobromide (guvacoline hydrobromide) and then 11.31 g (87.5 mmol) of N-ethyl-N,N-diisopropyl-amine are added to a solution of 9 g (25 mmol) of 2,2-dimethyl-3-[2-(4-toluenesulfonyloxy)-ethyl]-chroman in 100 ml of N,N-dimethylformamide. The solution is stirred for 15 hours at 60° and then concentrated by evaporation under a high vacuum. Water is added to the residue and extraction is carried out with diethyl ether. The combined organic phases are washed with water and extracted with 2N hydrochloric acid. The combined hydrochloric acid extracts are rendered alkaline with sodium hydroxide solution (30%) while cooling and extracted with dichloromethane. The combined dichloromethane phases are dried over sodium sulfate and concentrated by evaporation in vacuo, yielding 5.52 g (67% of theoretical yield) of 1-[2-(2,2-dimethylchroman-3-yl)-ethyl]-1,2,5,6-tetrahydropyridine-3-carboxylic acid methyl ester in the form of a light-yellow oil. 1-[2-(2,2-dimethylchroman-3-yl)-ethyl]-1,2,5,6-tetrahydropyridine-3-carboxylic acid methyl ester hydrochloride, prepared therefrom with hydrochloric acid in diethyl ether, crystallises from methanol/diethyl ether and melts at 196°-197°.

2,2-dimethyl-3-[2-(4-toluenesulfonyloxy)-ethyl]-chroman can be obtained, for example, as follows:

25 g (0.6 mol) of sodium hydride dispersion (57% in mineral oil) are substantially freed of mineral oil by repeated washing with n-hexane and are then covered with a layer of 500 ml of dried tetrahydrofuran. Under a nitrogen atmosphere and while cooling in an ice bath, 134 g (0.6 mol) of phosphonoacetic acid triethyl ester of formula $(H_5C_2O)_2P(=O)CH_2C(=O)OC_2H_5$ are added dropwise thereto within a period of 1 hour. The mixture is stirred for a further 1 hour at 0°. To the homogeneous solution there is then added dropwise within a period of 30 minutes a solution of 88.57 g (0.5 mol) of 2,2-dimethyl-3-oxo-chroman [F. Camps et al., J. Heterocyclic Chem. 22, 1421 (1985)] in 300 ml of tetrahydrofuran. The mixture is stirred overnight at room temperature. The solution is then concentrated to approximately 350 ml in vacuo and poured onto 3 liters of ice-cold phosphate buffer solution (pH=6). The mixture is extracted with diethyl ether. The combined organic phases are washed with water and dried over sodium sulfate and then concentrated by evaporation in vacuo. The yellow residue is chromatographed on 4 kg of silica gel (0.040-0.063 mm) with toluene as eluant, yielding 60.3 g (49% of the theoretical yield) of 3-ethoxycarbonylmethyl-2,2-dimethyl-2H-chromene in the form of a light-yellow oil.

3 g of palladium-on-carbon (5%) are added to a solution of 59.1 g (0.24 mol) of 3-ethoxycarbonylmethyl-2,2-dimethyl-2H-chromene in 400 ml of absolute ethanol and the mixture is hydrogenated in a PARR apparatus at room temperature for 2 hours. The reaction mixture is then filtered over diatomaceous earth. The filtrate is concentrated to dryness by evaporation. The oily residue consists of pure 3-ethoxycarbonylmethyl-2,2-dimethyl-chroman.

While cooling with ice, a solution of 50 g (0.2 mol) of 3-ethoxycarbonylmethyl-2,2-dimethyl-chroman in 250 ml of absolute diethyl ether is added dropwise within a period of 1 hour to a suspension of 7.6 g (0.2 mol) of lithium aluminium hydride in 200 ml of absolute diethyl ether. The reaction mixture is then stirred for 3 hours at room temperature and then carefully decomposed with 7.5 ml of water, 7.5 ml of sodium hydroxide solution (15%) and 23 ml of water. The resulting precipitate is filtered off. The filtrate is dried over sodium sulfate and concentrated by evaporation in vacuo, yielding 39.5 g (95% of the theoretical yield) of 2,2-dimethyl-3-(2-hydroxyethyl)-chroman in the form of a colourless oil.

38 g (0.2 mol) of 4-toluenesulfonyl chloride are added at room temperature, while stirring, to a solution of 37.1 g (0.18 mol) of 2,2-dimethyl-3-(2-hydroxyethyl)-chroman in 150 ml of pyridine, the slightly exothermic reaction being maintained at room temperature with an ice bath. The mixture is then stirred for 4 hours at room temperature. The reaction mixture is then poured onto ice-water and extracted with diethyl ether. The combined ethereal phases are washed three times using 150 ml of citric acid solution (5%) each time and three times using 150 ml of water each time, then dried over sodium sulfate and concentrated by evaporation, yielding 59.1 g (89% of the theoretical yield) of 2,2-dimethyl-3-[2-(4-toluenesulfonyloxy)-ethyl]-chroman in the form of a yellow oil which is further used in that form.

EXAMPLE 39

While stirring at room temperature, 0.87 g (18 mmol) of sodium hydride dispersion in mineral oil (50%) are introduced within a period of 30 minutes to a solution of 5.66 g (15 mmol) of N-[2-(2,2-dimethylchroman-3-yl)-ethyl]-N,N-bis(2-methoxycarbonylethyl)-amine in 50 ml of absolute N,N-dimethylformamide. The reaction mixture is stirred at room temperature for 1 hour and then concentrated to dryness by evaporation under a high vacuum. Diethyl ether is added to the residue and extraction is carried out with cold 2N hydrochloric acid. The combined hydrochloric acid extracts are extracted by shaking with dichloromethane and the dichloromethane phases are dried over sodium sulfate and concentrated by evaporation in vacuo, yielding 1.95 g (34% of the theoretical yield) of 1-[2-(2,2-dimethylchroman-3-yl)-ethyl]-4-hydroxy-1,2,5,6-tetrahydropyridine-3-carboxylic acid methyl ester hydrochloride or 1-[2-(2,2-dimethylchroman-3-yl)-ethyl]-4-oxo-piperidine-3-carboxylic acid methyl ester hydrochloride, respectively, which after recrystallisation from methanol/diethyl ether has a decomposition range of 168°-170°.

N-[2-(2,2-dimethylchroman-3-yl)-ethyl]-N,N-bis(2-methoxycarbonylethyl)-amine can be prepared, for example, in the following manner:

A solution of 3.9 g (60 mmol) of sodium azide in 10 ml of water is added to a solution of 14.4 g (40 mmol) of 2,2-dimethyl-3-[2-(4-toluenesulfonyloxy)-ethyl]-chroman (prepared as described in Example 38) in 200 ml of ethanol. The mixture is boiled under reflux for 18 hours. After cooling, the ethanol is evaporated off in vacuo, water is added to the residue and extraction is carried out with dichloromethane. The dichloromethane phase is washed with water, dried over sodium sulfate and concentrated by evaporation, yielding 8.7 g (94% of the theoretical yield) of 3-(2-azidoethyl)-2,2-dimethyl-chroman in the form of a yellow oil.

A solution of 6.94 g (30 mmol) of 3-(2-azidoethyl)-2,2-dimethyl-chroman in 100 ml of absolute tetrahydrofuran is added dropwise at room temperature, within a period of 1 hour, to a suspension, stirred in a nitrogen atmosphere, of 1.14 g (30 mmol) of lithium aluminium hydride in 100 ml of absolute diethyl ether. After stirring for a further 2 hours, the reaction mixture is hydrolysed with 1.14 ml of water, 1.14 ml of sodium hydroxide solucion (15%) and 3.4 ml of water. The resulting precipitate is filtered off with suction and the filtrate is completely concentrated by evaporation in vacuo. The oil obtained as residue is dissolved in 150 ml of diethyl ether and the solution is extracted with 2N hydrochloric acid. The combined hydrochloric acid extracts are rendered alkaline with concentrated sodium hydroxide solution while cooling with ice and extracted with dichloromethane. The combined organic phases are dried over sodium sulfate and concentrated by evaporation in vacuo, yielding 5.6 g (91% of the theoretical yield) of 3-(2-aminoethyl)-2,2-dimethyl-chroman in the form of a yellow oil of which the hydrochloride melts, with decomposition, at 245°-248°.

4.74 g (55 mmol) of acrylic acid methyl ester are added at room temperature to a solution of 5.13 g (25 mmol) of 3-(2-aminoethyl)-2,2-dimethyl-chroman in 50 ml of methanol. The mixture is stirred for 16 hours at room temperature and then concentrated by evaporation in vacuo, yielding 9.43 g (100% of the theoretical yield) of N-[2-(2,2-dimethylchroman-3-yl)-ethyl]-N,N- bis(2-methoxycarbonylethyl)-amine in the form of a light-yellow oil which is further used in that form.

EXAMPLE 40

While cooling with ice, a solution of 1.3 g (15 mmol) of acrylic acid methyl ester in 25 ml of methanol is added dropwise within a period of 15 minutes to a solution of 3.08 g (15 mmol) of 3-(2-amino-ethyl)-2,2-dimethyl-chroman (prepared as described in Example 39) in 75 ml of methanol. The reaction mixture is then stirred at 0° for 6 hours and then concentrated by evaporation in vacuo. The oily residue is chromatographed on 300 g of silica gel (0.040-0.063 mm) with ethyl acetate as eluant, yielding 2.75 g (63% of the theoretical yield) of N-[2-(2,2-dimethylchroman-3-yl)-ethyl]-N-(2-methoxycarbonylethyl)-amine in the form of a light-yellow oil of which the hydrochloride melts at 132°-134°.

EXAMPLE 41

15 ml of a 5N solution of ammonia in methanol are added to a solution of 2.91 g (10 mmol) of N-[2-(2,2-dimethylchroman-3-yl)-ethyl]-N-(2-methoxycarbonylethyl)-amine (prepared as described in Example 40) in 20 ml of methanol and the reaction mixture is left to react in a closed vessel for 6 days at room temperature. The mixture is then concentrated by evaporation and N-(2-aminocarbonylethyl)-N-[2-(2,2-dimethylchroman-3-yl)-ethyl]-amine hydrochloride, having a melting range of 194°-196°, is prepared from the residue with methanolic hydrochloric acid.

EXAMPLE 42

While stirring at a temperature of from 0° to 5°, a solution of 0.86 g (9.9 mmol) of acrylic acid methyl ester in 10 ml of methanol is added dropwise within a period of 15 minutes to a solution of 2.23 g (10 mmol) of 3-(2-aminoethyl)-2,2-dimethyl-6-fluoro-chroman in 50 ml of methanol. The reaction mixture is then stirred for 16 hours at from 0° to 5° and then concentrated by evaporation in vacuo. The oily residue is chromatographed on 200 g of silica gel (0.040-0.063 mm) with ethyl acetate as eluant, yielding 1.9 g (61.4% of the theoretical yield) of N-[2-(2,2-dimethyl-6-fluoro-chroman-3-yl)-ethyl]-N-(2-methoxycarbonylethyl)-amine in the form of a light-yellow oil. The N-[2-(2,2-dimethyl-6-fluoro-chroman-3-yl)-ethyl]-N-(2-methoxycarbonylethyl)-amine hydrochloride, prepared therefrom with hydrochloric acid in diethyl ether, crystallises from acetone/diethyl ether and melts at 129°-131°.

3-(2-aminoethyl)-2,2-dimethyl-6-fluoro-chroman can be prepared, for example, as follows:

83.1 g (0.2 mol) of potassium carbonate are added, while stirring, to a solution of 28.0 g (0.2 mol) of 5-fluoro-2-hydroxy-benzaldehyde [prepared according to Y. Suzuki and H. Takahashi, Chem. Pharm. Bull. 31, 1751 (1983)] in 500 ml of N,N-dimethylformamide. 36.3 g (0.2 mol) of 3,3-dimethylacrylic acid ethyl ester are added to the resulting viscous suspension. The reaction mixture is then stirred for 16 hours at 150° and, after cooling to room temperature, concentrated by evaporation in vacuo. Water is added to the resulting solid residue and the aqueous mixture is extracted with diethyl ether. The combined ethereal phases are washed in succession with water, 2N hydrochloric acid, 2N sodium hydroxide solution and again with water, dried over sodium sulfate and concentrated by evaporation in vacuo. The resulting oily residue is chromatographed on 1000 g of silica gel (0.040-0.063 mm) with toluene as eluant, yielding 19.5 g (55% of the theoretical yield) of 2,2-dimethyl-6-fluoro-2H-chromene in the form of a light-yellow oil.

40.6 g (0.2 mol) of m-chloroperbenzoic acid are added, while stirring at from 15° to 20°, to a solution of 17.8 g (0.1 mol) of 2,2-dimethyl-6-fluoro-2H-chromene in 300 ml of trichloromethane. 17.1 g (0.15 mol) of trifluoroacetic acid are added rapidly to the resulting suspension at room temperature. The reaction mixture is then stirred at room temperature for 2 hours and then an aqueous solution of sodium sulfite/sodium hydrogen carbonate (1:1) is added thereto. The organic phase is separated off, washed in succession with water and saturated sodium chloride solution, dried over sodium sulfate and concentrated by evaporation in vacuo. The resulting residue is subjected to bulb tube distillation under a high vacuum at 160°. The distillate is dissolved in diethyl ether and the solution is washed in succession with sodium hydrogen carbonate solution and saturated sodium chloride solution, dried over sodium sulfate and again concentrated by evaporation in vacuo. The resulting oily residue is chromatographed on 500 g of silica gel (0.040-0.063 mm) with toluene as eluant, yielding 7.76 g (40% of the theoretical yield) of 2,2-dimethyl-6-fluoro-3-oxo-chroman in the form of a light-yellow oil.

While stirring at from 0° to 5°, a solution of 5.7 g (29 mmol) of 2,2-dimethyl-6-fluoro-3-oxo-chroman in 100 ml of absolute tetrahydrofuran is added dropwise within a period of 30 minutes to a suspension of 1.69 g (35 mmol) of sodium hydride dispersion (55% in mineral oil), which has been substantially freed of mineral oil beforehand by repeated washing with n-hexane, in 100 ml of absolute tetrahydrofuran. The mixture is then stirred at from 0° to 5° for 30 minutes and then a solution of 7.9 g (35 mmol) of phosphonoacetic acid triethyl ester of the formula $(H_5C_2O)_2P(=O)CH_2C(=O)OC_2H_5$ in 70 ml of absolute tetrahydrofuran is added dropwise thereto within a period of 30 minutes at from 0° to 5°. The reaction mixture is stirred for a further 30 minutes at from 0° to 5° and then for 16 hours at room temperature and then poured into 700 ml of cold phosphate buffer solution (pH=6). The resulting mixture is extracted with diethyl ether. The combined organic phases are washed in succession with phosphate buffer solution (pH=7) and water, dried over sodium sulfate and concentrated by evaporation. The resulting red oil is chromatographed on 400 g of silica gel (0.040-0.063 mm) with toluene as eluant, yielding 5.76 g (75% of the theoretical yield) of 3-ethoxycarbonylmethyl-2,2-dimethyl-6-fluoro-2H-chromene in the form of an orange-coloured oil.

140 mg of palladium-on-carbon (5%) are added to a solution of 3.4 g (13 mmol) of 3-ethoxycarbonylmethyl-2,2-dimethyl-6-fluoro-2H-chromene in 30 ml of absolute ethanol and the mixture is hydrogenated at normal pressure and room temperature for 90 minutes. The catalyst is then filtered off and the filtrate is concentrated by evaporation in vacuo, yielding 3.47 g of 3-ethoxycarbonylmethyl-2,2-dimethyl-6-fluoro-chroman in the form of a light-yellow oil.

A solution of 3.4 g (12.7 mmol) of 3-ethoxycarbonylmethyl-2,2-dimethyl-6-fluoro-chroman in 40 ml of absolute diethyl ether is added dropwise within a period of 30 minutes, while cooling with ice, to a suspension of 0.97 g (25.5 mmol) of lithium aluminium hydride in 30 ml of absolute diethyl ether. The reaction mixture is then stirred for 2 hours at room temperature and then carefully decomposed with 1 ml of water, 1 ml of sodium hydroxide solution (15%) and 3 ml of water. The resulting precipitate is filtered off with suction and the filtrate is dried over sodium sulfate and concentrated by evaporation in vacuo, yielding 2.75 g (96% of the theoretical yield) of 2,2-dimethyl-6-fluoro-3-(2-hydroxyethyl)-chroman in the form of a light-yellow oil.

4.01 g (21 mmol) of 4-toluenesulfonyl chloride are added while stirring at room temperature to a solution of 4.48 g (20 mmol) of 2,2-dimethyl-6-fluoro-3-(2-hydroxyethyl)-chroman in 30 ml of absolute pyridine, the slightly exothermic reaction being maintained at room temperature with an ice bath. The reaction mixture is then stirred at room temperature for 2 hours, then poured onto ice-water and the mixture is extracted with diethyl ether. The combined organic phases are washed while cold with 2N hydrochloric acid and then with water, dried over sodium sulfate and concentrated by evaporation in vacuo, yielding 6.5 g (85.8% of the theoretical yield) of 2,2-dimethyl-6-fluoro-3-[2-(4-toluenesulfonyloxy)ethyl]-chroman in the form of a light-yellow oil.

A solution of 1.62 g (24.9 mmol) of sodium azide in 10 ml of water is added to a solution of 6.3 g (16.6 mmol) of 2,2-dimethyl-6-fluoro-3-[2-(4-toluenesulfonyloxy)-ethyl]-chroman in 100 ml of ethanol. The mixture is boiled under reflux for 18 hours. After cooling, the ethanol is evaporated off in vacuo and water is added to the residue. The aqueous mixture is extracted with diethyl ether. The combined organic phases are washed with water, dried over sodium sulfate and concentrated by evaporation in vacuo, yielding 4.13 g (100% of the theoretical yield) of 3-(2-azidoethyl)-2,2-dimethyl-6-fluoro-chroman in the form of a light-yellow oil.

A solution of 4.0 g (16 mmol) of 3-(2-azidoethyl)-2,2-dimethyl-6-fluoro-chroman in 30 ml of absolute tetrahydrofuran is added dropwise within a period of 30 minutes to a suspension of 0.61 g (16 mmol) of lithium aluminium hydride in 30 ml of absolute diethyl ether. The reaction mixture is then stirred for 2 hours at room temperature and then carefully decomposed with 0.61 ml of water, 0.61 ml of sodium hydroxide solution (15%) and 1.83 ml of water. The resulting precipitate is filtered off with suction and the filtrate is concentrated by evaporation in vacuo. The oily residue is dissolved in diethyl ether and the solution is extracted with 2N hydrochloric acid. The combined hydrochloric acid extracts are rendered alkaline with sodium hydroxide solution (30%) while cooling with ice and extracted with dichloromethane. The combined dichloromethane phases are dried over sodium sulfate and concentrated by evaporation in vacuo, yielding 3.21 g (90% of the theoretical yield) of 3-(2-aminoethyl)-2,2-dimethyl-6-fluoro-chroman in the form of a yellow oil. 3-(2-aminoethyl)-2,2-dimethyl-6-fluoro-chroman hydrochloride, prepared therefrom with hydrochloric acid in diethyl ether, crystallises from methanol/diethyl ether and has a melting range of from 249° to 251°.

EXAMPLE 43

In a manner analogous to that described in Examples 38 to 42, it is also possible to prepare each of the following compounds or a salt thereof:

N-(2,2-dimethylchroman-3-ylmethyl)-N-(2-methoxycarbonylethyl)-amine;
N-(2,2-dimethylchroman-3-yl)-N-(2-methoxycarbonylethyl)-amine;
N-[2-(6-cyano-2,2-dimethyl-chroman-3-yl)-ethyl]-N-(2-methoxycarbonylethyl)-amine;
3-[N-(2-(2,2-dimethylchroman-3-yl)-ethyl)-amino]-propionic acid morpholide;
1-[2-(2,2-dimethyl-6-fluoro-chroman-3-yl)-ethyl]-1,2,5,6-tetrahydropyridine-3-carboxylic acid methyl ester, and
1-[2-(6-cyano-2,2-dimethyl-chroman-3-yl)-ethyl]-4-hydroxy-1,2,5,6-tetrahydropyridine-3-carboxylic acid methyl ester or
1-[2-(6-cyano-2,2-dimethyl-chroman-3-yl)-ethyl]-4-oxo-piperidine-3-carboxylic acid methyl ester, respectively.

EXAMPLE 44

While stirring at a temperature of from 0° to 5°, a solution of 1.42 g (16.4 mmol) of acrylic acid methyl ester in 10 ml of methanol is added dropwise within a period of 15 minutes to a solution of 3.0 g (16.5 mmol) of 3-aminomethyl-6-fluoro-chroman in 80 ml of methanol. The reaction mixture is then stirred for 16 hours at from 0° to 5° and then concentrated by evaporation in vacuo. The oily residue is chromatographed on 250 g of silica gel (0.040–0.063 mm) with ethyl acetate as eluant, yielding 2.85 g of N-[(6-fluorochroman-3-yl)methyl]-N-(2-methoxycarbonylethyl)-amine in the form of a light-yellow oil. The N-[(6-fluorochroman-3-yl)methyl]-N-(2-methoxycarbonylethyl)-amine hydrochloride, prepared therefrom with hydrochloric acid in diethyl ether, crystallizes from acetone/diethyl ether and melts at 163°–165°. The N-[(6-fluorochroman-3-yl)methyl]-N-(2-methoxycarbonylethyl)-amine cyclamate, prepared from the crude base with N-cyclohexyl-sulfamic acid, crystallizes from acetone and melts at 155°–156°.

The 3-aminomethyl-6-fluoro-chroman can be prepared, for example, as follows:

While stirring at room temperature, 5.74 g (0.051 mol) of 1,4-diazabicyclo[2.2.2]octane (DABCO) are added to a solution of 17.92 g (0.128 mol) of 5-fluoro-2-hydroxy-benzaldehyde (example 42) in 42 ml (0.639 mol) of acrylonitrile. The reaction mixture is then stirred for 16 hours at 90°.

After cooling to room temperature, the mixture is diluted with 50 ml of diethyl ether and then washed in succession with 2N sodium hydroxide solution and water. The organic phase is dried over sodium sulfate and concentrated to dryness by evaporation in vacuo. The resulting red crystals (22 g) are recrystallized from methanol, yielding 13.3 g of 3-cyano-6-fluoro-2H-chromene in the form of light-yellow crystals which melt at 97°–100°.

In an argon atmosphere, a mixture of 0.89 g (6.66 mmol) of aluminium trichloride in 40 ml of absolute diethyl ether is added dropwise while stirring at room temperature to a suspension of 1.52 g (40 mmol) of lithium aluminium hydride in 50 ml of absolute diethyl ether. Subsequently, a solution of 3.5 g (20 mmol) of 3-cyano-6-fluoro-2H-chromene in 50 ml of absolute tetrahydrofuran is added dropwise within a period of 20 minutes to the diethyl ether solution. The reaction mixture is then boiled under reflux for 16 hours. After cooling to room temperature, the reaction mixture is carefully decomposed with 1.52 ml of water, 1.52 ml of sodiumhydroxide solution (15%) and 4.6 ml of water. The resulting precipitate is filtered off with suction and the filtrate is concentrated by evaporation in vacuo. The oily residue is dissolved in diethyl ether and the etheral solution is washed with water and then extracted with 2N hydrochloric acid. The combined hydrochloric acid extracts are rendered alkaline with sodium hydroxide solution (30%) while cooling and extracted with dichloromethane. The combined dichloromethane phases are dried over sodium sulfate and concentrated by evaporation in vacuo, yielding 1.89 g of 3-aminomethyl-6-fluoro-chroman in the form of a light-yellow oil. 3-Aminomethyl-6-fluoro-chroman hydrochloride, prepared therefrom with hydrochloric acid in diethyl ether, crystallizes from methanol/acetone and has a melting range of from 208° to 211°.

EXAMPLE 45

3 g (100 mmol) of N-[2-(chroman-3-yl)ethyl]-N-(2-methoxycarbonylethyl)-amine hydrochloride (example 4) are added to 20 ml of 5.5N methanolic ammonia solution. The mixture is stirred in a bomb tube for 12 hours at 60°. Subsequently, the reaction mixture is concentrated by evaporation, the resulting residue is dissolved in 2N hydrochloric acid, and the acidic solution is extracted with diethyl ether. The acidic aqueous phase is rendered alkaline with 2N sodium hydroxide solution and extracted with diethyl ether. The combined ethereal phases are washed in succession with water and saturated sodium chloride solution, dried over magnesium sulfate, and concentrated by evaporation, yielding the crude base in the form of an oil. The crude base is dissolved in a small amount of isopropanol. Ethereal hydrochloric acid is added to the isopropanol solution until the mixture gives a weakly acidic reaction. The precipitate is filtered off and recrystallized from isopropanol/diethyl ether, yielding 0.6 g of N-(2-aminocarbonylethyl)-N-[2-(chroman-3-yl)ethyl]amine hydrochloride melting at 220° to 222°.

EXAMPLE 46

Tablets, containing 25 mg of active ingredient, for example N-[2-(2,2-dimethylchroman-3-yl)-ethyl]-N-(2-methoxycarbonylethyl)-amine hydrochloride, can be prepared as follows:

| Constituents (for 1000 tablets): | |
| --- | --- |
| active ingredient | 25.0 g |
| lactose | 100.7 g |
| wheat starch | 7.5 g |
| polyethylene glycol 6000 | 5.0 g |
| talc | 5.0 g |
| magnesium stearate | 1.8 g |
| demineralised water | q.s. |

Preparation

All the solid ingredients are first forced through a sieve of 0.6 mm mesh width. Then the active ingredient, the lactose, the talc, the magnesium stearate and half the starch are mixed together. The other half of the starch is suspended in 40 ml of water and this suspension is added to a boiling solution of the polyethylene glycol in 100 ml of water. The resulting starch paste is added to the main mixture and the mixture is granulated, if necessary with the addition of water. The granulate is dried overnight at 35°, forced through a sieve of 1.2 mm mesh width and compressed to form tablets of approximately 6 mm diameter that are concave on both sides.

EXAMPLE 47

Tablets, containing 50 mg of active ingredient, for example 1-(benzo-1,4-dioxan-2-ylmethyl)-piperidine-3-carboxylic acid methyl ester hydrochloride, are prepared as follows:

| Constituents (for 10.000 tablets): | |
| --- | --- |
| active ingredient | 500.00 g |
| lactose | 140.80 g |
| potato starch | 274.70 g |
| stearic acid | 10.00 g |
| talc | 50.00 g |
| magnesium stearate | 2.50 g |
| colloidal silica | 32.00 g |
| ethanol | q.s. |

A mixture of the active ingredient, the lactose and 194.70 g of potato starch is moistened with an ethanolic solution of the stearic acid and granulated through a sieve. After drying, the remaining potato starch, the talc, the magnesium stearate and the colloidal silica are mixed in and the mixture is compressed to form tablets each weighing 0.1 g which, if desired, may be provided with dividing notches for more accurate adaptation of the dose.

100 mg of active ingredient can be incorporated in analogous manner.

EXAMPLE 48

Capsules, containing 0.025 g of active ingredient, for example N-[2-(chroman-3-yl)ethyl]-N-(2-methoxycarbonylethyl)-amine hydrochloride, can be prepared as follows:

| Constituents (for 1000 capsules): | |
| --- | --- |
| active ingredient | 25.00 g |
| lactose | 249.00 g |
| gelatine | 2.00 g |
| corn starch | 10.00 g |
| talc | 15.00 g |
| water | q.s. |

The active ingredient is mixed with the lactose and the mixture is moistened uniformly with an aqueous solution of the gelatine and granulated through a sieve of 1.2 to 1.5 mm mesh width. The granulate is mixed with the dried corn starch and the talc and is introduced in 300 mg portions into hard gelatine capsules (size 1).

EXAMPLE 49

In a manner analogous to that described in Examples 46 to 48 it is also possible to prepare pharmaceutical preparations containing as active ingredient a different compound of formula I or a tautomer and/or a pharmaceutically acceptable salt thereof or a different compound of formula IVc or a pharmaceutically acceptable salt thereof, for example according to Examples 1 to 45.

We claim:

1. A compound of the formula

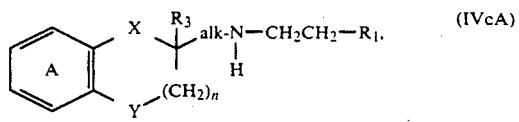

in which $R_1$ represents a carboxy, lower alkoxycarbonyl, carbamoyl, N-lower alkylcarbamoyl, N,N-di-lower alkylcarbamoyl, hydroxymethyl, lower alkanoyloxymethyl, lower alkanesulphonyloxymethyl, benzoyloxymethyl or pyridoyloxymethyl, $R_3$ represents hydrogen or lower alkyl, alk represents lower alkylene that links the ring system with the NH group shown in formula (IVcA) by up to and including 3 carbon atoms or alk represents lower alkylidene, the ring A is unsubstituted or is mono-, di- or polysubstituted by substituents selected from the group consisting of hydroxy, lower alkoxy, lower alkanoyloxy, halogen, lower alkyl and trifluoromethyl and either (a) X represents a methylene group, Y represents an oxygen atom and n represents 1 or (b) X represents an oxygen atom, Y represents a methylene group and n represents 1 or (c) X represents a direct bond, Y represents an oxygen atom and n represents 2, or a pharmaceutically acceptable salt thereof.

2. A compound according to claim 1 of the formula IVcA in which $R_1$ represents carboxy, lower alkoxycarbonyl, carbamoyl, N-lower alkylcarbamoyl or N,N-di-lower alkylcarbamoyl, $R_3$ represents hydrogen or lower alkyl, alk represents lower alkylene that links the ring system with the NH group shown in formula IVcA by up to and including 3 carbon atoms, or alk represents lower alkylidene, the ring A is unsubstituted or is mono-, di- or polysubstituted by substituents selected from the group consisting of hydroxy, lower alkoxy, lower alkanoyloxy, halogen, lower alkyl and trifluoromethyl, X represents a methylene group, Y represents an oxygen atom and n represents 1, or a pharmaceutically acceptable salt thereof.

3. A compound according to claim 1 of the formula IVcA, in which $R_1$ represents carboxy, hydroxymethyl, $C_2$-$C_5$alkanoyloxymethyl, $C_1$-$C_4$alkoxycarbonyl or carbamoyl, $R_3$ represents hydrogen or $C_1$-$C_4$alkyl, alk represents $C_1$-$C_4$alkylene that links the ring system with the NH group shown in formula IVcA by up to and including 3 carbon atoms, the ring A is unsubstituted or substituted by $C_1$-$C_4$alkoxy, and either (a) X represents a methylene group, Y represents an oxygen atom and n represents 1 or (b) X represents an oxygen atom, Y represents a methylene group and n represents 1 or (c) X represents a direct bond, Y represents an oxygen atom and n represents 2, or a pharmaceutically acceptable salt thereof.

4. A compound according to claim 1 of the formula IVcA in which $R_1$ represents $C_1$-$C_4$alkoxycarbonyl, $R_3$ represents hydrogen or $C_1$-$C_4$alkyl, alk represents $C_1$-$C_4$alkylene that links the ring system with the NH group shown in formula IVcA by up to and including 3 carbon atoms, the ring A is unsubstituted, X represents a methylene group, Y represents an oxygen atom, and n represents 1, or a pharmaceutically acceptable salt thereof.

5. A compound according to claim 1 being N-[2-(chroman-3-yl)-ethyl]-N-(2-methoxycarbonylethyl)-amine or a pharmaceutically acceptable salt thereof.

6. A compound according to claim 1 being N-(2-aminocarbonylethyl)-N-[2-(chroman-3-yl)ethyl]-amine or a pharmaceutically acceptable salt thereof.

7. A compound according to claim 1 being N-[(6-fluorochroman-3-yl)-methyl]-N-(2-methoxycarbonylethyl)-amine or a pharmaceutically acceptable salt thereof.

8. A pharmaceutical preparation comprising a nootropically effective amount of a compound according to claim 1 or of a pharmaceutically acceptable salt thereof, together with a pharmaceutically acceptable adjunct.

9. Method for the treatment of the symptoms of cerebral insufficiency, characterised in that a nootropically effective amount of a compound according to claim 1 in free form or in form of a pharmaceutically acceptable salt, is administered a subject in need of such treatment.

* * * * *